United States Patent
Haveri et al.

(10) Patent No.: US 12,100,492 B2
(45) Date of Patent: *Sep. 24, 2024

(54) NASAL AND ORAL RESPIRATION SENSOR

(71) Applicant: SunMed Group Holdings, LLC, Grand Rapids, MI (US)

(72) Inventors: Heikki Haveri, Huhmari (FI); Janne Ranta, Espoo (FI)

(73) Assignee: SunMed Group Holdings, LLC, Grand Rapids, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/118,090

(22) Filed: Mar. 6, 2023

(65) Prior Publication Data

US 2023/0352128 A1 Nov. 2, 2023

Related U.S. Application Data

(63) Continuation of application No. 16/438,410, filed on Jun. 11, 2019, now Pat. No. 11,600,365, which is a
(Continued)

(51) Int. Cl.
*G16H 10/60* (2018.01)
*G08B 5/36* (2006.01)
(Continued)

(52) U.S. Cl.
CPC .............. *G16H 10/60* (2018.01); *G08B 5/36* (2013.01); *G16H 80/00* (2018.01); *H04L 67/12* (2013.01); *H04W 48/08* (2013.01); *H04W 24/08* (2013.01)

(58) Field of Classification Search
None
See application file for complete search history.

(56) References Cited

U.S. PATENT DOCUMENTS

| | | | |
|---|---|---|---|
| 4,777,963 | A | 10/1988 | McKenna |
| 5,005,571 | A | 4/1991 | Dietz |

(Continued)

FOREIGN PATENT DOCUMENTS

| | | |
|---|---|---|
| CA | 3064505 | 11/2018 |
| CN | 101610806 | 12/2009 |

(Continued)

OTHER PUBLICATIONS

Official Action with English Translation for China Patent Application No. 201880089070.5, dated Nov. 28, 2023 2 pages.
(Continued)

*Primary Examiner* — Hong S Cho
(74) *Attorney, Agent, or Firm* — Sheridan Ross P.C.

(57) ABSTRACT

An apparatus having a support structure, including two nasal flow passages aligned with one another and with respect to a nasal respiratory flow direction, and an oral flow passage disposed transverse to the two nasal flow passages, along an oral respiratory flow direction, the nasal flow passages and oral flow passages having thermistors to monitor a patient's respiration, and the apparatus having a thermistor for monitoring ambient conditions and an accelerometer for monitoring movement of the apparatus. The apparatus also detecting and distinguishing between oral and individual nasal air flows, and integration of the apparatus and monitored data with a network.

20 Claims, 50 Drawing Sheets

Related U.S. Application Data continuation-in-part of application No. 16/218,388, filed on Dec. 12, 2018.

(60) Provisional application No. 62/597,870, filed on Dec. 12, 2017.

(51) Int. Cl.
*G16H 80/00* (2018.01)
*H04L 67/12* (2022.01)
*H04W 24/08* (2009.01)
*H04W 48/08* (2009.01)

(56) References Cited

U.S. PATENT DOCUMENTS

| | | | |
|---|---|---|---|
| 5,069,222 A | 12/1991 | McDonald, Jr. | |
| 5,190,048 A | 3/1993 | Wilkinson | |
| 5,195,529 A | 3/1993 | Malkamaki | |
| 5,413,111 A | 5/1995 | Wilkinson | |
| 5,485,850 A | 1/1996 | Dietz | |
| 5,671,733 A | 9/1997 | Raviv et al. | |
| 6,342,040 B1 | 1/2002 | Starr et al. | |
| 6,368,287 B1 | 4/2002 | Hadas | |
| 6,811,538 B2 | 11/2004 | Westbrook | |
| 7,024,235 B2 | 4/2006 | Melker et al. | |
| 7,087,027 B2 | 8/2006 | Page | |
| 7,533,670 B1 | 5/2009 | Freitag et al. | |
| 7,806,120 B2 | 10/2010 | Loomas et al. | |
| 7,856,979 B2 | 12/2010 | Doshi et al. | |
| 8,020,558 B2 | 9/2011 | Christopher et al. | |
| 8,439,032 B2 | 5/2013 | Andrieux et al. | |
| 8,515,547 B2* | 8/2013 | Mass | G16H 40/67 607/60 |
| 8,579,829 B2 | 11/2013 | Feldman | |
| 8,591,430 B2 | 11/2013 | Amurthur et al. | |
| 8,774,776 B1 | 7/2014 | Ornstein | |
| 8,911,380 B1 | 12/2014 | Feldman et al. | |
| 9,044,565 B2 | 6/2015 | Colman et al. | |
| 9,192,351 B1 | 11/2015 | Telfort et al. | |
| 9,250,104 B2 | 2/2016 | Greiner et al. | |
| 9,492,106 B2 | 11/2016 | Haveri | |
| 10,230,491 B2* | 3/2019 | Soro | H04L 1/0021 |
| 11,600,365 B2 | 3/2023 | Haveri et al. | |
| 2003/0168067 A1 | 9/2003 | Dougill et al. | |
| 2003/0199945 A1 | 10/2003 | Ciulla | |
| 2006/0270941 A1 | 11/2006 | Xie et al. | |
| 2007/0093724 A1 | 4/2007 | Nakano | |
| 2007/0125380 A1 | 6/2007 | Acker et al. | |
| 2007/0175473 A1 | 8/2007 | Lewis et al. | |
| 2007/0208269 A1 | 9/2007 | Mumford et al. | |
| 2008/0039739 A1 | 2/2008 | Buja | |
| 2008/0221470 A1 | 9/2008 | Sather et al. | |
| 2008/0232604 A1 | 9/2008 | Dufresne et al. | |
| 2008/0243020 A1 | 10/2008 | Chou | |
| 2009/0069646 A1 | 3/2009 | Yamamori et al. | |
| 2009/0076341 A1 | 3/2009 | James et al. | |
| 2009/0099471 A1 | 4/2009 | Broadley et al. | |
| 2009/0133699 A1 | 5/2009 | Nalagatla et al. | |
| 2009/0203970 A1 | 8/2009 | Wijesiriwardana | |
| 2009/0221888 A1 | 9/2009 | Wijesiriwardana | |
| 2009/0306528 A1 | 12/2009 | Curti et al. | |
| 2009/0318781 A1 | 12/2009 | Henke et al. | |
| 2010/0113956 A1 | 5/2010 | Curti et al. | |
| 2010/0163043 A1 | 7/2010 | Hart et al. | |
| 2010/0252042 A1 | 10/2010 | Kapust et al. | |
| 2011/0066061 A1 | 3/2011 | Colman et al. | |
| 2011/0108041 A1 | 5/2011 | Sather et al. | |
| 2011/0125052 A1 | 5/2011 | Davenport et al. | |
| 2011/0197689 A1 | 8/2011 | Haveri et al. | |
| 2011/0218451 A1 | 9/2011 | Lai et al. | |
| 2011/0290256 A1 | 12/2011 | Sather et al. | |
| 2011/0301484 A1 | 12/2011 | Curti et al. | |
| 2012/0052469 A1 | 3/2012 | Sobel et al. | |
| 2012/0203128 A1 | 8/2012 | Levison et al. | |
| 2012/0226182 A1 | 9/2012 | Bonato et al. | |
| 2012/0257561 A1 | 10/2012 | Redding | |
| 2013/0032148 A1 | 2/2013 | Neely | |
| 2014/0083419 A1 | 3/2014 | Collazo et al. | |
| 2014/0088454 A1 | 3/2014 | Mack | |
| 2014/0236037 A1 | 8/2014 | Banet et al. | |
| 2014/0275857 A1 | 9/2014 | Schwartz | |
| 2015/0081763 A1 | 3/2015 | Sipola et al. | |
| 2015/0313535 A1 | 11/2015 | Alshaer et al. | |
| 2016/0015289 A1 | 1/2016 | Simon et al. | |
| 2016/0029148 A1 | 1/2016 | Jackson et al. | |
| 2016/0045161 A1 | 2/2016 | Alshaer et al. | |
| 2016/0150981 A1 | 6/2016 | Baker et al. | |
| 2016/0210099 A1* | 7/2016 | Hampapuram | A61B 5/7445 |
| 2016/0271351 A1 | 9/2016 | Frater et al. | |
| 2016/0345893 A1 | 12/2016 | von Janecek et al. | |
| 2017/0007795 A1 | 1/2017 | Pedro et al. | |
| 2017/0020444 A1* | 1/2017 | Lurie | A61B 5/74 |
| 2017/0028231 A1 | 2/2017 | Zhao et al. | |
| 2017/0079580 A1 | 3/2017 | Moore et al. | |
| 2017/0147772 A1* | 5/2017 | Meehan | G16H 40/63 |
| 2017/0151409 A1 | 6/2017 | Peacock et al. | |
| 2017/0173262 A1 | 6/2017 | Veltz | |
| 2018/0008849 A1 | 1/2018 | Baker | |
| 2018/0078798 A1 | 3/2018 | Fabian et al. | |
| 2018/0125700 A1 | 5/2018 | Ray et al. | |
| 2018/0146887 A1 | 5/2018 | Cheng | |
| 2018/0153440 A1 | 6/2018 | Lee et al. | |
| 2018/0172664 A1 | 6/2018 | Love et al. | |
| 2018/0279881 A1 | 10/2018 | McCalmont et al. | |
| 2018/0333056 A1 | 11/2018 | Chou | |
| 2018/0333558 A1 | 11/2018 | Levendowski et al. | |
| 2018/0338706 A1 | 11/2018 | Shuster et al. | |
| 2019/0061691 A1 | 2/2019 | Farges | |
| 2019/0116088 A1 | 4/2019 | Mueglitz et al. | |
| 2019/0174574 A1 | 6/2019 | Filgueiras et al. | |
| 2019/0175064 A1 | 6/2019 | Haveri et al. | |
| 2020/0305760 A1 | 10/2020 | Naser | |

FOREIGN PATENT DOCUMENTS

| | | |
|---|---|---|
| CN | 101898007 | 12/2010 |
| CN | 104523276 | 4/2015 |
| EP | 0604564 | 4/1998 |
| EP | 1044037 | 4/2006 |
| EP | 2913003 | 9/2015 |
| JP | 2006-320731 | 11/2006 |
| JP | 2006-320732 | 11/2006 |
| JP | 2007-222382 | 9/2007 |
| JP | 2009-136423 | 6/2009 |
| JP | 4607799 | 1/2011 |
| JP | 2014-124323 | 7/2014 |
| JP | 2017-170108 | 9/2017 |
| JP | 2018-509947 | 4/2018 |
| JP | 6329975 | 5/2018 |
| JP | 2018-527996 | 9/2018 |
| JP | 2019-513061 | 5/2019 |
| WO | WO 1999/034864 | 7/1999 |
| WO | WO 2004/032719 | 4/2004 |
| WO | WO 2006/026387 | 3/2006 |
| WO | WO 2013/043847 | 3/2013 |
| WO | WO 2015/111648 | 7/2015 |
| WO | WO 2016/185470 | 11/2016 |
| WO | WO 2017/165583 | 9/2017 |
| WO | WO 2017/199089 | 11/2017 |
| WO | WO 2018/098527 | 6/2018 |
| WO | WO 2019/049116 | 3/2019 |

OTHER PUBLICATIONS

Official Action for European Patent Application No. 22168445.9, dated Oct. 30, 2023 5 pages.
International Preliminary Report on Patentability for Application No. PCT/US2020/037060, dated Jul. 19, 2021, 18 pages.
International Search Report and Written Opinion for Application No. PCT/US2020/037060, dated Sep. 23, 2020, 12 pages.

(56) References Cited

OTHER PUBLICATIONS

Avalur, Divya S., "Human Breath Detection using a Microphone", Master's thesis, University of Groningen, Faculty of Mathematics and Natural Sciences, Aug. 30, 2013, 67 pages.

Binu, E. et al., Real Time Monitoring of Respiratory Parameters Using a Wireless Portable System, International Journal of Engineering Development and Research, 2014, vol. 3, Issue 1, ISSN: 23-21-9939, pp. 283-287.

International Search Report and Written Opinion for Application No. PCT/US2018/065247, dated Jun. 5, 2019, 38 pages.

Invitation to Pay Additional Fees for Application No. PCT/US2018/065247, dated Mar. 14, 2019, 15 pages.

Jinesh, Matthew, et al. "A miniature optical breathing sensor", Biomed Opt Express. Dec. 1, 2012;3(12): 3325-3331. Published online Nov. 26, 2012. doi: 10.1364/BOE.3.003325.

Australian Office Action for Application No. 2020290445, dated Sep. 9, 2022, 2 pages.

Extended European Search Report for Application No. 22168445.9, dated Aug. 3, 2022, 10 pages.

Japanese Office Action for Application No. 2021-570381, dated Oct. 6, 2022, 6 pages including translation.

Canadian Office Action for Application No. 3141875, dated Oct. 4, 2022, 6 pages.

Chinese Office Action for Application No. 202080057061.5, dated Jan. 10, 2023, 23 pages including translation.

Notice of Allowance for Canada Patent Application No. 3,141,875, dated May 5, 2023 1 pages.

Official Action for U.S. Appl. No. 16/218,388, dated Jan. 7, 2022 7 pages Restriction Requirement.

Official Action for U.S. Appl. No. 16/218,388, dated Mar. 16, 2022 12 pages.

Official Action for U.S. Appl. No. 16/218,388, dated Jul. 15, 2022 11 pages.

Official Action for U.S. Appl. No. 16/218,388, dated Dec. 19, 2022 12 pages.

Official Action for U.S. Appl. No. 16/218,388, dated Apr. 28, 2023 12 pages.

Official Action for U.S. Appl. No. 16/218,388, dated Sep. 12, 2023 16 pages.

Official Action with English Translation for China Patent Application No. 202080057061.5, dated Jul. 27, 2023 16 pages.

English Translation of Notice of Allowance for Japan Patent Application No. 2021-570381, dated May 11, 2023 2 pages.

Intention to Grant for European Patent Application No. 20750841.7, dated Jul. 17, 2023 9 pages.

Notice of Acceptance for Australia Patent Application No. 2020290445, dated Aug. 23, 2023 3 pages.

Official Action for U.S. Appl. No. 16/2018,388, dated Mar. 19, 2024 27 pages.

Official Action with Machine Translation for China Patent Application No. 201880089070.5, dated Apr. 18, 2024 15 pages.

Extended Search Report for European Patent Application No. 23202893.6, dated Apr. 2, 2024 7 pages.

Official Action with English Translation for Japan Patent Application No. 2023-112998, dated Apr. 17, 2024 6 pages.

Official Action for European Patent Application No. 22168445.9, dated May 3, 2024 5 pages.

\* cited by examiner

The Temperature of the Three Thermistors in Different Situations — 1458

| | Not Yet Placed (1460) | Correctly Placed & Measuring (1462) | Correctly Placed, No Breath (1464) | Loose (1466) | Detached or No Breath (1468) | Operating Temperature Exceeded (1470) |
|---|---|---|---|---|---|---|
| 1st (Skin) Thermistor — 500-2 | Air | Skin | Skin | Air | Air | Skin |
| 2nd (Air) Thermistor — 500-1 | Air | Air | Air | Air | Air | Skin or Over |
| 3rd (Breath) Thermistor — 400-3 | Air | Breath | Air | Breath | Air | - |
| Breath Indicator — 1453a | No | Yes | Yes | Yes | No | - |
| Sensor — 1401 | Air | Skin | Skin | Air | Air | Skin |
| Possible Alarm | - | - | No Breath | Sensor Loose | No Breath / Sensor Detached | Operating Error |

FIG. 36

NASAL AND ORAL RESPIRATION SENSOR

CROSS-REFERENCE TO RELATED APPLICATIONS

This application is a continuation of application Ser. No. 16/438,410 filed on Jun. 11, 2019, which is a continuation-in-part of application Ser. No. 16/218,388, filed on Dec. 12, 2018, which claims the benefit of Provisional Application No. 62/597,870, filed on Dec. 12, 2017, the entirety of each of which is incorporated herein by reference for all purposes.

BACKGROUND

The present disclosure relates generally to medical sensors. More particularly, the present disclosure relates to respiration sensors for a continuous, long-lasting monitoring of an individual or patient, including measuring and analyzing respiratory condition and movement of the person.

The respiration of a person may be monitored for various reasons. For example, knowledge about a patient's respiration may assist a caregiver in assessing the patient's stability during surgery and recovery thereafter. Knowledge about a person's respiration can also assist with therapy related to sleeping.

Many approaches to respiration sensors involve cumbersome devices that can obstruct a patient's respiratory passages. In many applications, the patient is unconscious or semi-conscious and there is a challenge to fix a respiration sensor in place for an extended period of time. Accordingly, in many of the existing systems a nurse is required to frequently check the patient for sensor placement or inadvertent sensor movement. Moreover, due to the physiognomy of the human respiratory passages, many devices tend to produce confused readings relative to either of a patient's nostrils and mouth, and fail to clearly distinguish and provide differentiated data for inspiration and exhalation steps.

SUMMARY

In the field of medical care for patients with respiratory dysfunction, it is highly desirable to provide continuous, real-time measurement of the patient's respiratory cycles. In the measurement of respiratory cycles from patients, one of the challenges is to clearly distinguish between inhalation and exhalation cycles. The complication is compounded by the human physiognomy, which places nasal and oral flows (in and out of the patient) in close proximity to each other, thereby increasing the possibility of flow mix, turbulence, and stagnation in some places.

An aspect of the present disclosure provides, but is not limited to, a respiration sensor for monitoring and analysis of an individual or patient's respiratory condition and cycle, monitoring and analysis to ensure a respiration sensor is positioned as intended, detecting movement of a person using a respiration sensor, detecting and distinguishing between oral and individual nasal air flows, and integration of a respiration sensor and data with a network.

In some embodiments, the present disclosure provides a respiration sensor comprising: a housing having a nasal flow passage that extends therethrough, wherein the nasal flow passage is disposed approximately parallel with a nasal respiratory flow direction; and an electronics board comprising a nasal thermistor, the electronics board coupled to the housing such that the nasal thermistor is positioned into the nasal flow passage.

In some embodiments, a respiration sensor is disclosed, the respiration sensor comprising: a housing having a first nasal flow passage and a second nasal flow passage that extend therethrough, wherein the nasal flow passages are disposed in parallel to one another with respect to a nasal respiratory flow direction; and an electronics board comprising a first nasal thermistor and a second nasal thermistor, the electronics board coupled to the housing such that the first and second nasal thermistors are positioned into each of the first and second nasal flow passages, respectively.

In some embodiments, the present disclosure provides a respiration sensor comprising: one or more thermistors configured to detect at least one of an inspiratory temperature, an expiratory temperature, an ambient temperature adjacent the respiratory sensor, or a temperature of a patient's skin engaged against the respiratory sensor; an accelerometer configured to detect at least one of a movement of the patient, a position of the patient, a heart rate, or a respiration rate; and an electronics board coupled to the one or more thermistors and the one or more thermistors.

In some embodiments, the present disclosure provides a system, comprising: a server having a memory storing commands, and a processor configured to execute the commands to: receive, from a hub, a data indicative of a respiratory condition of a patient; transfer the data into a memory in a remote server; provide the data to a mobile computer device, upon request; and instruct the mobile computer device to graphically display the data, wherein the data comprises a temperature value from at least one of two nasal flow passages, a temperature value from an oral flow passage, a temperature value of a patient's skin surface, and a temperature value of a patient's environment.

In some embodiments of the present disclosure, a method is disclosed, the method comprising: receiving, from a hub, a data indicative of a respiratory condition of a patient; transferring the data into a memory in a remote server; providing the data to a monitor, upon request; and instructing the monitor to graphically display the data, wherein the data comprises a temperature value from at least one of two nasal flow passages, a temperature value from an oral flow passage, a temperature value of a patient's skin surface, and a temperature value of a patient's environment.

In some embodiments a respiration sensor system is disclosed, the respiration sensor system comprising: a respiration sensor comprising a housing having a nasal flow passage that extends therethrough, wherein the nasal flow passage is aligned with a nasal respiratory flow direction, and an electronics board comprising a nasal thermistor, the electronics board coupled to the housing such that the nasal thermistor is positioned into the nasal flow passage; and a hub configured to move data between the respiration sensor and a network.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings.

The illustrated embodiments are intended to illustrate, but not to limit, the inventions. The drawings contain the following figures.

FIG. 36 illustrates a respiration sensor detection state table for determining the respiration sensor placement and function, according to some embodiments.

In the figures, elements having the same or similar reference numeral have the same or similar functionality or configuration, unless expressly stated otherwise.

DETAILED DESCRIPTION

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings, and detailed description are to be regarded as illustrative in nature and not as restrictive.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. It will be apparent, however, to one ordinarily skilled in the art that the embodiments of the present disclosure may be practiced without some of these specific details. In other instances, well-known structures and components are shown in block diagram form in order to avoid obscuring the concepts of the subject technology, or have not been shown in detail so as not to obscure the disclosure. Like components are labeled with similar element numbers for ease of understanding.

In accordance with at least some embodiments disclosed herein is respiration sensor that can: monitor nasal and oral respiration gas flow; monitor patient and ambient conditions; monitor movement of the respiration sensor; distinguish between oral and nasal air flow, and between left and right nasal air flow. The respiration sensor can identify and analyze thermal transfer distinction between inhalation and exhalation gases to provide a clear pattern of the respiratory cycle.

In at least some embodiments disclosed herein, any of nasal and oral respiration gas flow, heart rate, respiration rate or cycle, and movement of the respiration sensor and patient are determined. Embodiments of the present disclosure can send and receive data related to the monitoring and analysis by the respiration sensor; indicate a patient's condition or position; and provide a signal or alarm corresponding to specific conditions. In some embodiments, wireless communication techniques are utilized to provide ubiquitous solutions for respiratory sensing of patients in hospitals, treatment facilities, home-care situations, and the like.

I. Embodiments of Respiratory Sensors

Figure 1:
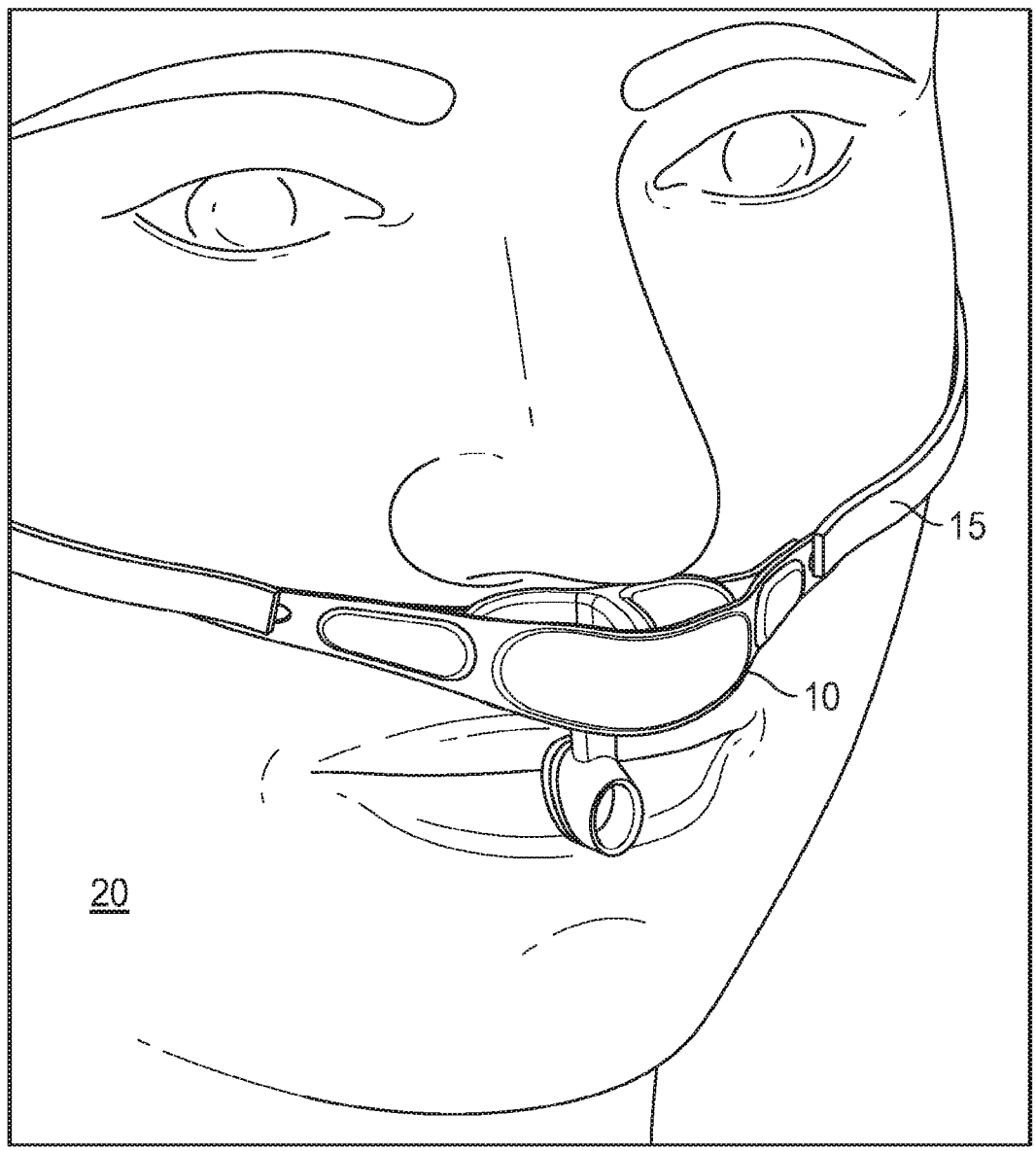
FIG. 1 illustrates a front perspective view of a respiration sensor placed on a patient's head, according to some embodiments.

FIG. 1 illustrates a respiration sensor 10 placed on a patient's head 20, according to some embodiments. The respiration sensor 10 is positioned on patient's face between the mouth and nose to measure nasal and oral breathing gas flow. The gas flow measurement is based on measuring temperature differences between inspiratory and expiratory gas flows. Patient's skin and ambient air temperatures can also be measured to verify that the respiration sensor 10 is placed appropriately against the patient. Some embodiments, later described, include other sensors, such as capacitive sensors or detectors and accelerometers to ensure that respiration sensor 10 has not fallen out of place, and that respiration sensor 10 is making proper contact with the patient's physiognomy. A securement string or strap 15 helps maintain the position of respiration sensor 10 relative to the patient's physiognomy.

Figure 2A:
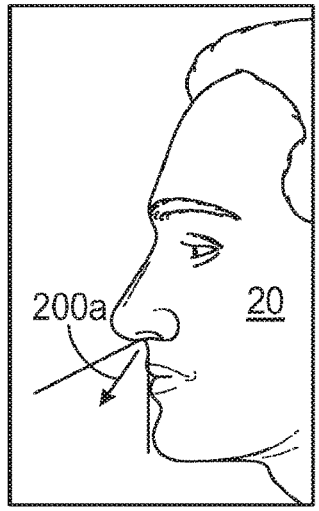
FIG. 2A illustrates a side plan view of a gas flow exiting from a patient's nasal cavity, according to some embodiments.
Figure 2B:
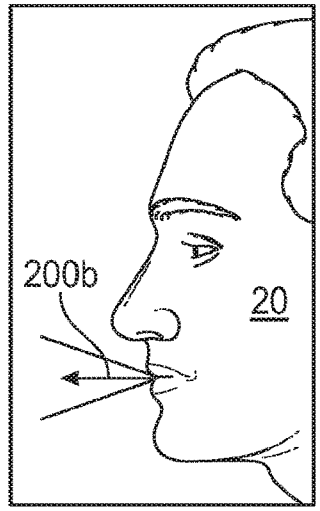
FIG. 2B illustrates a side plan view of a gas flow exiting from a patient's oral cavity, according to some embodiments.
Figure 3:
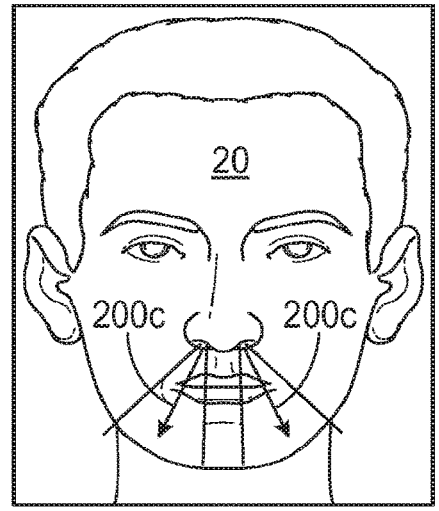
FIG. 3 illustrates a front plan view of a gas flow exiting from a patient's nasal cavity, according to some embodiments.

FIGS. 2A and 3 illustrate regions 200a, 200c for a gas flow exiting from a patient's nasal cavities, and FIG. 2B illustrates regions 200b for a gas flow exiting from a patient's oral cavity, according to some embodiments. Experiments show that breathing gas flow exits nasal and oral cavities in different regions between different subjects. Accordingly, embodiments of a respiration sensor as disclosed herein include a geometry that may separate each of the different flows through the regions 200a, 200b, 200c to provide a more accurate measure of the respiratory cycles of a patient. Accordingly, a precise determination of the positioning of the respiration sensor 100a, 100b relative to the patient's face is highly desirable.

Figure 4:
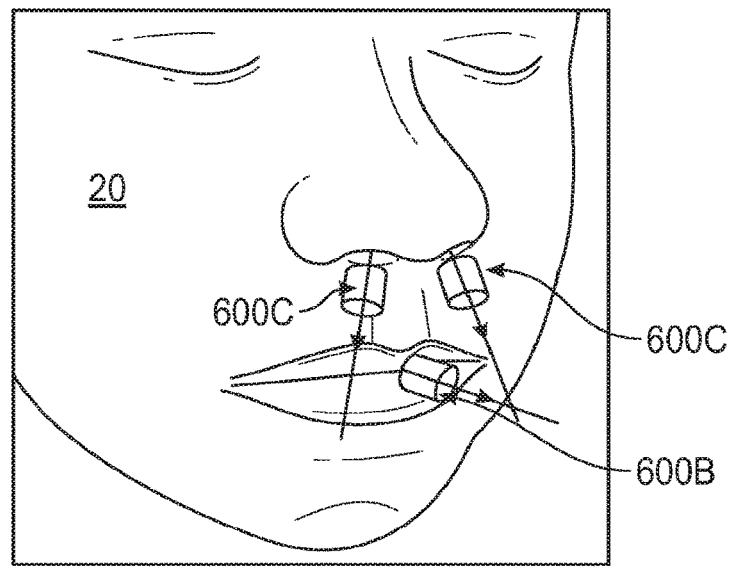
FIG. 4 illustrates a front perspective view of nasal respiration flows and oral respiration flows in a patient, according to some embodiments.

FIG. 4 illustrates a portion of nasal respiration flow 600C and oral respiration flow 600B for a patient 20, according to some embodiments. Sensor cavities of the respiration sensor capture nasal and oral breathing gas flow from the patient. The sensor cavities are positioned parallel to the average direction of that specific flow to maintain flow as laminar as possible inside the cavity. Thus, nasal sensor cavities are positioned parallel to each other between the nose and mouth, but also parallel to upper lip. More advantageously, nasal sensor cavities slightly diverge past the middle part of the mouth and upper lip into the average direction of nasal breathing gas flows. An oral sensor cavity is positioned transverse to the nasal cavities, outwards from the mouth. In some embodiments, the oral sensor cavity and the nasal sensor cavities are positioned relative to each other so that a direction of oral respiration flow 600B through the oral cavity is transverse relative to a direction of nasal respiration flow 600C through any of the nasal sensor cavities. Sensor cavities are also smooth and straight, or more advantageously slightly tapered, to capture flow from a larger area, since any turn or sudden change in the cross-section of cavity along the flow path generate turbulences that mix inspiratory and expiratory air flow phases degrading the measurement speed, accuracy and response time.

Figure 5:
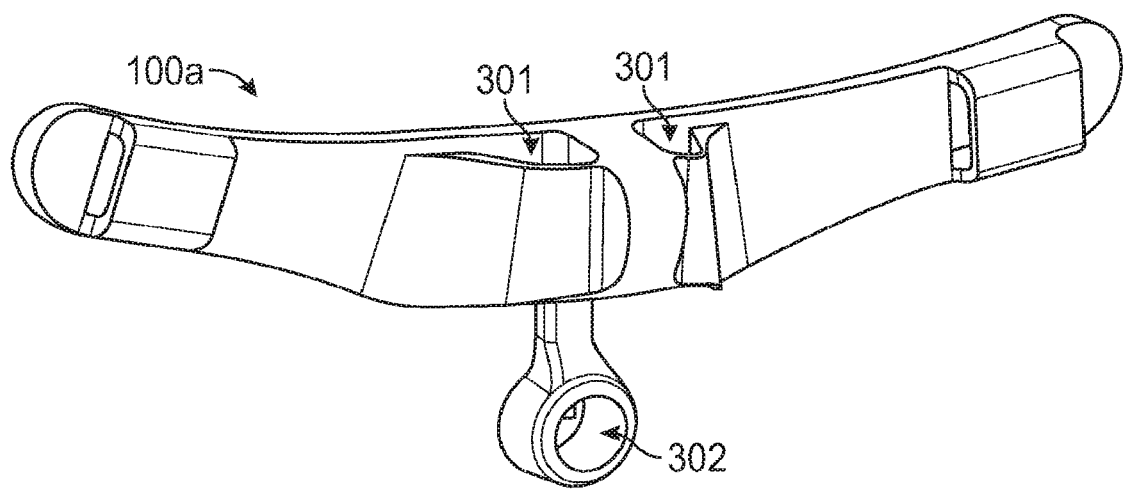
FIG. 5 illustrates a front perspective view of a respiration sensor including nasal flow passages and oral flow passages, according to some embodiments.

FIG. 5 illustrates a respiration sensor 100a, for example, including nasal flow passages 301 and an oral flow passage 302. The nasal respiration flow exiting a patient's nasal cavity, e.g., gas flow regions 200a, 200c, can be captured and guided by a nasal passage 301 parallel to average direction of nasal respiration flow 600C. Similarly, the oral respiration flow exiting a patient's mouth, e.g., gas flow region 200b, can be captured and guided by the oral cavity 302 parallel to direction of the oral respiration flow 600B. By providing a sensing element inside of each of the different flow passages 301 and 302, the respiration sensor 100a may accurately determine a respiration flow before the nasal flow and the oral flows are mixed together adjacent the patient's upper lip.

Figure 6:
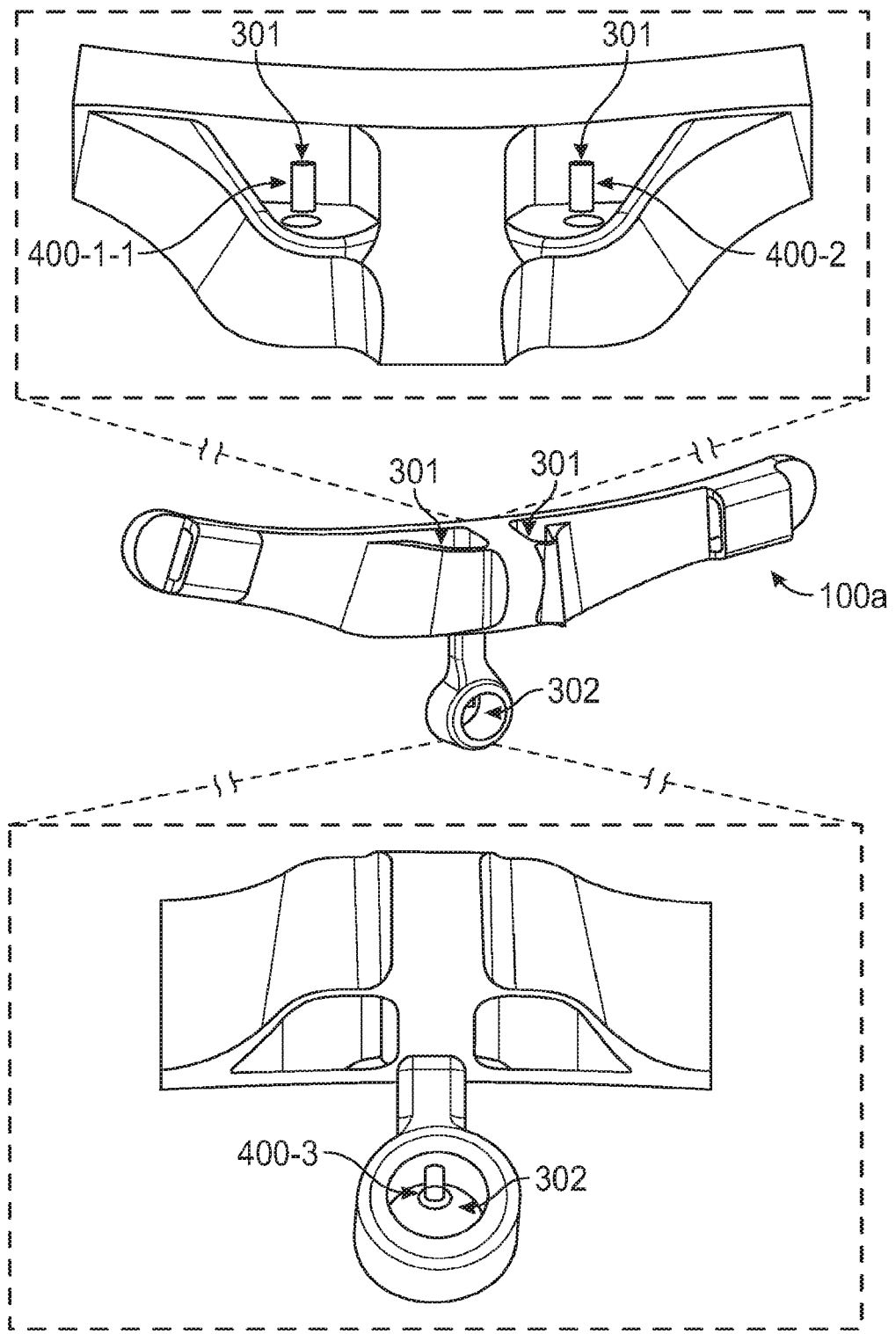
FIG. 6 illustrates perspective detail views of nasal flow passages and oral flow passages of a respiration sensor, according to some embodiments.

FIG. 6 illustrates the respiration sensor 100a, with portions thereof shown in detail views, including detail views of the nasal flow passages 301 and the oral flow passage 302. The respiration sensor 100a includes thermistors 400-1, 400-2, 400-3 for sensing inhalation and exhalation flows. A nasal respiratory flow of a patient can be captured by the nasal passages 301 and measured with a first and second nasal thermistors 400-1, 400-2 therein. An oral respiratory flow of the patient can be captured by the oral cavity 302 and measured with thermistor 400-3 therein. The resistance of each thermistor changes proportionally to flowing gas heating or cooling down the thermistor, e.g., during inspiration and expiration.

Moreover, the nasal flow passages 301 are separated from each other such that nasal thermistors 400-1 and 400-2 may separately identify and measure the respiration flow associated with each of the patient's nostrils. By separately identifying respiration flow associated with each of the patient's nostrils, potential respiratory conditions or patient's positions can be determined. For example, a blockage of a nasal passage or the respiration device can be identified and corrected.

In some embodiments, oral thermistor 400-3 is placed on a plane that is transverse or substantially perpendicular to nasal thermistors 400-1, 400-2. This geometry also enables an accurate and independent measurement between each of the thermistors 400-1, 400-2, 400-3, avoiding any mixing or turbulent area.

Figure 7:
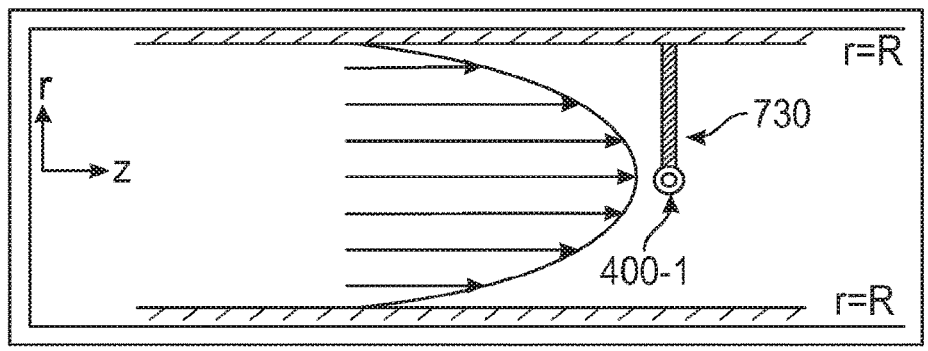
FIG. 7 illustrates a cross-sectional view of a laminar respiration flow relative to a thermistor in a respiration sensor, according to some embodiments.
Figure 8:
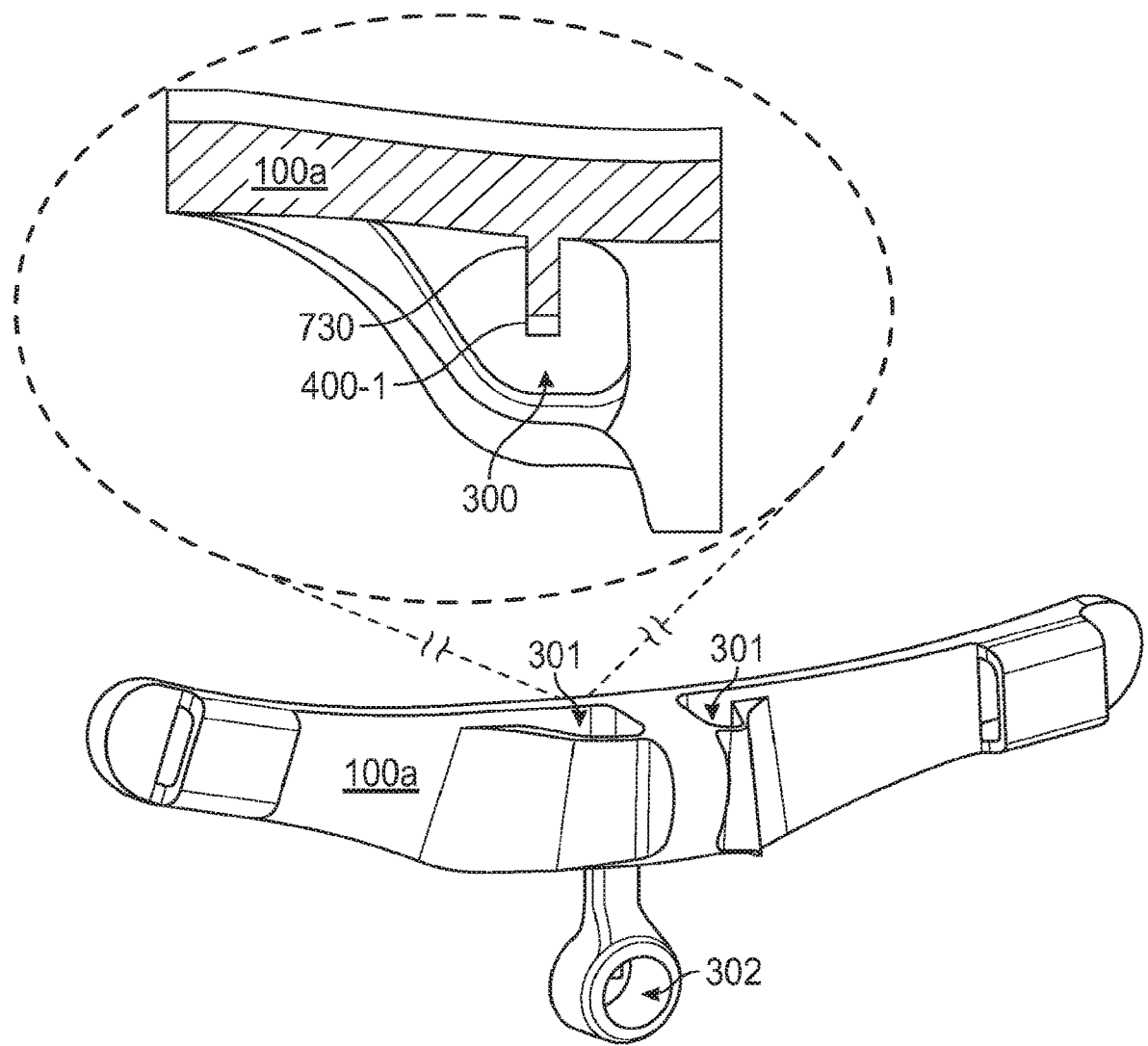
FIG. 8 illustrates a schematic view of a flow passage of a respiration sensor, according to some embodiments.

Referring to FIGS. 7 and 8, the thermistors 400-1, 400-2, 400-3 can be located approximately in the middle of its corresponding sensor cavity to maximize accuracy and sensitivity to gas flows. To position the thermistor 400-1, 400-2, 400-3 in the middle of a corresponding sensor cavity, the thermistor 400-1, 400-2, 400-3 is coupled to a tip portion of a thin support structure 730. The support structure can have a proximal portion coupled to an electronics board and a distal portion transverse to a plane defined by the top of the electronics board, wherein the distal portion of the support structure extends into a nasal flow passage. In some embodiments, the respiration sensor 100a has a structure and geometry that separates the nasal flow from each nostril separately, to provide a more accurate and detailed picture of the patient's respiratory condition.

FIG. 7 illustrates a cross-section of a laminar respiration flow of a patient through a sensor cavity. Laminar flow speed distribution in a tube is parabolic, thus the speed is maximum at a point approximately in the middle of the tube. The respiration flow is illustrated relative to thermistor 400-1 of a respiration sensor 100a, however, the present disclosure can apply to any thermistor 400-1, 400-2, 400-3. By placing thermistor 400-1 as close as possible to the middle of the flow cavity in the respiration sensor 100a, for example, a more accurate measurement is expected, as the velocity of the gas flow is highest at the center of the flow cavity. Accordingly, it is expected that a temperature differential between inhalation and exhalation be highest at the middle point of the flow cavity. Moreover, the convection or radiated thermal energy from surrounding structures is minimized when a thermistor 400-1, 400-2, 400-3 is located into the middle of cavity by a support structure 730.

FIG. 8 illustrates the respiration sensor 100*a*, with a portion thereof shown in a cross-sectional detail view. The cross-sectional view illustrates a support structure 730 extending into the nasal flow passage 301, and the thermistor 400-1 positioned at a distal end portion of the support structure 730. It should be understood that the present disclosure, including support structures, can apply to any of the thermistors 400-1, 400-2, 400-3 and flow passages 301, 302.

The support structure 730 extends from a portion of the respiration sensor 100*a* into the nasal flow passage 301. It should be understood that the support structure 730 can extend partially into a flow passage 301, 302. For example, the support structure 730 can extend into a mid-portion of at least one of the two nasal flow passages 301. In some embodiments of the present disclosure, the support structure 730 extends beyond or across the respective flow passage 301, 302. The support structure 730 can comprise a cantilevered structure that extends into a respective flow passage 301, 302. However, in some embodiments, the support structure 730 can comprise an arch structure partially extending away from an inner surface of the flow passage 301, 302 toward the thermistor 400-1, and partially extending from the thermistor 400-1 toward the inner surface of the flow cavity. In some embodiments, the support structure 730 and the thermistor 400-1 can extend across inner surfaces of the flow cavity.

The respiration sensor 100*a* includes walls having an inner surface forming the sensor cavities. The walls of the cavity extend around at least a portion of the thermistors 400-1, 400-2, 400-3. The walls protect the sensitive thermistors 400-1, 400-2, 400-3 from various disturbing ambient gas flows causing error to measured breathing gas flow signal, for example, a caregiver being able to touch or breathe into thermistors or air conditioning in proximity to the thermistor 400-1, 400-2, 400-3. In addition, the walls forming the cavities also protect small, mechanically sensitive thermistors from various mechanical forces, stresses, and shocks, such as touching etc.

Figure 9A:
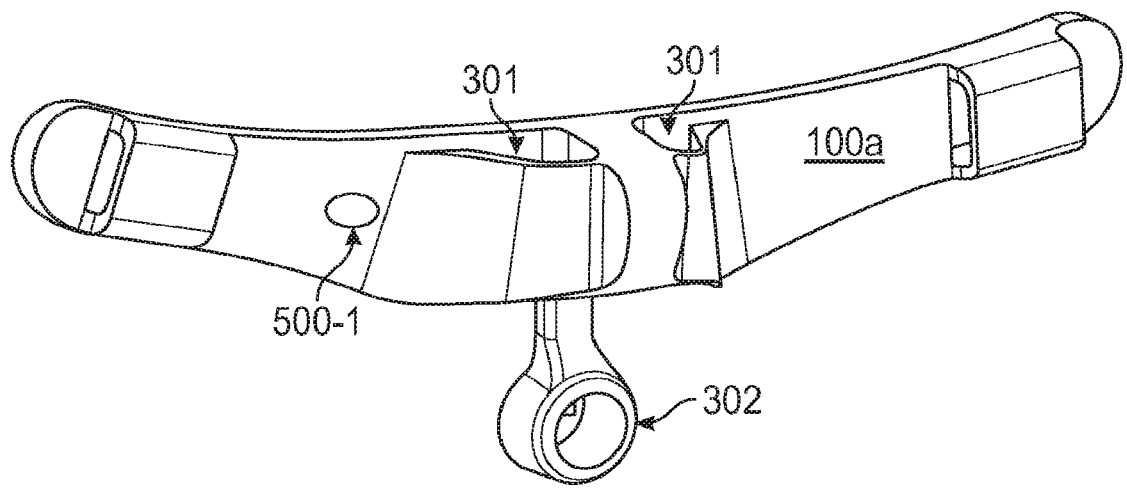
FIGS. 9A and 9B illustrate front and back perspective views of a respiration sensor, according to some embodiments.
Figure 9B:
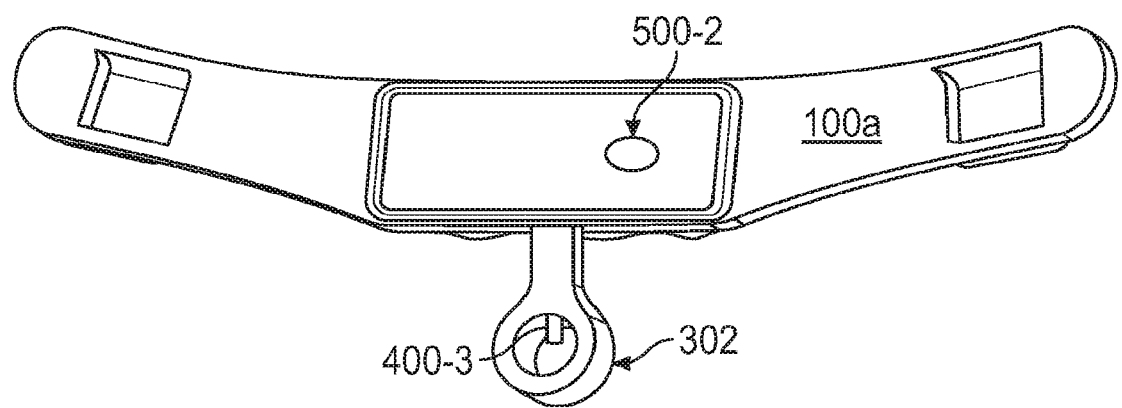

FIGS. 9A and 9B illustrate the respiration sensor 100*a*, for example, including thermistors 500-1, 500-2 for sensing the positioning of the sensor relative to a patient's physiognomy, according to some embodiments. An ambient thermistor 500-1 can be positioned along a front side of the respiration sensor 100*a*, adjacent a portion of the respiration sensor 100*a* that faces away from the patient when the respiration sensor 100*a* is worn by a patient. Similarly, a skin thermistor 500-2 can be positioned along a back side of the respiration sensor 100*a*, adjacent a portion of the respiration sensor 100*a* that faces toward the patient when the respiration sensor 100*a* is worn by a patient. In some embodiments, when the respiration sensor 100*a* is worn by a patient, the thermistor 500-1 is distal to the patient's face, and the thermistor 500-2 is proximal to the patient's upper lip and engaged against the patient's skin.

The respiration sensor 100*a* can include a passage or cavity along any of the front side or the back side thereof. The thermistor 500-1 can be positioned in a cavity along the front side of the respiration sensor 100*a* to measure ambient air temperature. The thermistor 500-2 can be positioned in a cavity along the back side of the respiration sensor 100*a* to measure the temperature of patient's skin.

In some instances, thermistor 500-2 can detect when the sensor 100*a* is properly positioned on the patient while thermistor 500-1 can detect the temperature of ambient air. Comparison of temperatures from 500-1 and 500-2 can be used to indicate a patient condition or proper positioning and function of the sensor 100*a*, for example. In some embodiments, when thermistors 500-1 and 500-2 detect the same temperature, it may be assumed that respiration sensor 100*a* is likely not attached to the patient, or that the patient's temperature is the same as the ambient temperature, which may indicate a hazardous health condition.

Figure 10:
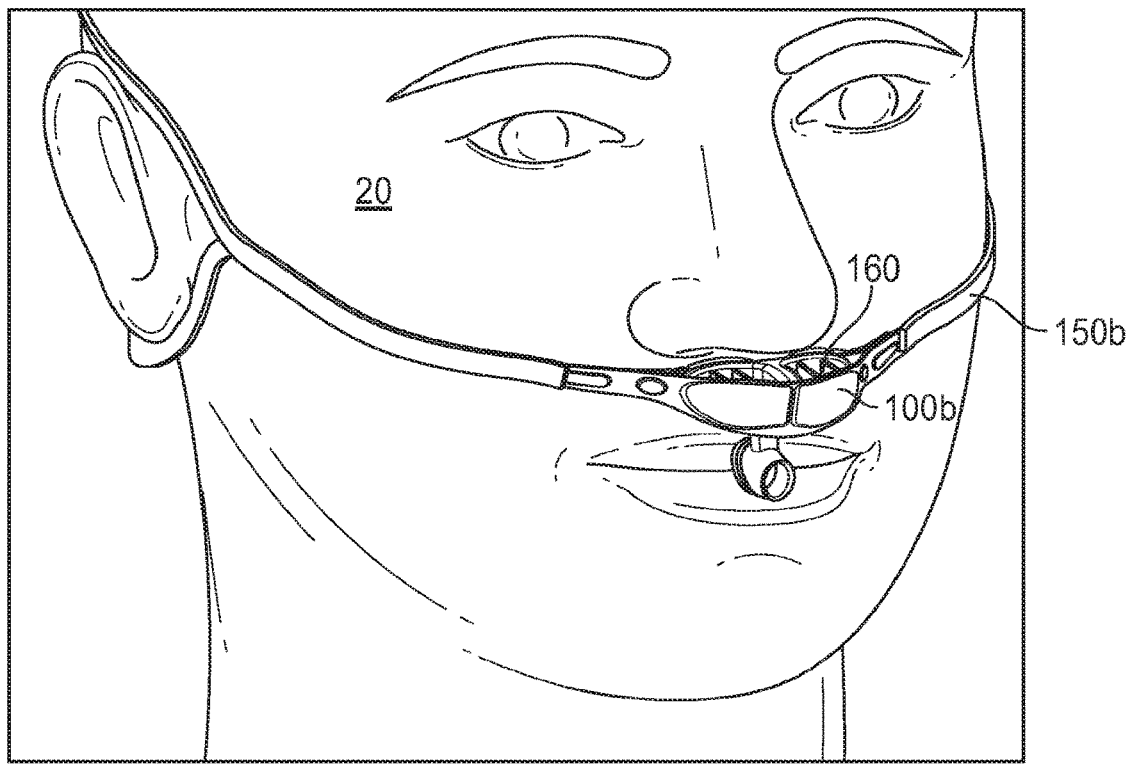
FIG. 10 illustrates a front perspective view of a respiration sensor placed on a patient's head, according to some embodiments.

FIG. 10 illustrates another embodiment of a respiration sensor 100*b*, which is substantially similar to respiration sensor 100*a*. Respiration sensor 100*b* is also placed on a patient's face between the mouth and nose to measure nasal and oral breathing gas flows. Much like the respiration sensor 100*a*, the measurement is based on measuring temperature differences between inspiratory and expiratory gas flows. The patient's skin temperature and the ambient air temperature can also be measured to verify or detect that the respiration sensor 100*b* is placed appropriately with respect to the patient's nasal and oral breathing gas flows and to the patient's upper lip.

Some embodiments described herein include other sensors, such as capacitive detectors or sensors to detect whether the respiration sensor 100*b* is making proper contact with the patient's physiognomy and accelerometers to detect movement and position of the respiration sensor 100*b* to ensure, for example, that the respiration sensor 100*b* has not fallen out of place, that the patient has not fallen down, or that the orientation of the patient's head is not obstructing the nasal and oral breathing gas flows (e.g., patient's face is downward towards pillow or bed).

A string or strap 150*b* helps maintain the position of the respiration sensor 100*b* relative to the patient's physiognomy. According to some embodiments, the respiration sensor 100*b* can include a nasal flow guide 160 to concentrate and provide laminar inspiratory and expiratory gas flows through the respiration sensor 100*b*.

Figure 11:
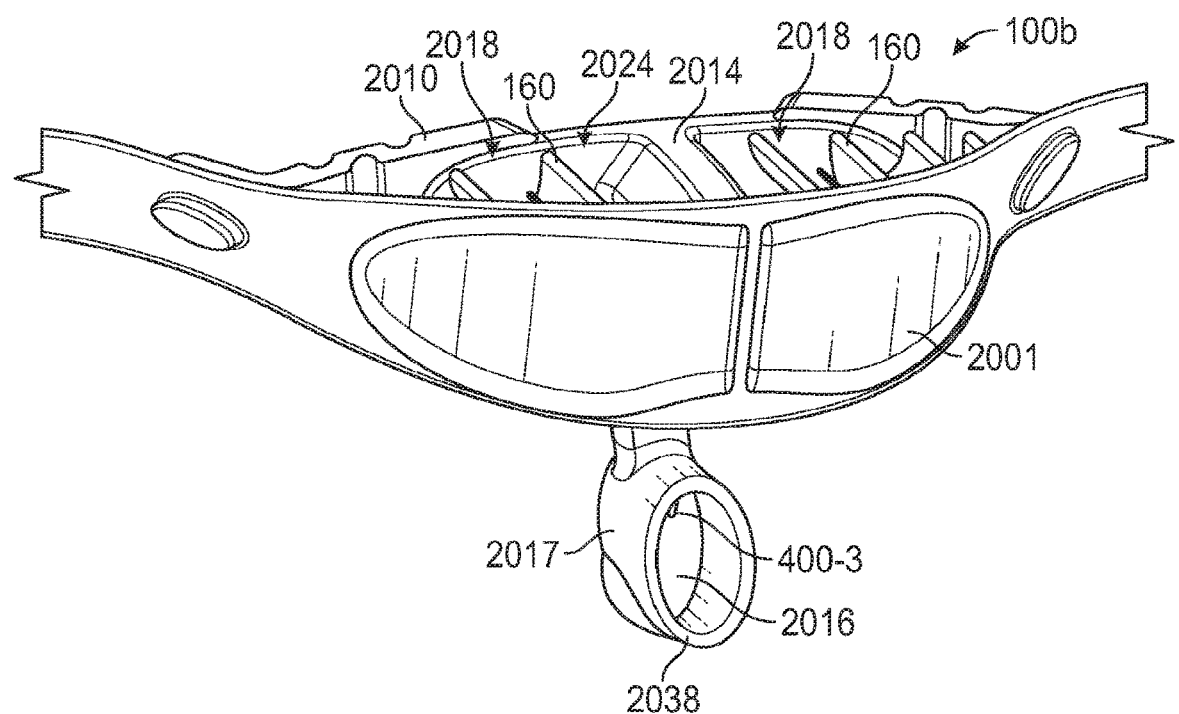
FIG. 11 illustrates a front perspective view of a respiration sensor, according to some embodiments.
Figure 12:
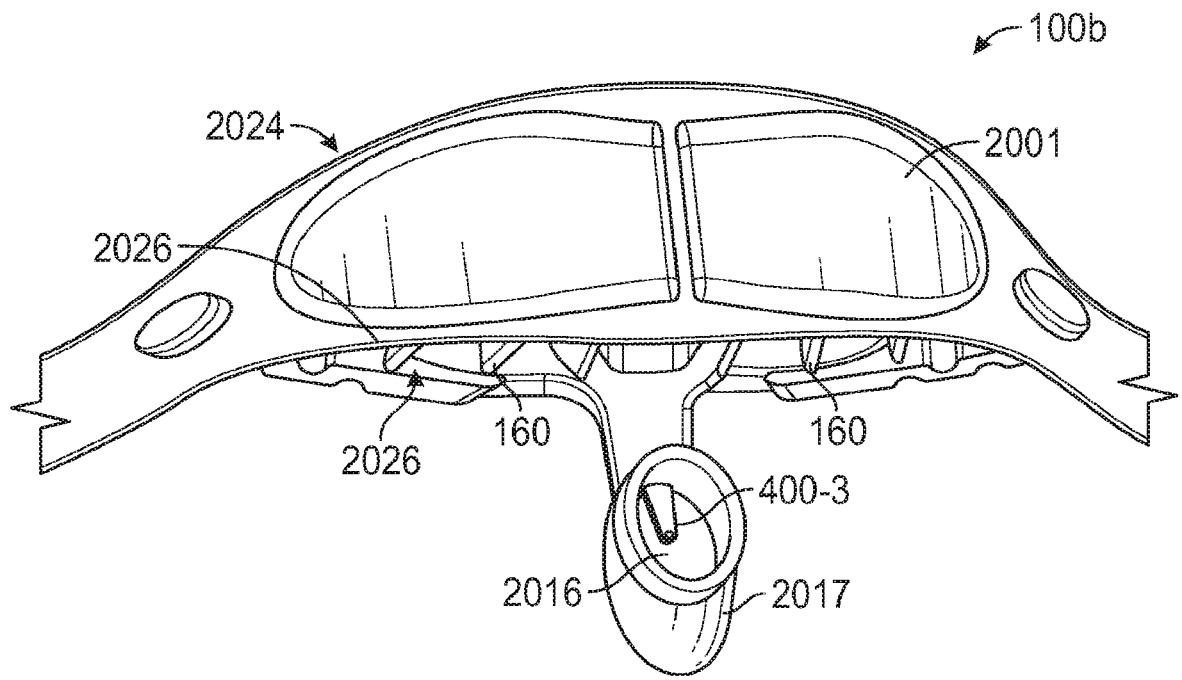
FIG. 12 illustrates a bottom perspective view of the respiration sensor of FIG. 11.

FIGS. 11 and 12 illustrate the respiration sensor 100*b* having a housing 2001, a base 2010, and a shroud 2012. The shroud 2012 is positioned between the housing 2001 and the base 2010 to form at least a portion of a cavity. The respiration sensor 100*b* includes nasal flow passages 2018, which are similar to nasal flow passages 301, and an oral flow passage 2016, which is similar to oral flow passages 302 of respiration sensor 100*a*. The nasal flow passages 2018 extend from a top portion to a bottom portion of the respiration sensor 100*b*. In use, a nasal respiration flow from a patient's nose can move between the nasal inlet 2024 and the nasal outlet 2026 of each of the nasal flow passages 2018. The nasal inlet 2024 of each of the nasal flow passages 2018 is where the breathing gas flows into the respiration sensor 100*b* during expiration. The nasal outlet 2026 of each of the nasal flow passages 2018 is where the ambient air flows into the respiration sensor 100*b* during inspiration.

The shroud 2012 includes a battery frame 2014, which extends away from a front surface of the shroud 2012. The battery frame 2014 encloses a battery, securing it to the base 2010 and divides the area between the shroud 2012 and the housing 2001 into two distinct nasal flow passages 2018, such that the nasal thermistor 400-1 is centrally disposed in one of the nasal flow passages 2018 and the nasal thermistor 400-2 is centrally disposed in the other one of the nasal flow passages 2018. The battery frame 2014 is disposed substantially centrally on the respiration sensor 100*b* and is arranged to be positioned under the septum of a patient's nose when the respiration sensor 100*b* is placed on or attached adjacent to the upper lip of the patient.

Housing 2001 can be made of a paper battery engineered to use a spacer formed largely of cellulose that makes paper batteries flexible and environmentally-friendly. The functioning is similar to conventional chemical batteries with the important difference that they are non-corrosive and do not require extensive housing, but can function as housing.

An oral shroud 2017 extends from the shroud 2012, and includes a passage through a distal portion thereof. The passage forms an oral flow passage 2016 having a thermistor 400-3 positioned therein. The oral flow passage 2016 is arranged such that the oral thermistor 400-3 is centrally disposed within the oral flow passage 2016. In use, an oral respiration flow from a patient's mouth can move between the oral inlet 3036 and the oral outlet 2038.

Figure 13:
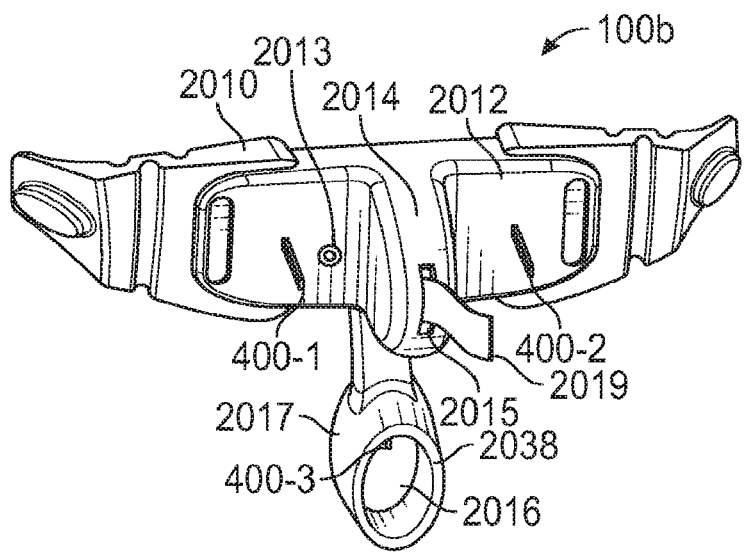
FIG. 13 illustrates a front perspective detail view of a respiration sensor, according to some embodiments.

FIG. 13 illustrates an embodiment the respiration sensor 100b, showing the base 2010 and the shroud 2012, with the housing 2001 omitted for clarity. The shroud 2012 encloses an electronics board, securing it to the base 2010. The thermistors 400-1, extend from the electronics board through the shroud 2012. The thermistors 400-1, 400-2 are oriented such that a distal portion of the thermistors 400-1, 400-2 extend into a space forming the nasal cavities 1301 when the shroud 2012 and the housing 2001 are coupled together.

The respiration sensor 100b can include a light-emitting diode (LED) 2013, which is visible through the shroud 2012. The LED 2013 can provide a confirmation or an indication of status. For example, the LED 2013 can indicate when the respiration sensor 100b is paired with another device. In some embodiments, the LED 2013 can indicate any of a charged or low battery, an indication that the respiration sensor 100b is functioning as intended, or an indication that there is a detected problem with the respiration sensor 100b. The LED 2013 can be used to indicate the location of the patient for example in hospital PACU where there are many patients, respiration sensors and monitoring devices in the same room. The LED 2013 can be turned on or display a series of blinks from the monitoring device to indicate the location of the patient and the connected respiration sensor. This may be important to ensure that a caregiver is looking at the correct monitoring device connected to patient and the respiration sensor. It should be understood that any embodiment of the respiration sensor, such as respiration sensor 100a, 100b, can include an LED 2013.

In some embodiments, a spacer 2019 can be positioned between the battery and a battery contact. The spacer 2019 can maintain the battery contact spaced apart from the battery, thereby preventing electrical conduction therebetween. The spacer 2019 can prevent discharge of the battery before the respiration sensor 100b is intended to be used. When the respiration sensor 100b is intended to be used, the spacer 2019 can be removed or separated from the respiration sensor 100b. In some embodiments, the respiration sensor 100b can comprise an opening or passage 2015 that extends between the battery and an outer surface of the housing 2001 or the shroud 2012. The spacer 2019 can be moved through the passage 2015 to separate the spacer 2019 from the respiration sensor 100b. In some embodiments, the spacer 2019 may comprise a plastic material in the form or a strip or tape.

Figure 14:
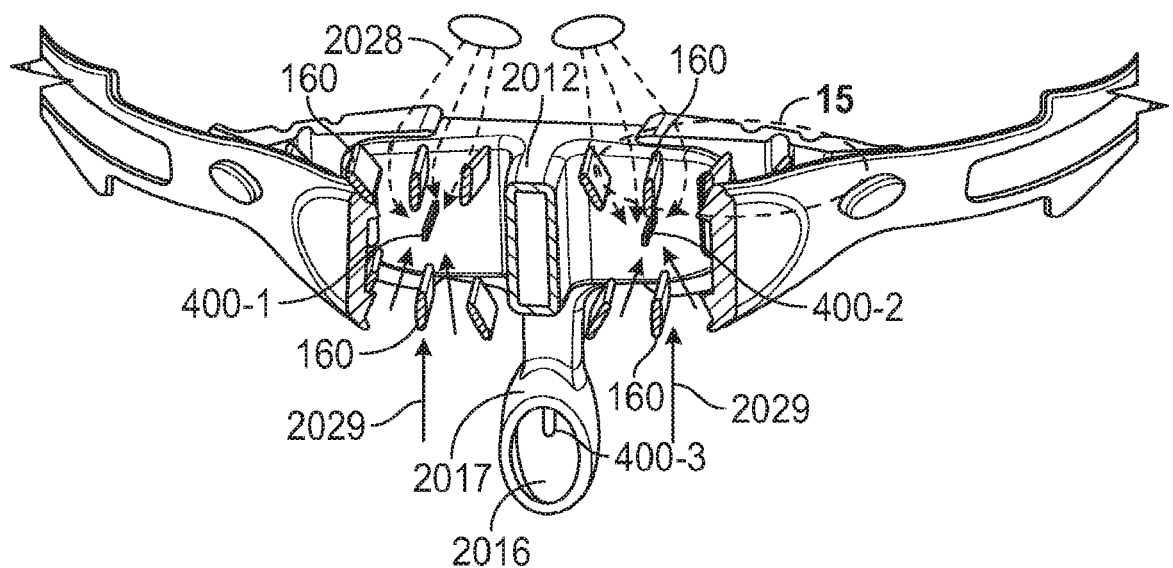
FIG. 14 illustrates a front perspective cross-sectional view of the respiration sensor of FIG. 11.

FIG. 14 illustrates an embodiment the respiration sensor 100b, showing the base 2010, the shroud 2012, and the flow guides 160, with a portion of the housing 2001 and other features omitted for clarity. At least one nasal flow guide 160 is disposed in each of the nasal flow passages 2018 and extends between the shroud 2012 and the housing 2001, as shown in at least FIGS. 11 and 12.

In some embodiments, at least one nasal flow guide 160 is disposed proximate a nasal inlet 2024 of each of the nasal flow passages 2018 and at least one nasal flow guide 160 is disposed within each of the nasal flow passages 2018. A nasal flow guide 160 can be positioned in a nasal flow passage, proximate any of the nasal inlet 2024 and the nasal outlet 2026. The nasal flow guide 160 is aligned relative to the nasal thermistor 400-1 or 400-2 to direct a flow of gas toward relative to the nasal thermistor 400-1 or 400-2.

Figure 15:
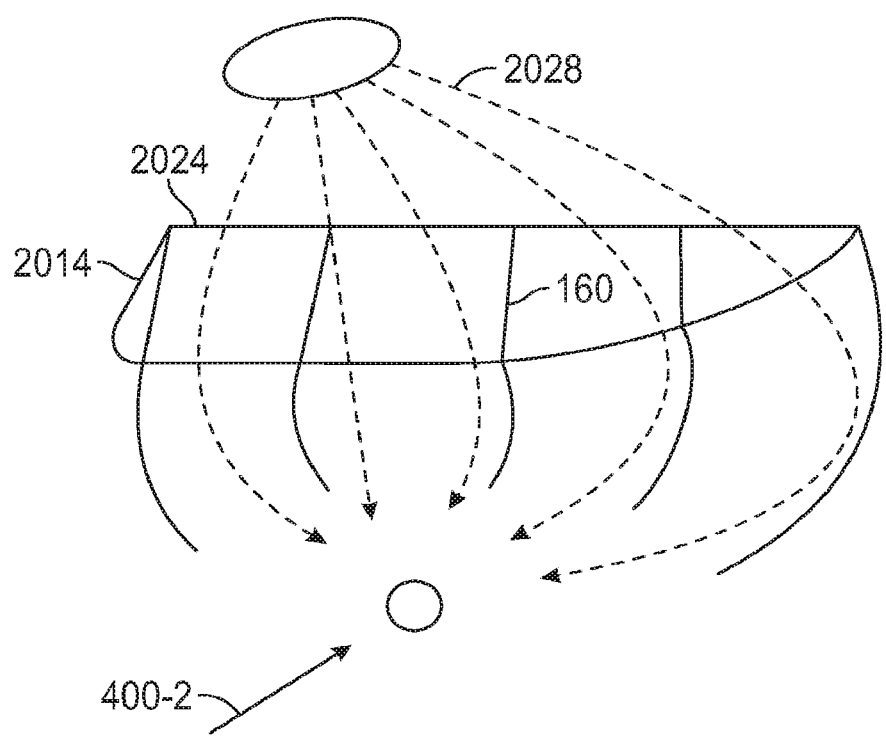
FIG. 15 illustrates a schematic view of a nasal respiration flow and a nasal flow guide, according to some embodiments.

FIGS. 14 and 15 illustrates flow of gases relative to the respiration sensor 100b, a patient's nares, and the ambient environment. Arrows 2028 illustrate a portion of nasal respiration flow from a patient's nares toward the nasal thermistor 400-1, 400-2 during expiration, and arrows 2029 illustrate a portion of ambient gas directed from the ambient environment toward the nasal thermistor 400-1, 400-2 during inspiration.

In more detail, during expiration, the at least one nasal flow guide 160, disposed proximate the nasal inlet 2024 guides the breathing gas flow through the nasal flow passages 2018 of the respiration sensor 100b and concentrates the breathing gas flow toward each of the nasal thermistors 400-1, 400-2 while maintaining the breathing gas flow laminar as it passes each of the nasal thermistors 400-1, 400-2 to minimize turbulent noise. Similarly, during inspiration, the at least one nasal flow guide 160 disposed proximate the nasal outlet 2026 guides the ambient air flow through the nasal flow passages 2018 of the respiration sensor 100b and concentrates the ambient air flow toward each of the nasal thermistors 400-1, 400-2 while maintaining the ambient air flow laminar as it passes each of the nasal thermistors 400-1, 400-2 to minimize turbulent noise.

The at least one nasal flow guide 160 can prevent undesired objects from entering the nasal flow passages 2018 and disturbing or breaking the nasal thermistors 400-1, 400-2 and/or their associated support structures. The at least one nasal flow guide 160 can also form an air gap around the nasal thermistors 400-1, 400-2 with respect to the housing 2001 and the at least one nasal flow guide 160, which prevents electro static discharge (ESD) from entering the electronics board 300 via the nasal thermistors 400-1, 400-2 and their associated support structures.

In some embodiments, the at least one nasal flow guide 160 includes a thickness that is less than 1 mm and a height that is more than 2 mm. In some embodiments, two or four nasal flow guides 160 are disposed within each of the nasal flow passages 2018 proximate the nasal inlet 2024 and/or two or four nasal flow guides are disposed within each of the nasal flow passages 2018 proximate the nasal outlet 2026. In some embodiments, the number of nasal flow guides 160 does not exceed five to allow for proper gas flow through the nasal flow passages 2018.

Figure 16:
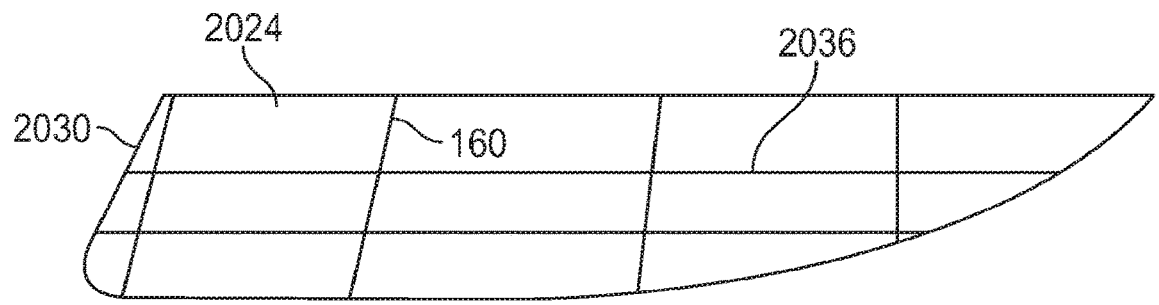
FIG. 16 illustrates a schematic view of a nasal flow guide, according to some embodiments.

FIG. 16 illustrates a schematic view of a nasal respiration flow guide grid 2030. The flow guide grid 2030 can function similarly to flow guide 160, wherein a flow of gas through a cavity of the respiration sensor 100b is directed by the flow guide grid 2030. The flow guide grid 2030 can have walls which intersect and are transverse relative to each other. In some embodiments, a flow guide grid 2030 is disposed proximate the nasal inlet 2024 and a flow guide grid 2030 is disposed proximate the nasal outlet 2026 of each nasal cavity of the nasal flow passages 2018.

Figure 17:
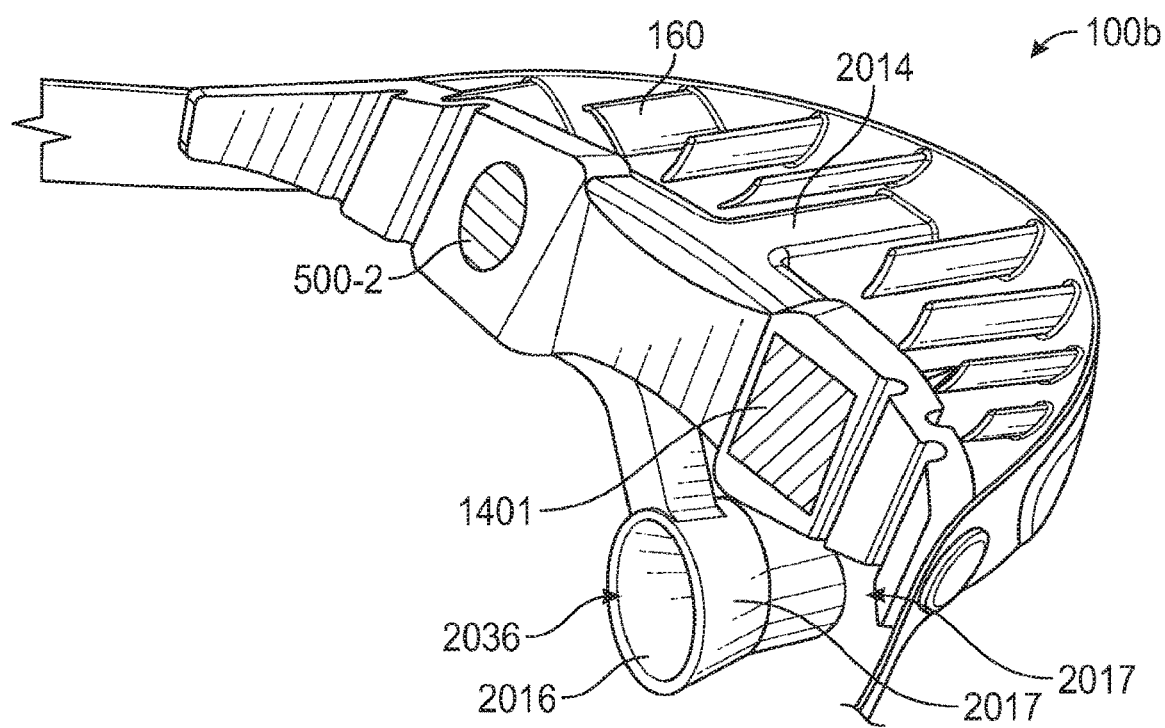
FIG. 17 illustrates a back perspective view of a respiration sensor, according to some embodiments.

Additional sensors of a respiration sensor 100b are illustrated in the back, perspective view of the respiration sensor 100b in FIG. 17. The respiration sensor 100b includes a thermistor 500-2 and a sensor 1401 located on the back portion of the respiration sensor 100b. The thermistor 500-2 can provide temperature information regarding the patient or an ambient environment adjacent to the back portion of the respiration sensor 100b. The sensor 1401 is a capacitive plate, which can engage against the patient. The sensor 1401 can engage against a region between a patient's upper lip and nose, e.g., an area including the philtrum, and provide information to determine a location of the respiration sensor 100b relative to the patient's face.

II. Gas Flow Through Respiration Sensors

Figure 18:
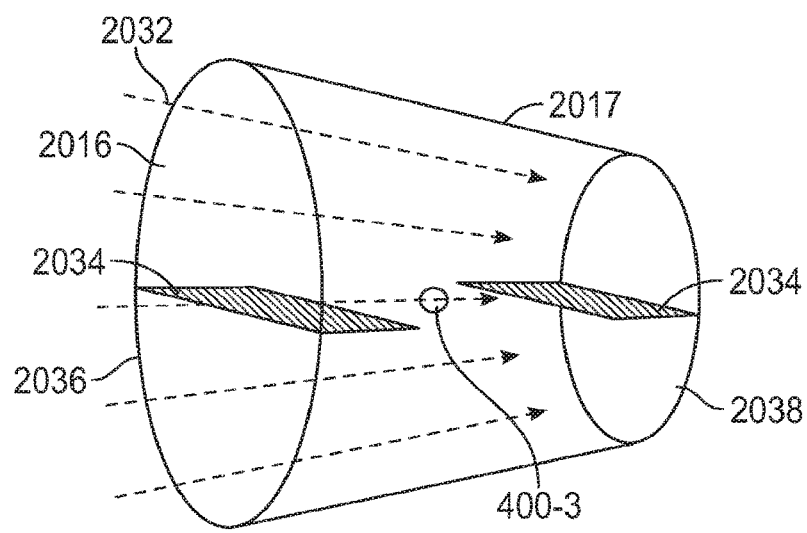
FIG. 18 illustrates a schematic view of a respiration flow through a cavity of a respiration sensor, according to some embodiments.

Referring to FIGS. 17 and 18, an oral shroud 2017 of the respiration sensor 100b can have a cross-sectional area that tapers along a portion thereof or relative to an oral inlet 2036 and an oral outlet 2038. The oral inlet 2036 is where the breathing gas flows into the oral flow passage 2016 of the respiration sensor during expiration, and the oral outlet 2038 is where the ambient air flows into the oral flow passage 2016 of the respiration sensor during inspiration.

In some embodiments, as illustrated in FIG. 17, a cross-sectional area of the oral shroud 2017 forms an hourglass shape. For example, a cross-sectional area of the oral shroud 2017 can taper from the oral inlet 2036 toward the oral thermistor 400-3, positioned between the oral inlet 2036 and the oral outlet 2038, and can taper away from the oral thermistor 400-3 toward the oral outlet 2038. In some embodiments, as illustrated in FIG. 18, the cross-sectional area of the oral shroud 2017 can taper from the oral inlet 2036 toward the oral outlet 2038. The cross-sectional area of the oral shroud 2017 can also taper from the oral outlet 2038 toward the oral inlet 2036.

In some aspects, the oral shroud 2017 can have a cross-sectional profile transverse to a flow through the oral shroud 2017. The cross-sectional profile of oral shroud 2017 can be any regular or irregular shape, such as an oval, circle, square, or rectangle.

FIG. 18 illustrates a detail schematic view of the oral shroud 2017, including an oral flow guide 2034. The oral flow passage 2016 of the oral shroud 2017 collects the breathing gas flow ejected from a patient's mouth. The cross-sectional area of the oral shroud 2017 tapers from the oral inlet 2036 toward the oral thermistor 400-3, and from the oral thermistor 400-3 toward the oral outlet 2038. Alternatively, in some embodiments, the cross-sectional area of the oral shroud 2017 can taper from the oral outlet 2038 to the oral inlet 2036.

The oral flow guide 2034 can direct at least portion of oral respiration flow 2032 moving through the oral flow passage 2016 of the oral shroud 2017. An oral flow guide 2034 is disposed proximate an oral inlet 2036 of the oral shroud 2017 and an oral flow guide 2034 is disposed proximate an oral outlet 2038 of the oral shroud 2017.

During expiration, the oral flow guide 2034 disposed proximate the oral inlet 2036 guides the breathing gas flow through the oral flow passage 2016 and concentrates the breathing gas flow toward the oral thermistor 400-3 while maintaining the breathing gas flow laminar as it passes the oral thermistors 400-3 to minimize turbulent noise. Similarly, during inspiration, the oral flow guide 2034 disposed proximate the oral outlet 2038 guides the ambient air flow through the oral flow passage 2016 of the respiration sensor and concentrates the ambient air flow toward the oral thermistor 400-3 while maintaining the ambient air flow laminar as it passes the oral thermistor 400-3 to minimize turbulent noise.

The oral flow guide 2034 extends from the oral shroud 2017 within the oral flow passage 2016. The oral flow guide 2034 can extend radially inward from an inner surface of the oral shroud 2017. The oral flow guide 2034 can extend across a portion of the oral flow passage 2016, or across the oral flow passage 2016 to engage against an opposite inner surface of the oral shroud 2017. In some embodiments, the oral flow guide 2034 can extend between the oral inlet 2036 and the oral outlet 2038. The oral flow guide 2034 can comprise a surface that is any of a planar, a convex, and a concave surface. In some embodiments, the oral flow guide 2034 is arranged horizontally. In some embodiments, an oral flow guide 2034 is arranged horizontally and another oral flow guide is arranged vertically.

Figure 19:
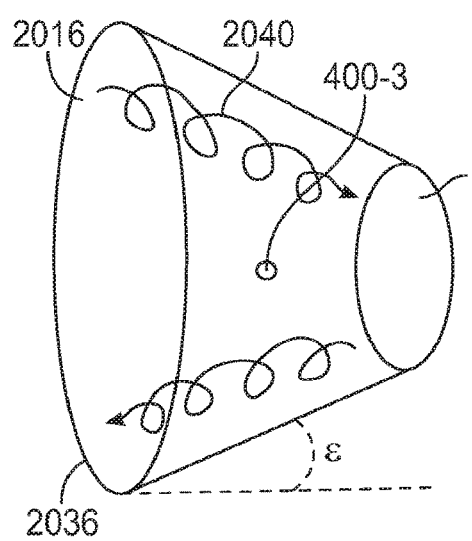
FIG. 19 illustrates a schematic view of turbulent respiration gas flow through a cavity of a respiration sensor, according to some embodiments.
Figure 20:
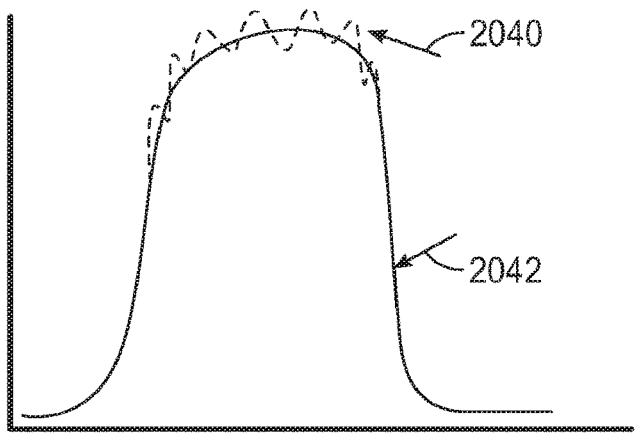
FIG. 20 illustrates a graph showing turbulent noise flow during expiration, according to some embodiments.

FIG. 19 illustrates a schematic view of the oral flow passage 2016 including an entry angle c that can create gas flow turbulence 2040. If the entry angle c is too high, the oral shroud 2017 will create the turbulence 2040 in both directions during inspiration and expiration. FIG. 20 illustrates turbulent noise flow turbulence 2040 during expiration, which is represented by expiration curve 2042 of the measured electrical signal from a thermistor, such as thermistors 400-1, 400-2, 400-3, 500-1, 500-2.

In some embodiments, a cross-sectional area of the oral inlet 2036 mimics a dimension of a patient's open mouth during sleep, but is much less than a fully open mouth and less than a diameter of a patient's forefinger. In some embodiments, the oral inlet 2036 is elliptical in the vertical direction. In such embodiments, the height of the elliptical oral inlet 2036 is approximately 9 mm and the width is less than the height, such as approximately 5 mm. In some embodiments, the oral outlet 2038 is elliptical. In some embodiments, the oral outlet 2038 is circular. In some embodiments where the both the oral inlet 2036 and the oral outlet 2038 are elliptical, the entry angle c is relatively small, such that less turbulence is generated, but the gas flow is less concentrated towards the oral thermistor 400-3. In some embodiments, the oral outlet 2038 is approximately 5 mm.

Figure 21A:
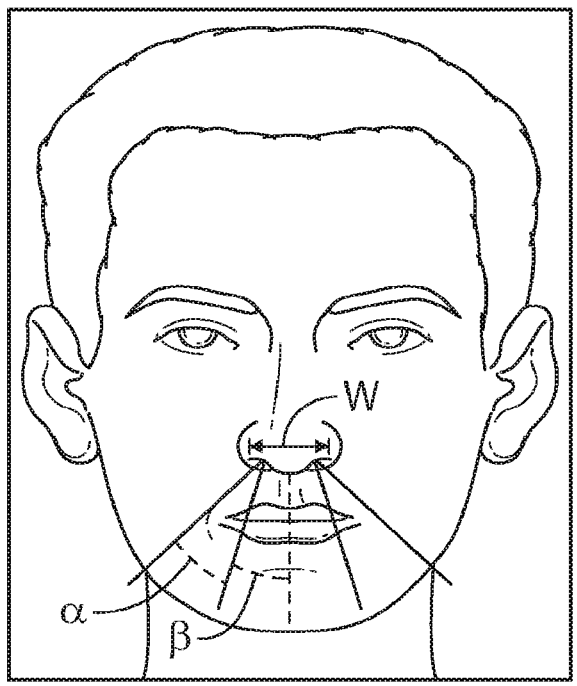
FIGS. 21A and 21B illustrate front and side plan views of exit angles for a gas flow exiting from a patient's nasal cavity, according to some embodiments.
Figure 21B:
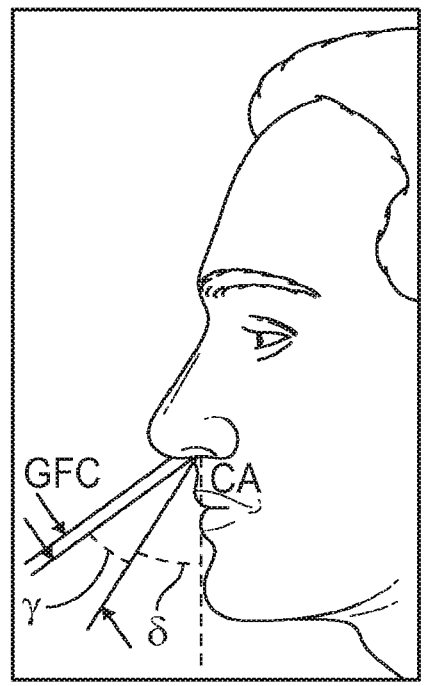

Analysis of entry angle and turbulence generation in the flow cavity, can also be used with reference to the nasal flow passages 301, 2018. FIGS. 21A and 21B illustrate schematic views of possible nasal expiration flow angles, which can be used to determine the potential for turbulence 2040. For example, in a flow path to the side of the nose, an angle α determines a flow width W of the flow path and an angle β determines the direction of the flow path nose. The flow width W is the distance between flow paths from both nostrils. A gas flow column (referred to herein as GFC) is gas flow directed away from the face and the nose. For example, in a flow path directed away from the face and the nose, an angle γ determines a width of the flow path and an angle δ determines the direction of the flow path away from the face and the nose. An area CA defines the cross-sectional surface area of a nostril, which affects the average width of a GFC. In general, a smaller cross-sectional surface area CA of the nostril generates a narrower average width of the GFC. Moreover, turbulence 2040 may be created around the thermistors 400-1, 400-2 by narrow (e.g., low angle α and low cross-sectional surface area CA) breathing GFC that is far to the side of the nose (e.g., high angle β).

III. Respiration Sensor Size and Adjustability

FIGS. 22A, 22B, 23, and 24, illustrate potential distances or dimensions of a patient's facial features or structures, determination of potential dimensions of the respiration sensor using the measured and average patient facial features, and average measurement results for various patient's facial features or structures.

Figure 22A:
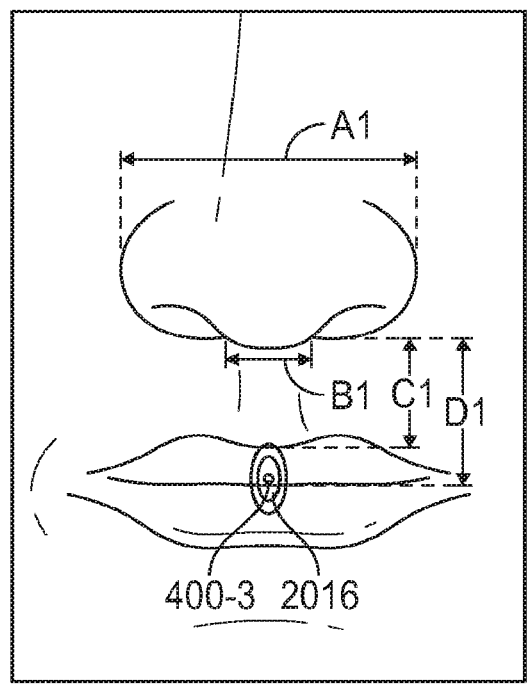
FIGS. 22A and 22B illustrate front and side schematic views of a position of an oral cavity relative to a patient, according to some embodiments.
Figure 22B:
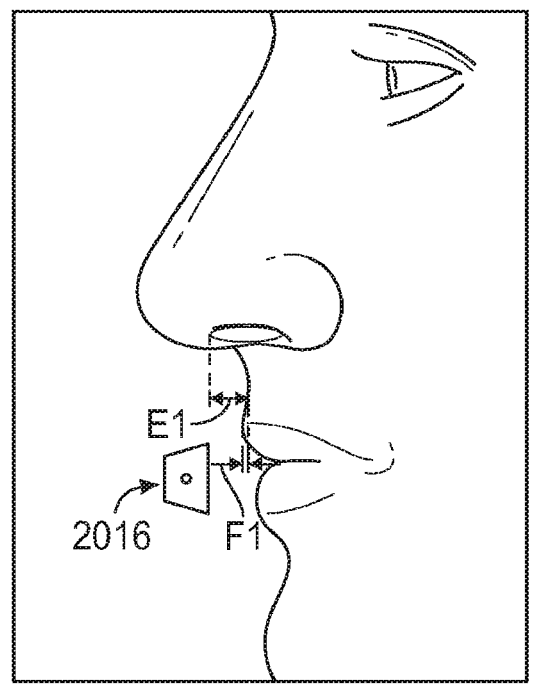

FIGS. 22A and 22B illustrate potential distances or dimensions of a patient's facial features relative to an oral cavity 2016 having a thermistor 400-3 when the respiration sensor is placed on or attached to the patient. More particularly, the identified dimensions include the patient's nose width A1, isthmus width B1, a distance C1 between the bottom of the nose and the upper lip, a distance D1 between the bottom of the nose and the oral passage (e.g. mouth), a distance E1 between the front edge of the nasal passage and the upper lip, and a lip thickness F1, e.g., the distance the lip protrudes outwardly relative to the philtrum.

Figure 23:
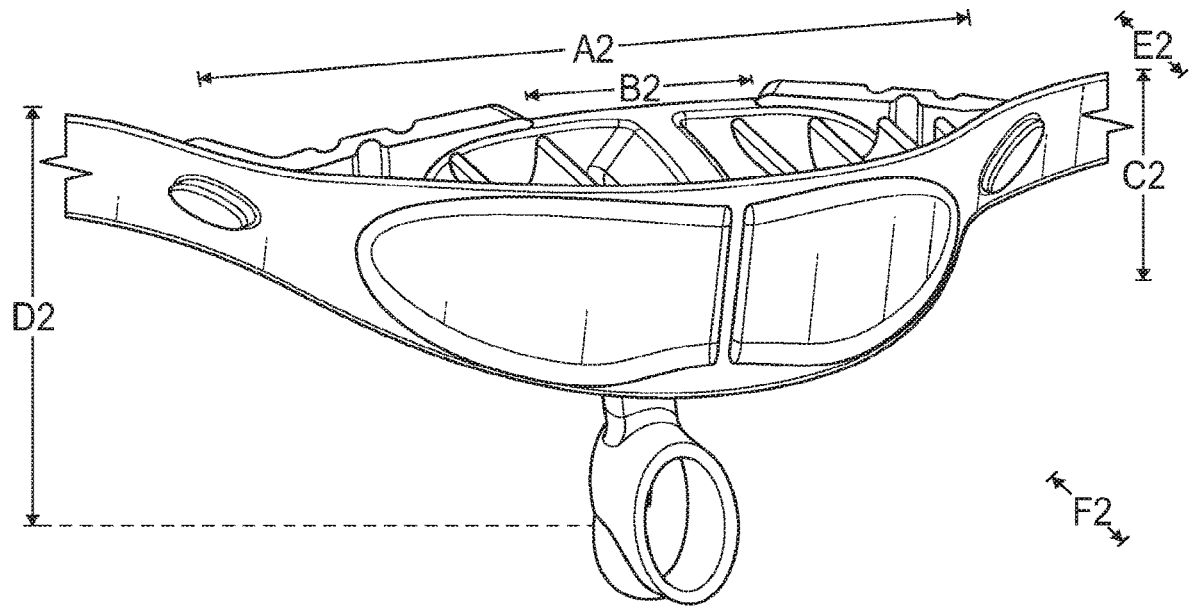
FIG. 23 illustrates a front perspective view of a respiration sensor, according to some embodiments.

FIG. 23 illustrates a respiration sensor, such as, for example, the respiration sensor 100a, 100b, depicting dimensions of the respiration sensor, which can correspond to analysis of the measured features of the patient as shown in FIGS. 22A and 22B. Accordingly, the measured facial features identified in FIGS. 22A and 22B help facilitate the design dimensions of the respiration sensor 100a, 100b. A2 should be at least A1, but preferably A2 is more than A1 to ensure capturing flow through the patient's nostrils. Similarly, B2 should be no more than B1, but preferably B2 is less than B1 to ensure that B2 does not prevent or disturb flow through the patient's nostrils.

The measured facial features shown in FIGS. 22A and 22B can be used to select design dimensions of the respiration sensor shown in FIG. 23. In some embodiments, measurements of particular patient can be used to select design dimensions for the respiration sensor. In some examples, measurements of a group of patients, such as adults or children, can be used to select design dimensions for an adult respiration sensor or a child respiration sensor.

A measured facial feature can correspond to a design dimension of the respiration sensor. For example: a patient nose width A1 can be used to select the width A2 of the respiration sensor; a patient isthmus width B1 can be used to select the battery frame 2014 width B2; the distance C1 between the bottom of the nose and the upper lip can be used to select a height C2 of the respiration sensor housing 2001; the distance D1 between the bottom of the nose and the oral passage can be used to select a distance D2 between the top of the respiration sensor 100a, 100b, adjacent the nasal inlet 2024 and the oral flow passage 2016, 302; the distance E1 between the front edge of the nasal passage and the upper lip can be used to select a depth of the respiration sensor 100a, 100b; and the lip thickness F1 can be used to select a depth F2 of the oral flow passage 302, 2016.

In some embodiments, the distance C2 of the respiration sensor 100a, 100b is less than 20 mm, but preferably less than 15 mm. In some embodiments, the distance C2 of the respiration sensor 100a, 100b is approximately 10 mm to accommodate different face structures. In some embodiments, width A2 of the respiration sensor 100a, 100b is more than 25 mm, but preferably about 45 mm to adequately capture the gas flow of patients with large width A2. In some embodiments, the distance D2 of the respiration sensor 100a, 100b is more than 5 mm, but preferably more than 10 mm. In some embodiments, the distance D2 of the respiration sensor 100a, 100b is more than 15 mm to capture gas flow coming out from the nostrils. In some embodiments, the cross-sectional area of the nasal flow passages 301, 2018 is greater than the cross-sectional area of the nostrils of a patient to capture breathing gas flow. In some embodiments, the battery frame 2014 includes a dimension B2 corresponding to the isthmus width B1 and is preferably less than 10 mm, but more preferably less than 5 mm. In some embodiments, the oral flow passage 2016 is located parallel to the breathing gas flow directed from the mouth of the patient.

Figure 24:
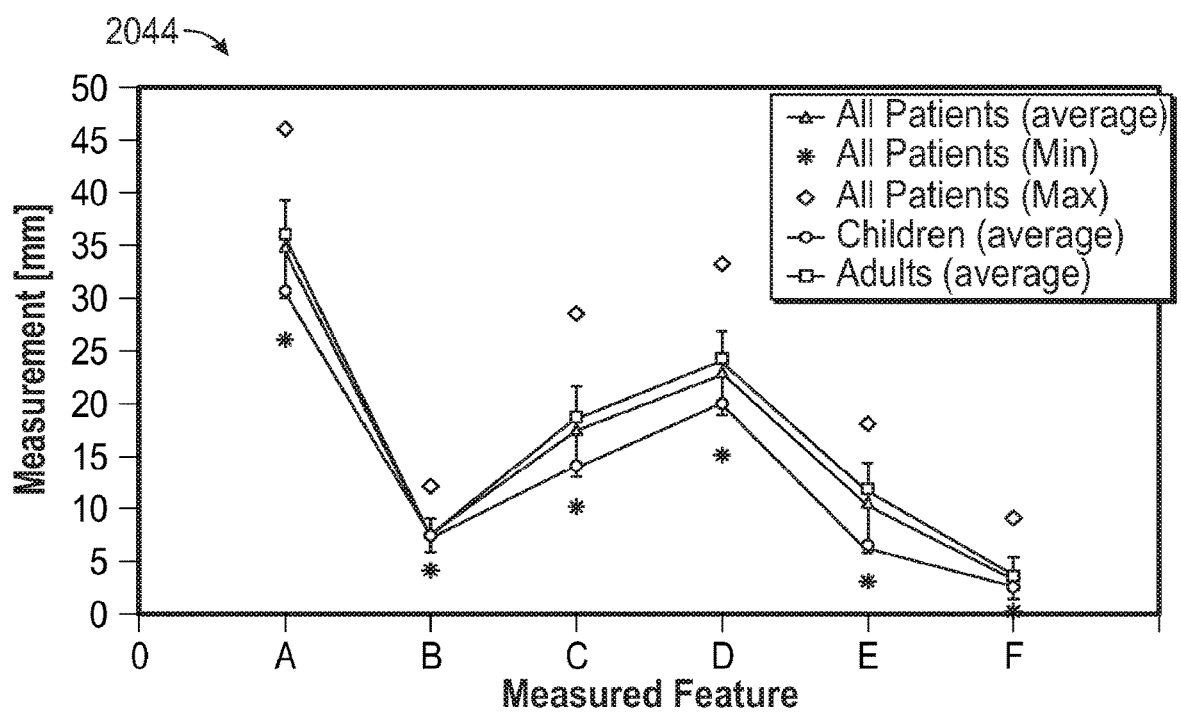
FIG. 24 illustrates a graph showing measurements for the respiration sensor of FIG. 23 for different patients, according to some embodiments.

FIG. 24 illustrates a graph 2044 of average measurement results for various facial features of a sample of patients including the patient's nose width A1, the isthmus width B1, the distance C1 between the bottom of the nose and the upper lip, the distance D1 between the bottom of the nose and the oral passage (e.g. mouth), the distance E1 between the front edge of the nasal passage and the upper lip, and the patient's lip height F1. The graph 2044 illustrates the measurement results of a group of 45 Caucasian people including women, men, and children between the ages of 0 to 70 years old. The measured values influence the dimensional designs of the respiration sensor 100a, 100b with respect to the nose and the mouth including the size of nasal passages and the location of the oral passage. It should be understood that measurements for patients may also be outside of the scope of the measured feature in this graph.

Figure 25A:
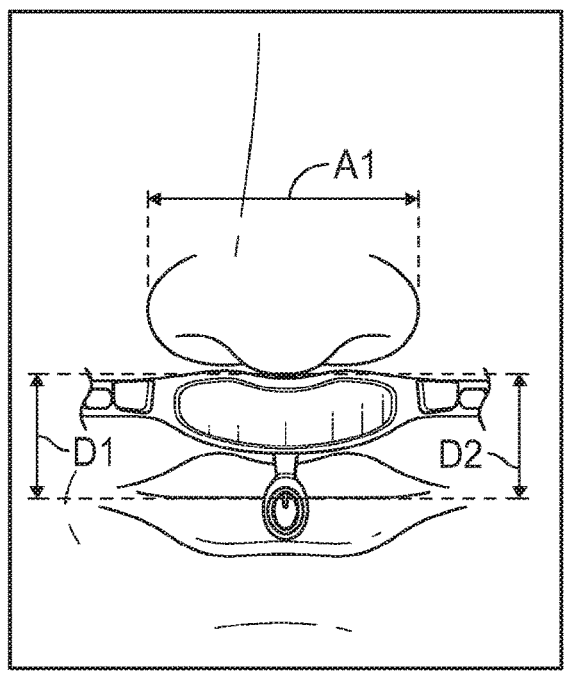
FIGS. 25A and 25B illustrates a front plan views of positions of an oral cavity for a respiration sensor relative to a mouth of different patients, according to some embodiments.

FIG. 25A illustrates a respiration sensor, such as, for example, respiration sensor 100b that includes the distance D2 between the top of the respiration sensor 100b, adjacent the nasal inlet 2024, and the oral flow passage 2016, 302. The distance D2 can be approximately equal to 15 mm for patients with a smaller distance D1. Such a respiration sensor can accommodate patients including a distance D1 in the range of approximately 10 mm to 25 mm. In some embodiments, the distance D1 is between approximately 5 mm to 50 mm.

Figure 25B:
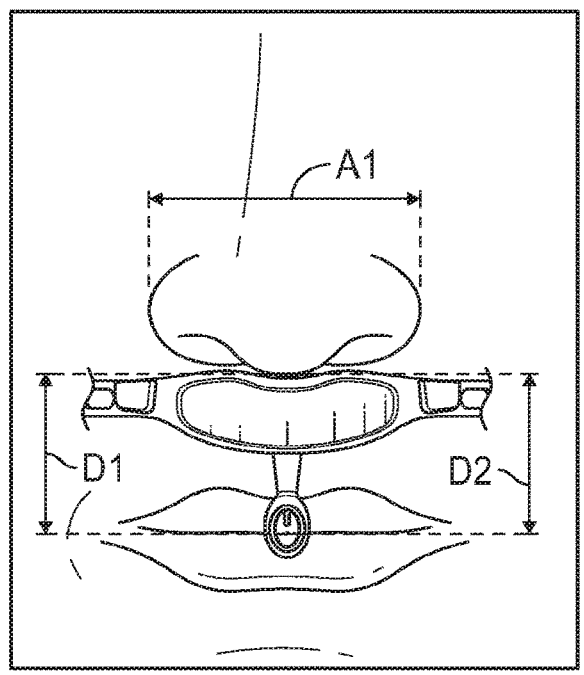

FIG. 25B illustrates a respiration sensor, such as, for example, the respiration sensor 100b that includes the distance D2 approximately equal to 33 mm for patients with a larger distance D1. Such a respiration sensor can accommodate patients including a distance D1 in the range of approximately 24 mm to 40 mm. In some embodiments, the distance D1 is between approximately 5 mm to 50 mm.

Figure 26:
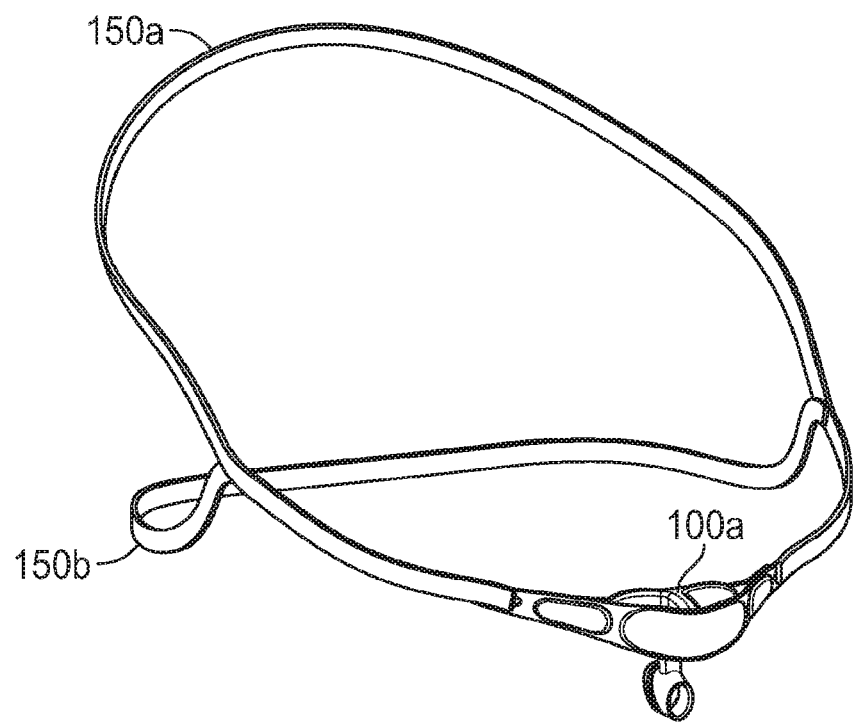
FIG. 26 illustrates a front perspective view of a respiration sensor having a strap, according to some embodiments.
Figure 27:
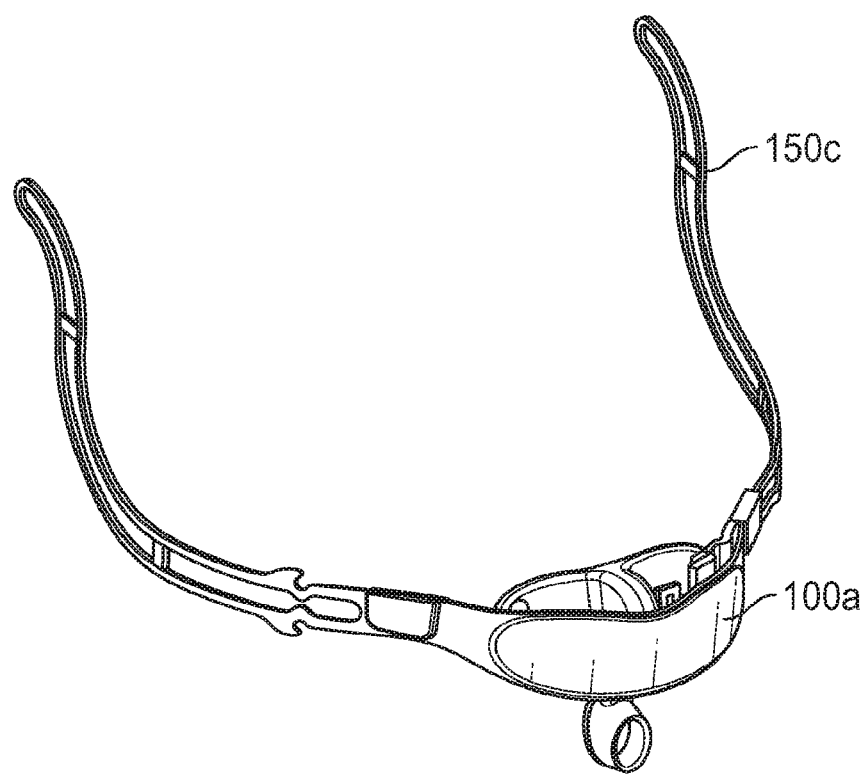
FIG. 27 illustrates a front perspective view of a respiration sensor having a band, according to some embodiments.

FIGS. 26 and 27 illustrate embodiments of features to attach the respiration sensor 100a to a patient. The features to attach the respiration sensor 100a can include any of a string, strap, or band, which can maintain a position of respiration sensor 100a relative to the patient's physiognomy. It should be understood that any of the features to attach the respiration sensors 100a or 100b can include the features to attach the respiration sensor to a patient.

A strap 150a, shown in FIG. 26, can have ends that are attached to the respiration sensor 100a to form a loop. The strap 150a can have a length such that the respiration sensor 100a is engaged against a patient's face when the device is worn by the patient. In some embodiments, an additional strap 150b extends from any of the strap 150a or the respiration sensor 100a. The additional strap 150b can provide additional support and tension to secure the device with the patient. The strap 150a and additional strap 150b can be configured such that a portion of the strap 150a extends above a patient's ears, and a portion of the additional strap 150b extends below a patient's ears.

FIG. 27 illustrates a respiration sensor 100a having a placement band 150c. In some embodiments, the placement band 150c comprises a semi-rigid framework that is configured to guide straps that overlay the placement band 150c and extend over preferred placement portions of a patient's face. In some embodiments, the placement band 150c comprises a flexible plastic material that is configured to substantially retain its shape during use. The flexible placement band 150c can move, in a first plane, towards or away from a patient's face. The placement band 150c can be moved or biased in the first plane to engage against the patient's face and adapt to the shape of the patient's face. The placement band 150c is less flexible relative to a second plane, transverse to the first plane, thereby preventing or resisting movement of the placement band 150c along the patient's face or twisting of the band 150c.

The placement band 150a, 150c can have a width that is approximately 5 mm, but it can be wider or narrower. A wider band can reduce the surface pressure on the face by the band. At least a portion of a surface of the band can be covered with a material that is soft and/or breathable. For example, a surface of the band configured to engage against the face or skin of the patient can comprise a cotton or similar material.

The shape of the band 150c is configured to extend from the respiration sensor 100a, below the cheek bones of the patient. The band 150c can curve from the area below the cheek bones of the patient toward the patient's ears, forming a shape of an S-curve or similar.

The band 150c can be coupled with one or more additional band and/or strap. For example, the band 150c can be coupled to any of straps 150a and 150b. When the straps 150a, 150b pull the band 150c and respiration sensor 100a towards the patient's face, a force vector of the respiration sensor 100a is approximately straight, towards the face or upper lip of the patient. Accordingly, the band 150c can decrease the surface pressure against the patient's isthmus or another portions of the patient's face or lip.

IV. Respiration Sensor Features for Monitoring and Analysis

Figure 28:
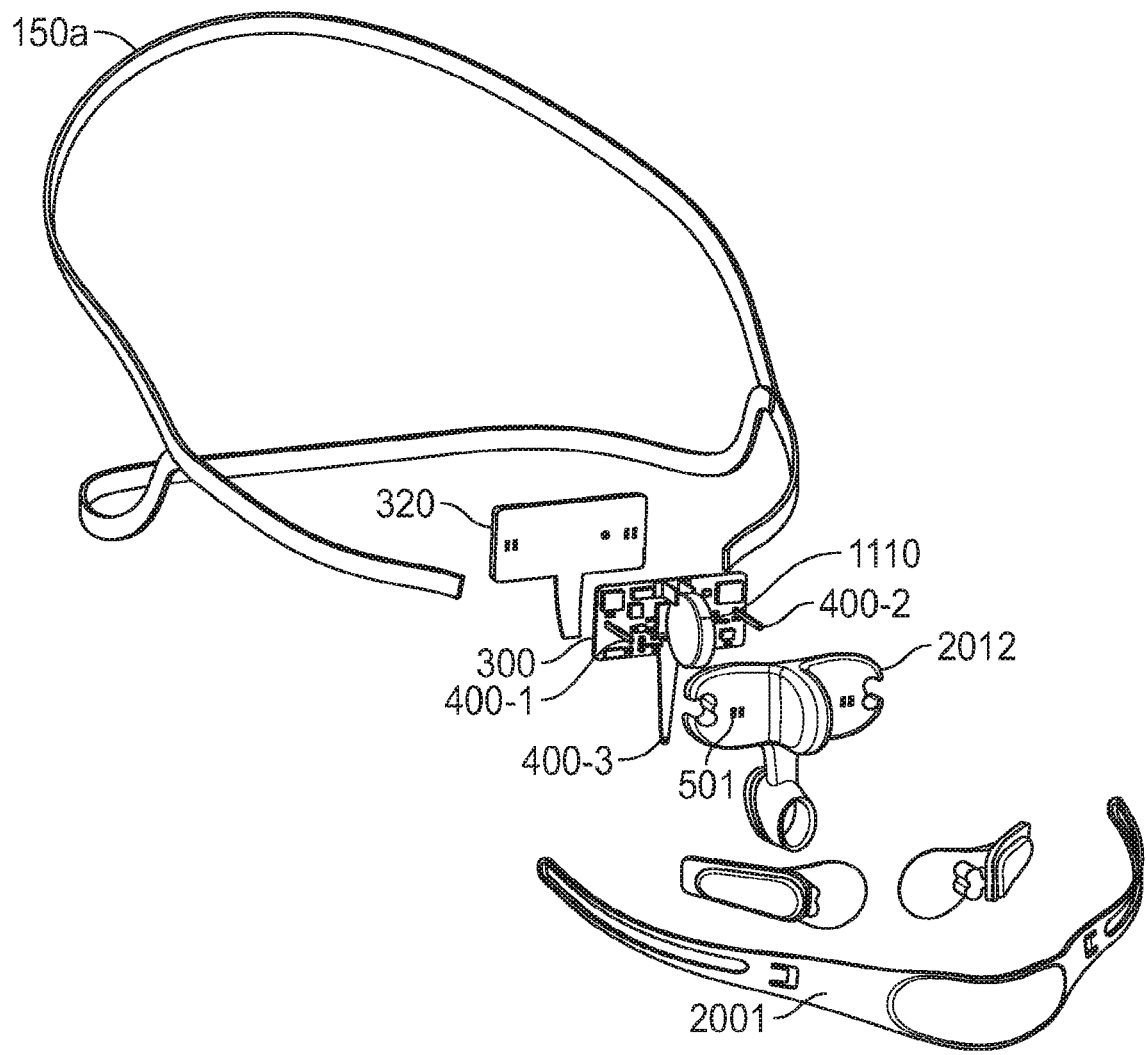
FIG. 28 illustrates a front perspective exploded view of a respiration sensor, according to some embodiments.

FIG. 28 illustrates an exploded view of the respiration sensor 100a, 100b for example, including a housing 2001, shroud 2012, and electronics board 300, according to some embodiments.

The electronics board 300 includes the electronic components used in the respiration sensor 100a, 100b. The electronics board 300 can include a battery 1110 and sensors, such as a thermistor 400-1, 400-2, 400-3, and a capacitive plate. In some embodiments, the electronics board 300 is made of, for example, glass-reinforced epoxy laminate material (e.g., FR4 substrate) containing automatic machine placed components, commonly used in automated mass series production to make the construction low cost. The electronics board 300 can be coupled to a base plate or frame 320. In some embodiments, the frame 320 includes plastics, which contains electrically conductive areas or conductors.

In some embodiments of the present disclosure, the battery 1110 can be a disposable or rechargeable battery. In some embodiments, the respiration sensor 100a, 100b is configured to be powered by solar energy. For example, the respiration sensor 100a, 100b can include a solar panel which can be coupled to a battery.

The shroud 2012 defines at least a portion of the nasal flow passages and the oral flow passage of the sensor. In some embodiments, the electronics board 300 is positioned between the frame 320 and the shroud 2012. Any of the frame 320 and the shroud 2012 can include a cavity to protect the electronics board 300 when the respiration sensor 100a, 100b is assembled. The frame 320 and/or the shroud 2012 can be made of elastic silicone, plastics, or similar material.

In some embodiments, an ambient air thermistor is positioned further away from the breathing gas flow otherwise interfering ambient air measurement. In aspects of the present disclosure, the shroud 2012 can include a perforation 501 that enables ambient air to be in touch with the ambient air thermistor through the shroud 2012 to get fast response time, but also to protect ambient air thermistor for example from touching with a finger or any unwanted air flow, such as air conditioning.

Figure 29:
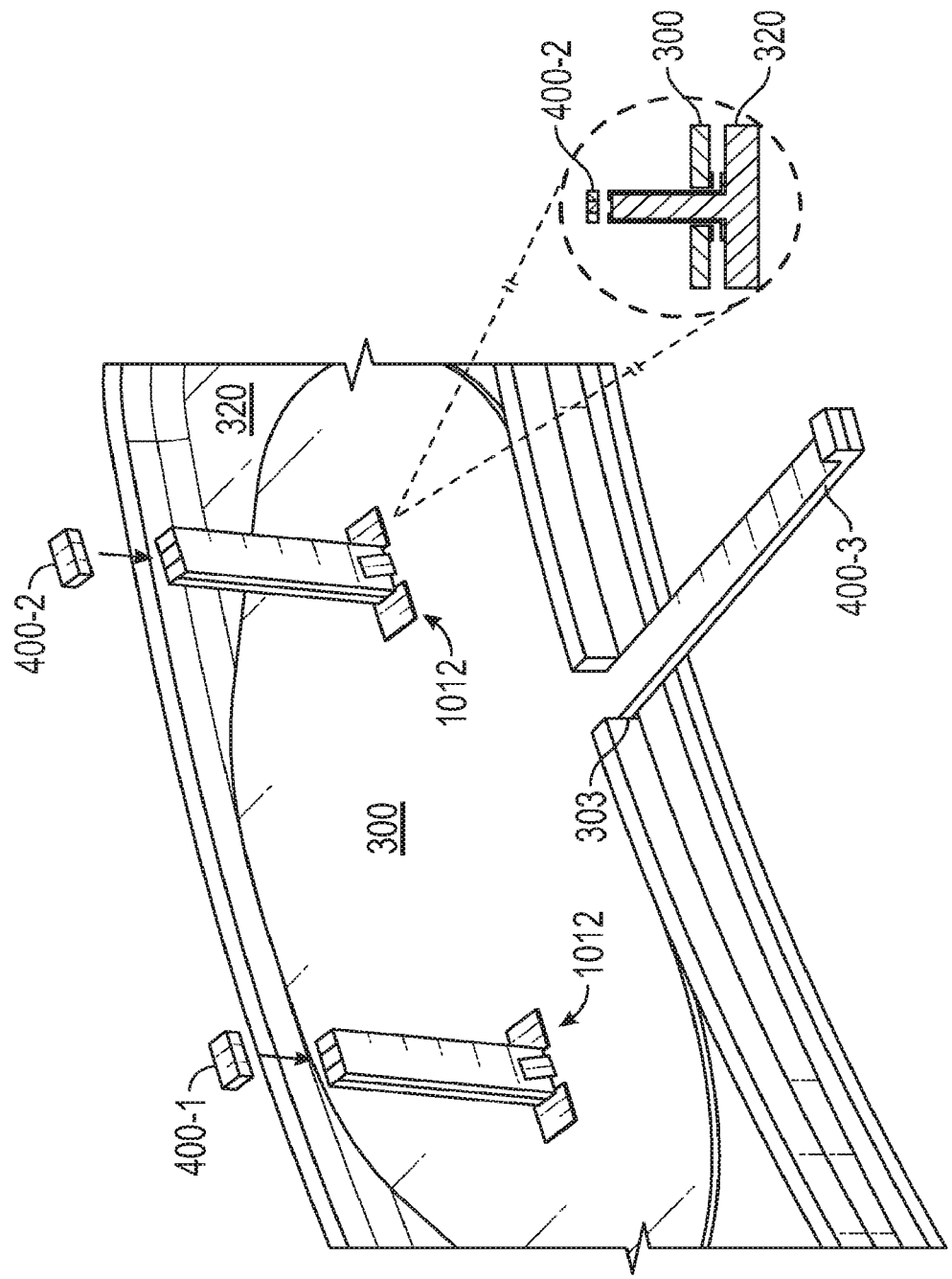
FIG. 29 illustrates a top perspective detail view of an electronics board and frame of a respiration sensor, according to some embodiments.

Referring to FIG. 29, a portion of the frame 320 can form a support structure for the thermistors 400-1, 400-2. The electronics board 300 may include two perforations that enable two poles of the frame 320 to pierce through the electronics board 300 to form the thermistor support structure. The poles locate and keep the board in place with a mechanical locking mechanism. No screws or similar are needed. The poles also contain electrical contacts on the tip of the poles where thermistors 400-1, 400-2, which are sensitive to nasal breathing gas flow, are coupled. Electrically conductive connections 1012 on the side surfaces of poles further connect thermistors 400-1, 400-1 to the electronics board 300 via electrical contacts on the top surface of the electronics board 300 next to the poles. When the frame 320 is placed under the electronics board 300, electrical contacts on the top surface of the frame 320 connect with adjacent electrical contacts on the bottom surface of electronics board 300. Electrically conductive glue can be used to ensure electrical contact. In some embodiments, a thermistor 400-3 sensitive to breathing gas flow through the mouth is located to the tip of the electronics board 300. A bottom side of frame 320, adjacent to electronics board 300 contains an inset 303 to enable thermistor 400-3 to locate into the middle of the flow cavity.

Electrical signals from thermistors 400-1, 400-2, 400-3 proportional to corresponding ambient, skin, nasal or oral temperature changes are conducted through the electrically conductive connections 1012 and conductors to central processing unit on the electronics board. The central processing unit can convert the analog data into digital form, process and transmit the data wirelessly, for example, via an RF transmitter, to a host where the data can be shown or displayed to a caregiver in a suitable form of numbers and/or waveforms.

Figure 30:
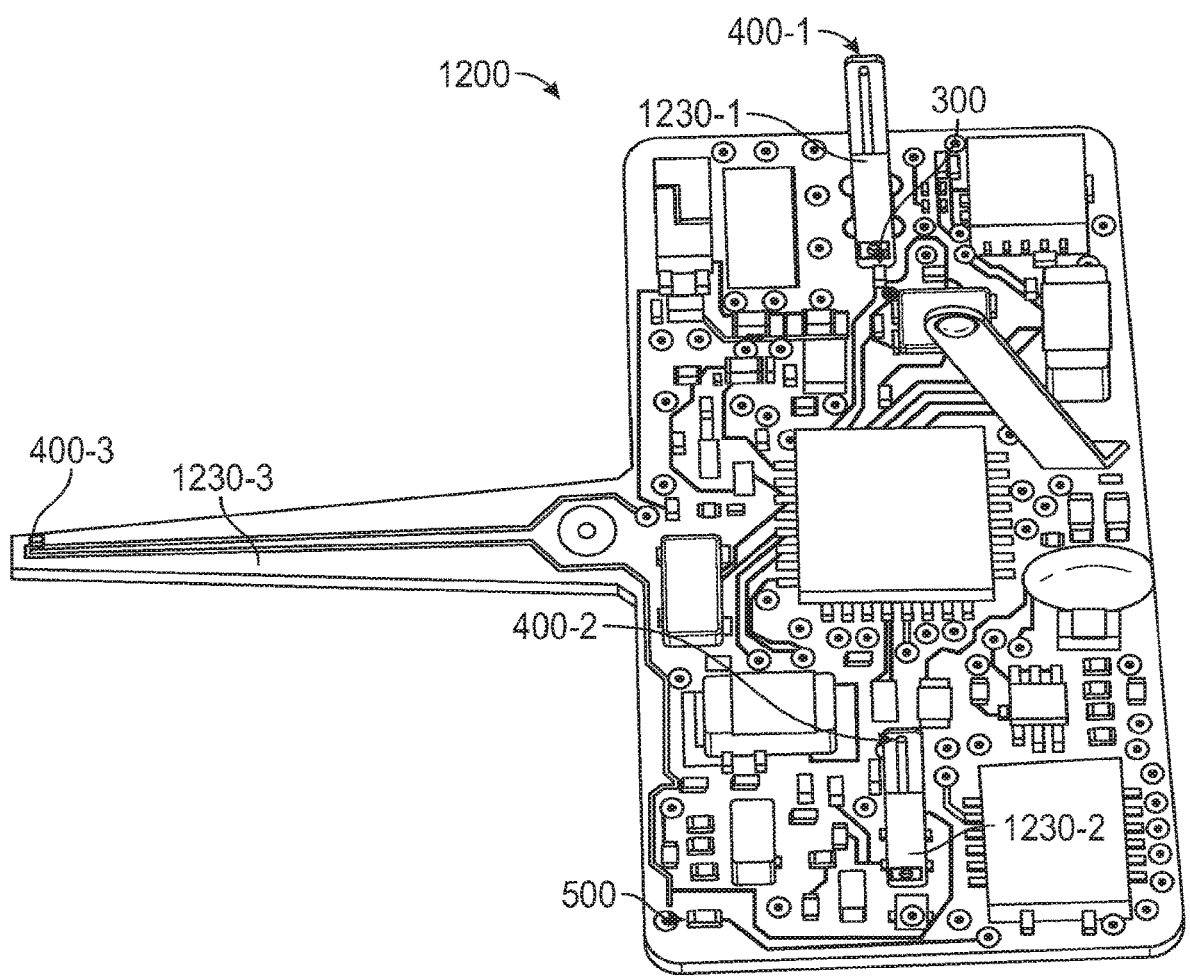
FIG. 30 illustrates a top perspective view of an electronics board of a respiration sensor, according to some embodiments.

FIG. 30 illustrates a detailed view of an electronics assembly 1200, for example, any respiration sensor 100a, 100b which can include two nasal flow thermistors 400-1, 400-2 and one oral flow thermistor 400-3, according to some embodiments. Thermistors 400-1 and 400-2 are configured to measure breathing from nostrils. Thermistor 400-3 may be configured to measure breathing from the mouth. A thermistor 500-1 (see FIG. 32) may also be included in electronics assembly 1200 to measure ambient temperature.

Support structures 1230-1, 1230-2, 1230-3 contain electrical wires on both sides of a strip between electrical connections at both ends of the strips. The support structures can include first and second support structures 1230-1, 1230-2, which can support the nasal flow thermistors 400-1, 400-2. Additionally, a third support structure 1230-3 can support the oral flow thermistor 400-3. In some embodiments, support structures 1230-1, 1230-2, 1230-3 may include an electrically and thermally insulating material (e.g., FR4 substrate). Thermistors 400-1, 400-2, 400-3 can be soldered to electrical connections in the first end of the strips. Second ends of strips are placed into small holes in electronics board 300 and soldered to form electrical connections on the sides of the strip to corresponding electrical contacts on the board to electrically connect thermistors 400-1, 400-2, 400-3 to sensor electronics in the plane of the electronics board.

The cross-sectional areas of copper or similar traces within support structures 1230-1, 1230-2, 1230-3 are reduced to minimize thermal flow through the electrical conductors from the plane of board to thermistors 400-1, 400-2, 400-3. To minimize the thermal mass of the thermistors 400-1, 400-2, 400-3, the support structures 1230-1, 1230-2, 1230-3 can be formed from a thermally non-conductive or insulating material. These optimizations make thermistors 400-1, 400-2, 400-3 as sensitive as possible to thermal changes caused by the breathing gas flowing past the thermistor during expiration or ambient gas flowing past the thermistor during inspiration.

Figure 31:
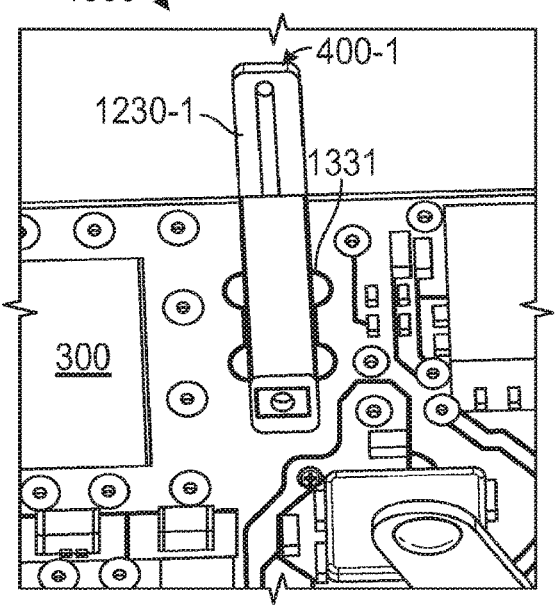
FIG. 31 illustrates a top perspective detail view of the electronics board of FIG. 30, according to some embodiments.

FIG. 31 illustrates a partial view 1300 of an electronics board 300 in, for example, any respiration sensor 100a, 100b including details of a nasal flow thermistor 400-1, according to some embodiments. Support structure 1230-1 may include an FR4 substrate strip with thermistor 400-1 placed on the tip of the strip. At the bottom of support structure 1230-1, a soldered contact provides electrical contacts to thermistor 400-1 on both sides of support structure 1230-1 (e.g., +/−terminals).

In some embodiments, the support structures 1230-1, 1230-2, can have a proximal portion coupled to the electronics board 300 and a distal portion transverse to a plane defined by the top of the electronics board 300. When the electronics board is positioned within the housing, the distal portion of the support structures 1230-1, 1230-2 can extend into respective nasal flow passages. In some embodiments, the support structure 1230-3 can have a proximal portion coupled to the electronics board 300 and a distal portion that is normal with or substantially parallel to a plane defined by the top of the electronics board 300.

Figure 32:
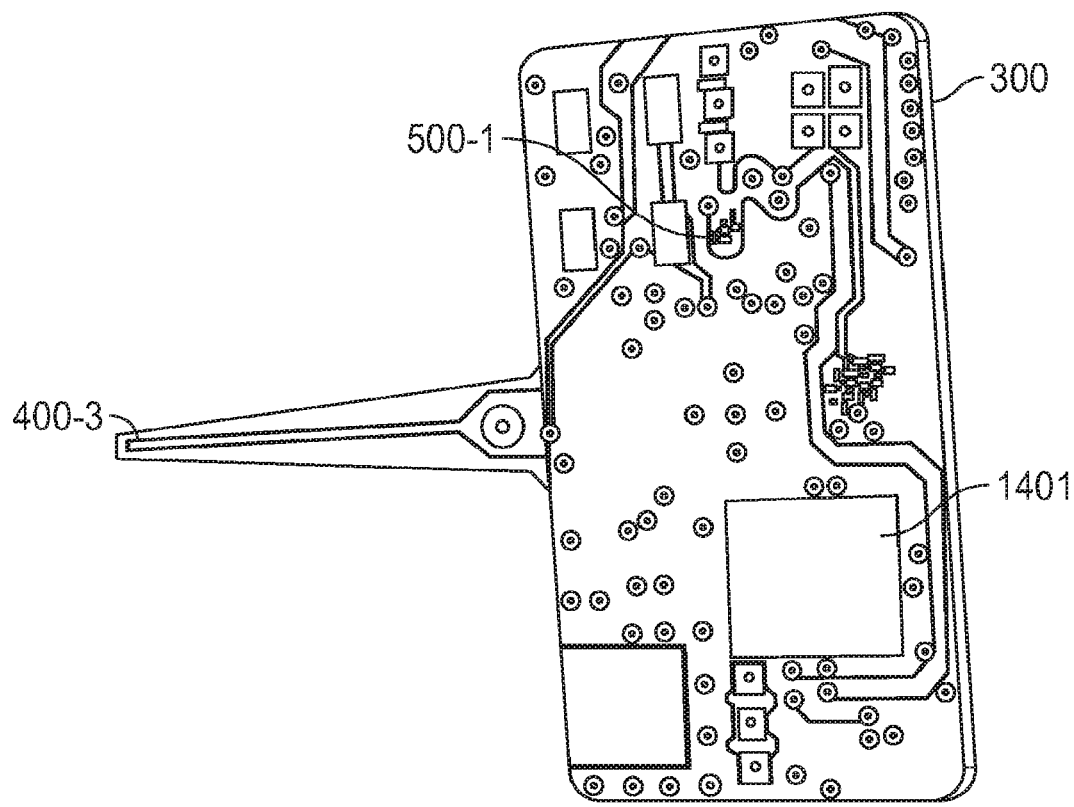
FIG. 32 illustrates a bottom perspective view of the electronics board of FIG. 30, according to some embodiments.

FIG. 32 illustrates a detailed view of a bottom portion of an electronics board 300 of a respiration sensor 100a, 100b including a thermistor 500-1 to measure skin temperature, and a capacitive plate or sensor 1401 to measure sensor location in the upper lip, according to some embodiments. A respiration sensor including electronics board may be turned on/off based on the signal. Additionally, in some embodiments, the electronics board 300 includes an accelerometer 1150.

Figure 33:
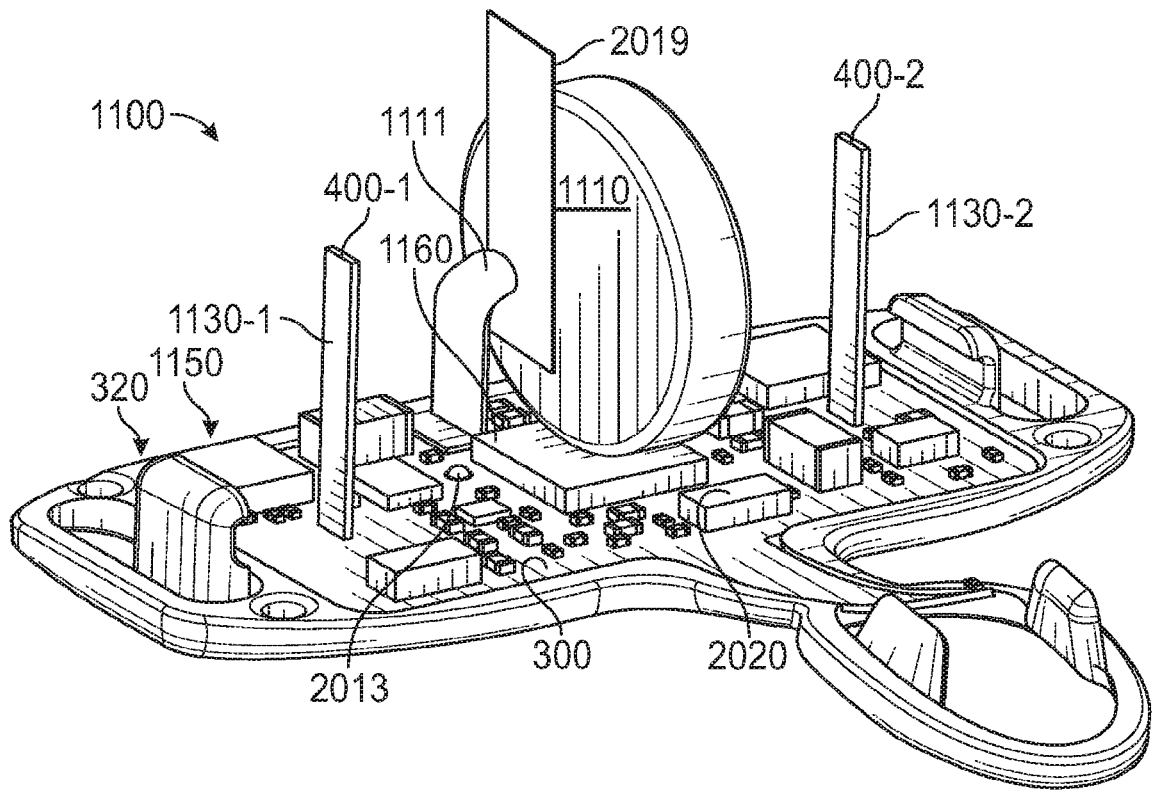
FIG. 33 illustrates a top perspective view of the electronics board of FIG. 30 coupled with a frame and a battery, according to some embodiments.

FIG. 33 illustrates a detailed view of an electronics board 300 coupled with a frame 320 and a battery 1110, according to some embodiments. Support structures 1130-1 and 1130-2 extend away from the electronics board, and include thermistors 400-1 and 400-2, respectively. A thermistor 500-1 sensitive to skin temperature may be located on the bottom side of the board as close to skin as possible. In some embodiments, the thermistor is placed close to one of the two ridges above the upper lip to ensure closest distance to skin. The frame 320 most advantageously contains a perforation adjacent to thermistor that enables better thermal contact to upper lip skin. Perforation can also be filled with thermally conductive material to increase conductivity to skin.

The electronics board 300 includes a battery contact tab 1111 that extends toward the battery 1110. A portion of the spacer 2019 is positioned between the battery contact tab 1111 and the battery 1110 such that the contact tab 1111 is spaced apart from the battery 1110. When the spacer 2019 is coupled with the respiration sensor 100b, the battery 1110 the battery does not provide power to the respiration sensor 100b.

In some embodiments, the board 300 includes an LED 2013, which can be visible from an outer surface of the respiration sensor 100b when the respiration sensor 100b is assembled. In some embodiments, the board 300 includes a microphone 2020. The microphone 2020 can detect ambient sounds or a patient speaking. The sound detected by the microphone 2020 can be used to during processing of signals. For example, the sound detected by the microphone 2020 can filtered out to reduce or remove noise in the signals from the other sensors.

In some embodiments, any respiration sensor 100a, 100b is an affordable, disposable, wireless sensor configured to detect breath flow in real time. Accordingly, the sensor 100a, 100b includes a battery 1110, which may provide several days (e.g., five days, or more) of continuous, real time, fast response operation with a high signal quality. In some embodiments, the respiration sensor 100a, 100b is configured to measure a respiration rate (RR) and magnitude, and to provide real time respiration waveforms, in digital and/or analog form. Furthermore, a processor circuit in the respiration sensor may be configured to determine trends and projections based on the real-time data (e.g., via moving averages, Kalman filtering, and the like). The respiration sensor 100a, 100b may also provide skin temperature, body position, movement, fall detection (e.g., through an accelerometer 1150), sensor placement, and the like.

V. Processing of Readings for Indications

Figure 34:
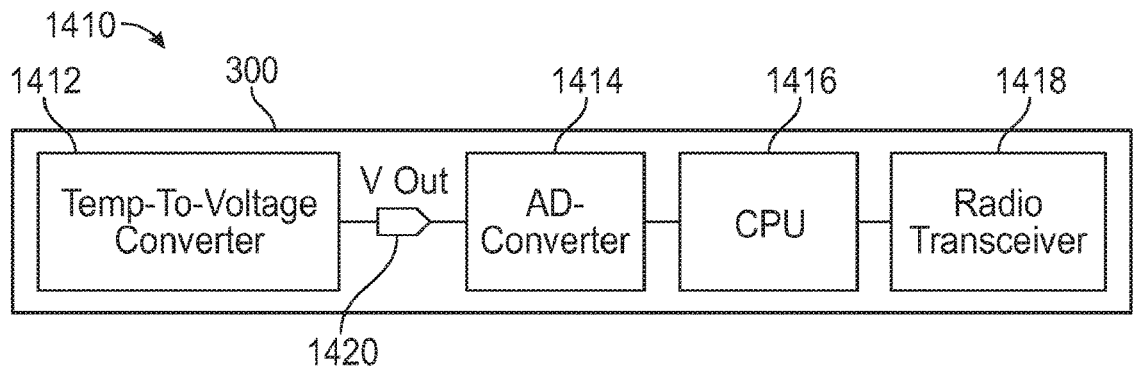
FIG. 34 illustrates a block diagram of an electronics board of a respiration sensor, according to some embodiments.

FIG. 34 illustrates a block diagram 1410 of components, which are utilized on the electronics board 300 of the respiration sensor 100a, 100b according to some embodiments. In such embodiments, the electronics board 300 includes a temperature-to-voltage converter 1412, an analog-to-digital (AD) converter 1414, a central processing unit (CPU) 1416, and a communications module or radio transceiver 1418 for providing a two-way data communication coupling to a network link that is connected to a local network. Such communication may occur, for example, through a radio-frequency transceiver. In addition, short-range communication may occur, such as using a Bluetooth, Wi-Fi, or other such transceiver. In some embodiments, the CPU 1416 includes the Bluetooth low energy processor 1160 (shown in FIG. 33).

In some embodiments, the temperature-to-voltage converter 1412 includes any of the thermistor 500-1, the thermistor 500-2, the thermistor 400-1, the thermistor 400-2, and the thermistor 400-3. In some embodiments, any of the thermistors 400-1, 400-2, 400-3, 500-1, 500-2 are negative temperature coefficient (NTC) type thermistors, such that the thermistor's electrical resistance decreases when the temperature increases. In some other embodiments, any of the thermistors are positive temperature coefficient (PTC) type thermistors, such that the thermistor's electrical resistance increases when the temperature increases. The respiration sensor 100a, 100b can include any combination of NTC type thermistors and PTC type thermistors. The temperature-to-voltage converter 1412 converts or transforms the temperature resistance value detected at any of the thermistors to a voltage at Vout 1420. The AD converter 1414 then converts the Vout 1420 into digital form, which is received by the CPU 1416 for further processing and calculations. In some embodiments, the CPU 1416 can transmit the digital signal to the host monitor or other client device. The CPU 1416 can transmit the digital signal via the Bluetooth low energy processor 1160. In some other embodiments, the CPU 1416 transmits the digital signal to the communications module or radio transceiver 1418 for wireless transmission to the host monitor or other client device.

In addition to the respiration sensor 100a, 100b measuring or detecting temperature differences between inspiratory and expiratory gas flows via the thermistors 400-1, 400-2, 400-3, the respiration sensor 100a, 100b also measures or detects ambient air temperature via the thermistor 500-1 and conductive temperature from the patient's skin via the thermistor 500-2.

In some instances, the thermistor 500-1 and the thermistor 500-2 include a wide operating temperature range and can be adjusted to include a lowest and a highest temperature of operating range. The respiration sensor 100a, 100b is configured to measure or detect the electrical signal voltages proportional to the ambient air temperature via the thermistor 500-1 and the skin temperature via the thermistor 500-2 and compensate the signal offset, gain, and the peak to peak amplitude errors from the inspiratory and expiratory gas flow signal amplitude.

In some embodiments, any of the thermistors 400-1, 400-2, 400-3, 500-1, 500-2 can measure any of an inspiratory gas flow, an expiratory gas flow, an ambient air temperature, and a conductive temperature. For example, when the respiration sensor 100a, 100b is turned on, but is not yet placed on or attached to the patient's face, the thermistor 400-1, 400-2, 400-3, 500-1, 500-2 detect ambient air temperature. When the respiration sensor 100a, 100b is placed on or attached to the patient's face, the thermistor 500-2 begins detecting the temperature of skin on the patient's upper lip. Meanwhile, the thermistor 500-1 remains detecting the ambient air temperature and the thermistors 400-1, 400-2, 400-3 begin detecting the temperature differences between the inspiratory and the expiratory gas flows (e.g., inspired ambient air and expired warm gas coming out from the lungs).

During normal, stable ambient conditions, after the respiration sensor 100a, 100b is placed on or attached to the patient's face, the electrical voltage signals from the thermistor 500-2 (e.g., detecting ambient air temperature) are stable and change slowly, whereas the electrical voltage signal from at least one of the thermistors 400-1, 400-2, 400-3 changes its amplitude relatively faster. In some embodiments where the thermistors are NTC type and the temperature-to-voltage converter 1412 includes negative feedback amplifiers, the electrical voltage signal changes between maximum voltage proportional to ambient air temperature and minimum voltage proportional to temperature of exhaled warm, moister gas coming out of the patient's lungs.

In other embodiments where the thermistors 400-1, 400-2, 400-3, 500-1, 500-2 are PTC type and the temperature-to-voltage converter 1412 include positive feedback amplifiers, the electrical voltage signal changes between maximum voltage proportional to temperature of exhaled warm, moister gas coming out of the patient's lungs and minimum voltage proportional to ambient air temperature. In both NTC type and PTC type scenarios, the frequency of electrical signal may vary between 0 to 3 Hz (0-180 RR/min) depending on how fast the patient is inhaling and exhaling. Smaller patients tend to breathe relatively faster than relatively larger patients, such as adults.

Figure 35:
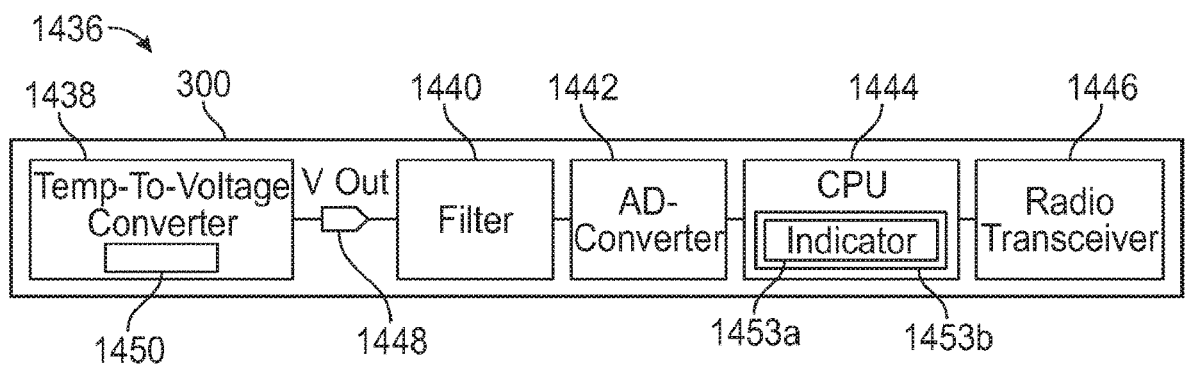
FIG. 35 illustrates another block diagram of an electronics board of a respiration sensor, according to some embodiments.

FIG. 35 illustrates a block diagram 1436 of components, which are utilized on the electronics board 300 of the respiration sensor 100a, 100b according to some embodiments. In such embodiments, the electronics board 300 includes a temperature-to-voltage converter 1438, a filter 1440, an analog-to-digital (AD) converter 1442, a central processing unit (CPU) 1444, and a communications module 1446 for providing a two-way data communication coupling to a network link that is connected to a local network. Such communication may occur, for example, through a radio-frequency transceiver. In addition, short-range communication may occur, such as using a Bluetooth, Wi-Fi, or other such transceiver. In some embodiments, the CPU 1444 includes the Bluetooth low energy processor 1160 (shown in FIG. 33).

In some embodiments, the temperature-to-voltage converter 1438 includes any of the thermistors 400-1, 400-2, 400-3, 500-1, 500-2. In some embodiments, any of the thermistors are negative temperature coefficient (NTC) type thermistors, such that the thermistor's electrical resistance decreases when the temperature increases. In other embodiments, any of the thermistors are positive temperature coefficient (PTC) type thermistors, such that the thermistor's electrical resistance increases when the temperature increases. The respiration sensor 100a, 100b can include any combination of NTC type thermistors and PTC type thermistors. The temperature-to-voltage converter 1438 converts or transforms the temperature resistance value detected at one of the thermistors 400-1, 400-2, 400-3, 500-1, 500-2 to a voltage at Vout 1448. In some embodiments, the temperature-to-voltage converter 1438 also includes an amplifier 1451, which increases the voltage at Vout 1448 for increased accuracy and resolution of the breathing gas flow signal.

The filter 1440 eliminates or subtracts any of the ambient air and the conducting skin temperature change from the breathing gas flow signal. The AD converter 1442 then converts the signal from the filter 1440 into digital form, which is received by the CPU 1444 for further processing and calculations. In some embodiments, the CPU 1444 can transmit the digital signal to the host monitor or other client device via the Bluetooth low energy processor 1160. In some other embodiments, the CPU 1444 transmits the digital signal to the communications module 1446 for wireless transmission to the host monitor or other client device. In some embodiments, the filter 1440 is configured to subtract the electrical signal detected by the thermistor 500-2 from the electrical signal detected by the thermistor 500-1. In some embodiments, the filter 1440 is configured to subtract the electrical signal detected by the thermistor 500-2 and the electrical signal detected by any of the nasal thermistor 400-1, the nasal thermistor 400-2, and the oral thermistor 400-3 from the electrical signal detected by the thermistor 500-1.

FIG. 36 illustrates a respiration sensor detection state table 1458 for determining the respiration sensor placement and function. For example, an operation logic is derived from the electrical signals from the thermistor 500-1, the thermistor 500-2, and the thermistor 400-1, 400-2, 400-3 to detect different states of the respiration sensor 100a, 100b. The different states of the respiration sensor 100a, 100b are utilized to identify sensor placement with respect to the patient and function of the sensor for monitoring and notifying of these states. The respiration sensor 100a, 100b is capable of identifying, for example, early signs of respiratory depression, spasms, obstructions, and other symptoms, and notifying of these identifications. In addition to notifying of such identifications, the respiration sensor 100a, 100b is also capable of notifying when an improper placement of the sensor is identified or detected to alert a caregiver to check on the patient and make sure that the sensor is not obstructing the patient's airways or otherwise disturbing the patient.

The respiration sensor 100a, 100b includes various detection states including, but not limited to: a not-yet-placed state (Not Yet Placed state 1460); a correctly-placed and measuring state (Correctly Placed & Measuring state 1462); a correctly-placed, but no breath state (Correctly Placed, No Breath state 1464); a loose device state (Loose state 1466); a detached or no breath state (Detached or No Breath state 1468), and an operating-temperature exceeded state (Operating Temperature Exceeded state 1470).

In the Not Yet Placed state 1460, the respiration sensor 100a, 100b is not yet placed on the patient. For example, when the respiration sensor 100a, 100b is turned on, but not yet placed on or attached to the upper lip of the patient, the thermistor 500-2, the thermistor 500-1, and the thermistor 400-3 all detect a similar signal corresponding to temperature proportional to ambient temperature and the breath indicator 1453a (shown in FIG. 35) detects no breaths.

Under these detected conditions, the respiration sensor 100a, 100b determines that it is in the Not Yet Placed state 1460 and will not transmit an alert notification.

After the respiration sensor 100a, 100b is placed on or attached to the upper lip of the patient, the thermistor 500-2 detects and adapts to a temperature close to skin temperature of the upper lip while the thermistor 500-1 remains detecting the ambient air temperature. In some embodiments, the temperature offset error in the thermistor 500-2, which is caused by, for example, a mustache, may be ignored since the temperature detection is enough to monitor the temperature change during the time it takes to detect or determine whether the sensor is in proper placement or not (e.g., not the absolute value). When the location of the sensor between the nasal and the oral passages of the patient is proper and the patient is breathing the thermistor 400-3 start to adapt to and detect the temperature of the sequentially changing gas flow (e.g., Breath). At this point, the breath indicator 1453a determines that the thermistor 400-3 detected a breath. Under these conditions, the respiration sensor 100a, 100b determines that it is in the Correctly Placed & Measuring state 1462 and will not transmit an alert notification.

The respiration sensor 100a, 100b determines that it is in the Correctly Placed, No Breath state 1464 when the thermistor 500-2 remains detecting and adapting to the skin temperature and the thermistor 500-1 remains detecting the ambient air temperature, but the thermistor 400-3 no longer sufficiently adapts or detects the gas flow temperature (e.g., detects ambient air temperature instead) even though the breath indicator 1453a detects breaths. In the Correctly Placed, No Breath state 1464, the location of the respiration sensor 100a, 100b between the nasal and/or oral cavities may be unsatisfactory and the gas flow through the sensor cavities may be insufficient and the respiration sensor 100a, 100b will transmit an alert notification indicating that "No Breath" is detected. It is also possible that, in the Correctly Placed, No Breath state 1464, the patient is not breathing sufficiently enough and needs immediate attention from clinical personnel.

The respiration sensor 100a, 100b determines that it is in the Loose state 1466 when the thermistor 500-2 does not detect the skin temperature and detects, instead, a similar value as the thermistor 500-1 (e.g., ambient air temperature) while the thermistor 500-1 remains detecting the ambient air temperature, the thermistor 400-3 detects the gas flow temperature, and the breath indicator 1453a detects breaths. In the Loose state 1466, the respiration sensor 100a, 100b may be positioned askew with respect to the upper lip of the patient, such that breathing gas flow is not properly detected or monitored, and the respiration sensor 100a, 100b will transmit an alert notification indicating that a "Loose Sensor" is detected so that care personnel may adjust the respiration sensor 100a, 100b with respect to the patient's upper lip.

The respiration sensor 100a, 100b determines that it is in the Detached or No Breath state 1468 when the thermistor 500-2, the thermistor 500-1, and the thermistor 400-3 all detect ambient air temperature and the breath indicator 1453a detects no breaths. In the Detached or No Breath state 1468, the respiration sensor 100a, 100b is detached from the patient and it will transmit an alert notification indicating "Sensor Detached." In some embodiments, in the Detached or No Breath state 1468, in addition to or alternatively, the respiration sensor 100a, 100b will transmit an alert notification indicating that "No Breath" is detected.

The respiration sensor 100a, 100b determines that it is in the Operating Temperature Exceeded state 1470 when temperature detected by the thermistor 500-1 equals or exceeds the temperature detected by the thermistor 500-2. This means that the ambient temperature is too close to the breathing gas temperature to give sufficient differential temperature readings, which is proportional to the respiration signal amplitude. Such a situation may occur when the patient is lying face downward against a surface (e.g., bed or pillow). In the Operating Temperature Exceeded state 1470, the respiration sensor 100a, 100b will transmit an alert notification indicating an "Operating Error."

In some embodiments, signals from the nasal thermistors 400-1, 400-2 are compared to determine a state of the patient or the respiration sensor 100a, 100b. The signal from the nasal thermistors 400-1, 400-2 can be compared relative to each other to determine if the respiration sensor 100a, 100b is correctly placed on the patient. For example, a normal signal from thermistor 400-1 or 400-2, and a low or non-existent signal from the other of thermistor 400-1 or 400-2, can indicate that the respiration sensor 100a, 100b is not positioned correctly relative to the patient's nostrils.

The capacitive sensor 1401 can also be used to activate and/or turn on the respiration sensor 100b. In some embodiments, the processor can be set into a low power or sleep mode when the respiration sensor 100b is in storage or not in use. When in the sleep mode, the respiration sensor 100b can process a measured value from the capacitive sensor 1401 and compare the measured value to a previous value stored into the memory. The previous value stored into the memory can correspond to a respiration sensor 100b that is not engaged against a patient's face. When the respiration sensor 100b is placed on a patient's upper lip, the capacitive value measured by the capacitive sensor 1401 can change. The change of capacitive value can be caused by the capacitive sensor 1401 engaged against the patient's lip or tissue, which can have a different permeability relative to another material such as the capacitive sensor 1401 packaging or ambient air.

When a change in measured value from the capacitive sensor 1401 is detected, the processor can change the sensor from the low power or sleep mode to a normal operating mode. In some embodiments, the processor can activate other electrical circuits on the electronics board when a change in measured value from the capacitive sensor 1401 is detected. In some embodiments, when the respiration sensor 100b is separated from the face of a patient, and a measured value from the capacitive sensor 1401 corresponds to a respiration sensor that is not engaged against a patient's face, the respiration sensor 100b can turn off. In some embodiments, the respiration sensor 100b can turn off when the capacitive sensor 1401 detects a change back to the permeability of, for example, air and/or no breathes are detected. In some embodiments, the respiration sensor 100b can wait for a predetermined safety time limit, e.g., 5 minutes, and then turn off or enter a low power mode.

In some embodiments, the respiration sensor 100a, 100b can begin measurement automatically when the processor counts one or more breaths from any of the nasal and oral thermistors. For example, measurement can start automatically when the processor counts three different successful breaths from the nasal and/or oral thermistors.

To determine the respiration sensor placement and function, the electronics board 300 can include, for example, any of a Bluetooth low energy processor 1160, the temperature-to-voltage converter 1438, the filter 1440, the AD converter 1442, the CPU 1444, the communications module 1446, and the breath indicator 1453a stored in the memory 1453b.

The amplitude of the alternating electrical voltage signal from the thermistors 400-1, 400-2, 400-3, 500-1, 500-2 can be converted proportional to a real temperature, for example into degrees of Celsius. In principle, when the patient breathes normally, the minimum amplitude of electrical signal from the NTC type thermistors is proportional to the maximum temperature of exhaled air and the maximum amplitude of electrical signal from the NTC type thermistors is proportional to the minimum temperature of inhaled ambient air. For the PTC type thermistors, the maximum amplitude of electrical signal is proportional to the maximum temperature of exhaled air and the minimum amplitude of electrical signal is proportional to the minimum temperature of inhaled ambient air. The conversion from electrical voltage signal to temperature is negative with NTC type thermistor, whereas the conversion from electrical voltage signal to temperature it is positive with PTC type thermistor. Accordingly, both NTC and PTC type thermistors can provide the same temperature value.

Figure 37:
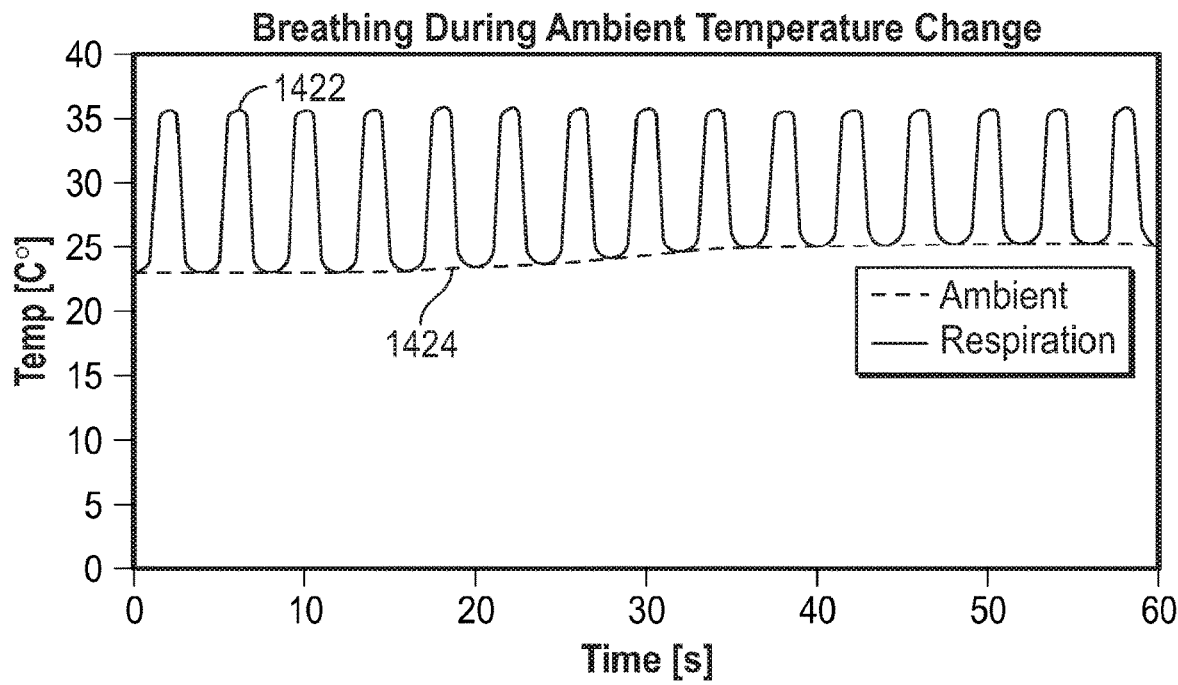
FIG. 37 illustrates a graph showing breathing during changes in ambient air temperature, according to some embodiments.

FIG. 37 illustrates the temperature of breathing (respiratory flows) during changes in ambient air temperature. The amplitude of the alternating breathing signal 1422 indicates a temperature difference between inhaled ambient air and exhaled gas from the lungs in degrees of Celsius [C° ], and can be proportional to a strength of breathing or volume and flow of breathing. The peak-to-peak amplitude of alternating breathing signal 1422, presented in degrees of Celsius [C° ], depends mostly on the flow rate of gas and ambient air temperature 1424. As can been seen in FIG. 37 the peak-to-peak amplitude of the breathing signal 1422 decreases when the ambient air temperature 1424 increases.

In some instances, if exhaled breathing gas flow and volume decreases, the measured signal amplitude decreases proportionally. Due to lower gas volume there is less thermal energy, and due to lower gas flow speed, exhaled gas has more time to release thermal energy to surrounding air and sensor housing (e.g., housing 2001) before reaching the thermistor 400-1, 400-2, 400-3. Additionally, the exhaled gas can have less thermal energy to warm up the thermistor 400-1, 400-2, 400-3.

In some instances, if ambient air temperature decreases, the exhaled gas releases even more energy due to higher energy difference between two gas mediums. On the other hand, the maximum breathing signal is proportional to ambient temperature, and is sensitive to ambient air temperature changes, thus the peak-to-peak signal amplitude proportional to sequentially changing inhaled and exhaled gas is also dependent on ambient air temperature. In some instances, if ambient air temperature increases, the breathing signal amplitude between inspirations and expirations decreases and, vice versa, the breathing signal amplitude between inspirations and expirations increase when ambient air temperature decreases.

Figure 38:
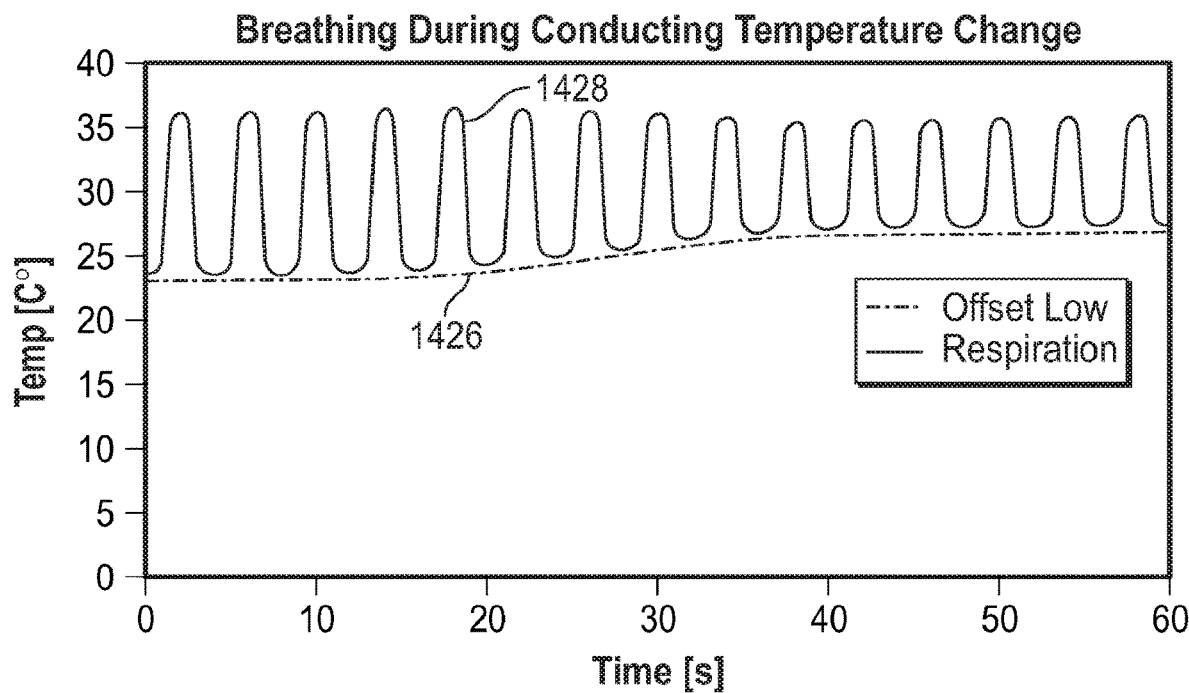
FIG. 38 illustrates a graph showing breathing during conducting temperature changes, according to some embodiments.

In some embodiments, energy in the form of heat from a patient's upper lip can be conducted through the respiration sensor housing to thermistors. In some instances, energy directed from or toward a gas flowing through the respiration sensor 100a, 100b can cause a similar effect as ambient air change. FIG. 38 illustrates breathing (respiratory flows) during a change in thermal energy conducting temperature, for example when the respiration sensor 100a, 100b is coupled to a patient's face. The sensor housing (e.g., housing 2001) that guides gas flow through the respiration sensor 100a, 100b is preferably made of plastic, silicon, or similar material with low thermal coefficient to minimize its ability to absorb, store, and conduct thermal energy. However, the housing may conduct some thermal energy from patient's upper lip and elevate the sensor temperature, similar to ambient temperature change. The change in temperate generates a small offset, represented by offset curves 1426, to the temperature signal 1428 proportional to inhaled ambient air temperature decreasing the breathing signal peak-to-peak amplitude. The thermistor 400-1, 400-2, 400-3 senses when thermal energy, stored during expiration, is released during inspiration, and senses when thermal energy is released during the expiration phase, thus decreasing the breathing signal peak-to-peak amplitude between inspired and expired phases. This offset, represented by the offset curves 1426, can dependent on any of the ambient air temperature and the thermal coefficient of the sensor housing's material, which is a constant based on laboratory measurement and can be taken into account. The thermal energy conducting from a patient's upper lip through the sensor housing is strongly dependent on the thermal connection between the respiration sensor 100a, 100b and the patient's face, which in turn is proportional to temperature and the electrical signal from the thermistor 500-2.

When the respiration sensor has been placed on patient's face, each of the inlets to the nasal flow passage cavities can be separated from the corresponding nasal outlet of the patient, and the inlet to the oral flow passage cavity can be separated from the corresponding oral outlet of the patient (i.e., mouth). When the patient breathes, warm and moist breathing gas flows through any of the nasal and oral flow passages. Warm and moister exhaled breathing gas releases thermal energy into the ambient air if the ambient air temperature is lower than the exhaled air temperature. The temperature of exhaled air decreases as shown in FIG. 38 represented by the offset curves 1426, which decreases the breathing signal amplitude. To get maximal breathing signal amplitude during exhalation, the sensor housing or respiration sensor cavities are positioned as close as possible to patient's nasal and oral passage cavities.

It can be important to have accurate breathing signal peak to peak amplitude proportional to patient's actual inspired and expired breathing efforts at any time and during any condition to be able to detect situations, such as, for example, opiates deteriorating patient's breathing, obstructions, bronchospasms, etc. Changes in ambient air temperature and in conducting thermal energy may cause a decrease in the peak-to-peak signal amplitude, which resembles a similar decrease, for example, as when opiates deteriorate the patient's breathing. In order to correctly identify or detect the cause of the decrease and to avoid a misidentification, such error signals can be compensated and eliminated to prevent any false notifications of these error signals. Ambient air temperature changes that decrease the breathing gas signal can be compensated and eliminated based on the temperature signal proportional to the thermistor 500-1 sensitive to the ambient temperature. Compensation to the breathing gas signal is inversely proportional to increases in the ambient air temperature, thus if the ambient air temperature increases, then the gain of the breathing gas signal is increased, and vice versa. Similarly, changes in skin temperature, which is proportional to the conducting temperature through the sensor housing 2001, also decrease the breathing gas signal and is compensated and eliminated based on the temperature signal proportional to the thermistor 500-2 sensitive to the skin temperature. Compensation to the breathing gas signal is inversely proportional to increases in the skin temperature, thus if the skin temperature increases, then the gain of the breathing gas signal is increased, and vice versa.

In some embodiments, thermal transients can be eliminated and signal amplitude relative to ambient and thermal energy conducting temperatures can be compensated to produce a respiratory flow signal. For example, after removing the thermal effects as discussed above with reference to FIG. 35, the breathing gas flow signal may be displayed at the host monitor or other client device. The accuracy and resolution of the breathing gas flow signal is enhanced due to the elimination of the thermal transients and compensating the signal amplitude relative to the ambient and conducting temperatures.

In some embodiments, a temperature is detected via the thermistor 500-2 when the respiration sensor 100a, 100b is initially placed on a patient's upper lip. Small sensors placed on the patient's airways or close to airways may block the airways if the sensor detaches or the attachment is loose. Some conventional approaches to mitigate the possibility of the sensor from detaching or becoming loose are to increase the size of the sensor and increase the adhesive area stuck to the skin. Larger sized sensors, however, may be uncomfortable for a patient and the increase in adhesive may irritate the skin of the patient, such that the patient may intentionally or unintentionally remove or detach the sensor. Some other conventional approaches may utilize a notification system when the sensor becomes detached. In such approaches, however, care personnel may experience "alarm fatigue" caused by false alarms. The disclosed respiration sensor 100a, 100b determines different suitable measurement parameters that are used to specify different situations to generate appropriate notifications.

For example, when the respiration sensor 100a, 100b is turned on, but is not yet placed on or attached to the patient's face, the thermistor 500-1, the thermistor 500-2, and the thermistor 400-3 detects ambient air temperature. Additionally, data for a breath indicator 1453a can be stored in a memory 1453b associated with the CPU 1444, and can indicate that no breaths have been detected yet by the thermistors 400. While the memory 1453b is illustrated to be included in the CPU 1444, it can be a separate element. When the respiration sensor 100a, 100b is placed on the patient's upper lip, the thermistor 500-2 comes into close contact with or makes contact with the skin of the upper lip and begins detecting the skin temperature on the patient's upper lip as represented by a skin temperature curve. For example, at zero seconds, the thermistor 500-2 detects the ambient air of approximately 23° C. and warms up after the respiration sensor 100a, 100b is placed on the upper lip of the patient, at approximately 8 seconds, to detect the skin temperature of approximately 35.5° C. at 55 seconds. Accordingly, when the respiration sensor 100a, 100b is removed or loosened from the skin on the patient's upper lip, the thermistor 500-2 adapts and begins detecting the ambient temperature.

In some embodiments, a temperature offset error may be induced to the thermistor 500-2 to compensate for any space between the thermistor 500-2 and the patient's upper lip, such as a mustache or similar medium. As a result, the temperature detected by the thermistor 500-2 may differ from the actual skin temperature. However, this compensation or adjustment may be tolerated as it may be important only to detect the temperature change. For example, when the respiration sensor 100a, 100b is placed on the patient's upper lip the thermistor 500-2 monitors or detects the temperature trend over time until detection of removal of the respiration sensor 100a, 100b rather than measuring or detecting the absolute skin temperature value.

In some embodiments, a temperature is detected via the thermistor 500-1 during ambient temperature change. The thermistor 500-1 monitors or detects the ambient temperature. For example, on an ambient temperature curve, the thermistor 500-1 detects an initial ambient temperature of approximately 23° C. at zero seconds and detects a new ambient temperature of approximately 25° C. at 55 seconds when, for example, the patient is transferred from an ambulance to a hospital environment.

In some embodiments, a temperature is detected via the thermistor 400-1, 400-2, 400-3 during respiratory flows. The thermistor 400-1, 400-2, 400-3 sequentially detects the temperature change of the breathing gas flow between exhaled breathing gas and inspired ambient air at a constant ambient temperature of 25° C., as represented by a respiration temperature curve. During expiration, exhaled humid and warm air flows out from the nasal and/or the oral passages of the patient into the cavity, such as, for example, the nasal flow passages 301 and the oral flow passage 302, inside the sensor housing (e.g., housing 2001) causing temperature of the thermistor 400-1, 400-2, 400-3 located inside the cavity to adapt to the exhaled gas flowing past the thermistor 400-1, 400-2, 400-3. During inspiration, the patient inhales causing the ambient air to flow through the cavity, such as, for example, the nasal flow passages 301 and the oral flow passage 302, inside the sensor housing (e.g., housing 2001) towards the oral and/or nasal passages of the patient, at which point, the thermistor 400-1, 400-2, 400-3 adapts back to the temperature of inhaled ambient air flowing past the thermistor 400. Thus, during expiration, the air flowing out from the lungs warms up the thermistor 400-1, 400-2, 400-3 and, during inspiration, the ambient air cools down the thermistor 400-1, 400-2, 400-3. The temperature difference between the inhaled ambient air and the exhaled breathing gas decreases and approaches zero when the temperature of the ambient air approaches the temperature of the exhaled breathing gas. When the temperature of the inhaled ambient air exceeds the temperature of the exhaled breathing gas the temperature difference exceeds zero again, but changes its sign.

In some embodiments, continuous, real time measurements of respiratory flows is determined. Accordingly, a curve indicates a respiration real time waveform. Accordingly, the curve is a waveform including more than two breathing cycles, each cycle including an expiration phase (positive amplitude) and an inspiration phase (negative amplitude). A respiration rate (RR) curve is a curve indicating a value of breaths per minute [bpm]. It can be calculated from respiration waveform curve according to equation RR=60 seconds/breathing cycle time [seconds]. Each respiration cycle has respiration magnitude that may be calculated from a difference between maximum amplitude of expiration and minimum amplitude of inspiration (which is negative). In some embodiments, respiration magnitude is proportional to a breathing flow rate. When a patient exhales, the warm, moist breathing gas from the lungs warm up thermistors 400-1, 400-2, 400-3 causing respiration waveform signal curve to rise. During inspiration, ambient air cools down thermistors 400-1, 400-2, 400-3 to a temperature close to the ambient air temperature. Thus, the breathing cycle amplitude is proportional to breathing gas flow rate or respiration magnitude, which is proportional to a temperature change of thermistors caused by the cooling/warming effects of inspiratory and expiratory air flowing past the thermistors. In the particular case of curve, respiration magnitude is a value in percentages indicating the breathing flow magnitude or rate, relative to a maximum breathing flow magnitude or a maximum rate for a particular patient.

In some embodiments, a respiration rate over an extended period of time may be monitored and fit to a curve. The curve may indicate a respiration magnitude, corresponding to the depth of breath, over an extended period of time. In some embodiments, curves may reflect both respiration rates and magnitude values calculated on a breath to breath basis. In some embodiments, the curves may include average values to reduce large fluctuations in signals received from sensors. In some embodiments, respiration rate and variance may be desirable parameters for detecting an upcoming heart stroke. In some embodiments, a breathing signal variance may anticipate a stroke event approximately 6-8 hours before the actual stroke. Similarly, overdose of opioids, or pain (e.g., too little opioids) may cause changes in respiration variance that are detectable in a respiration sensor, leading to quicker response and treatment to mitigate or prevent the impending risk.

VI. Accelerometer Functions

Figure 39:
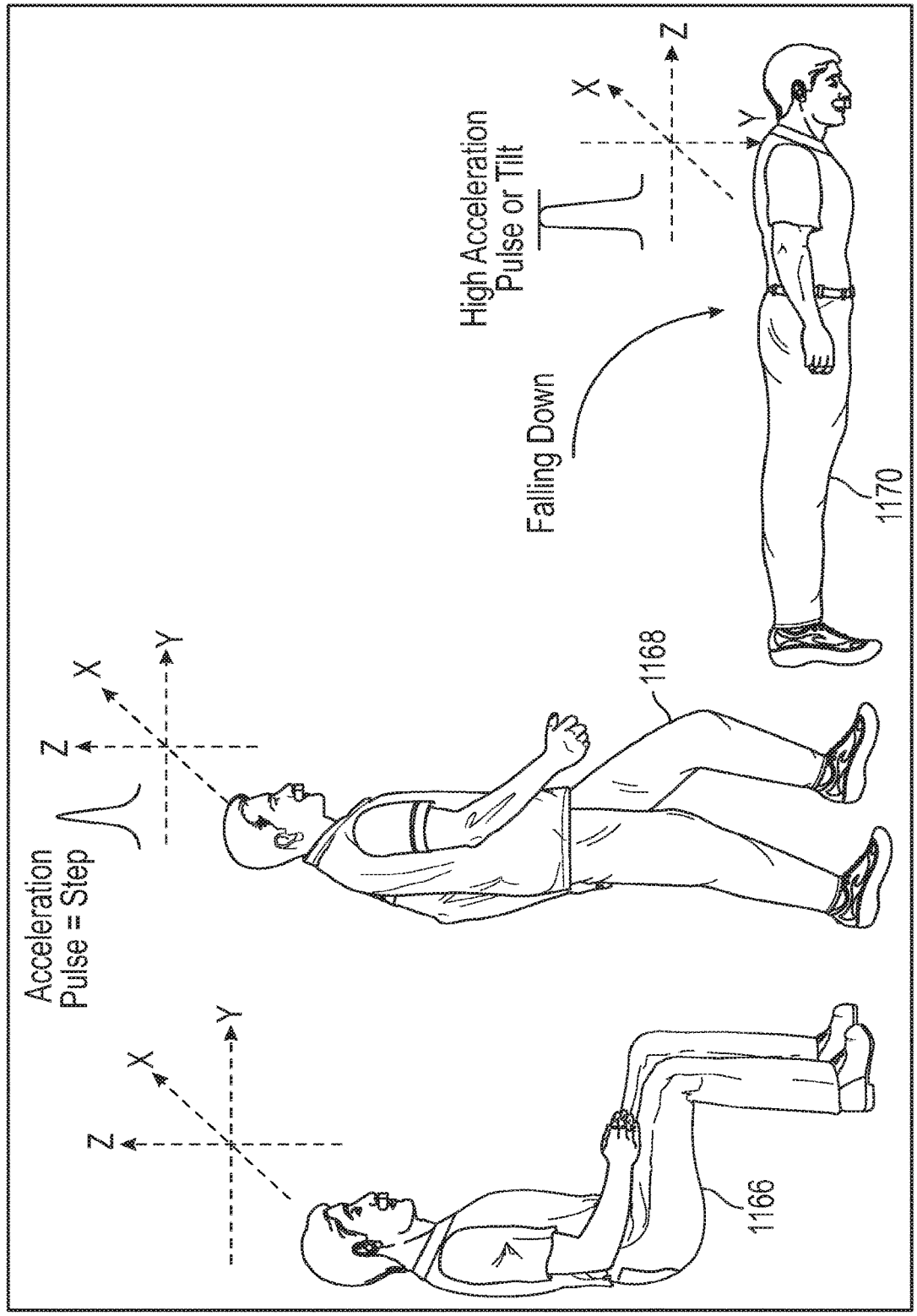
FIG. 39 illustrates a respiration sensor in use on a patient transitioning from a seated position, to a moving position, to a fallen position, according to some embodiments.

Referring to FIG. 39, the respiration sensor 100a, 100b can provide, for example, body position, movement, and fall detection via the accelerometer 1150 (shown in FIG. 33). The accelerometer 1150 measures or detects acceleration, position, angular rotation and other parameters derived from electrical signals proportional to at least x-, y-, and z-axes directions of accelerometer 1150 and can detect the patient's position and movement, the patient's head position and movement, acceleration caused by movement of the respiration sensor 100, 100b, 100c, and movement of patient's upper lip while talking or movement of the patient's heart. For example, the electrical signals from the accelerometer 1150 can be sent or transmitted to a monitoring device, such as a host monitor or similar client device, via Bluetooth or other communication method to monitor mobile patients. In some embodiments, the accelerometer 1150 of the respiration sensor 100a, 100b is a three-dimensional accelerometer that measures acceleration and position of at least x-, y-, and z-axes directions of the accelerometer 1150 as well as rotation around at least these three axes.

As discussed above, the respiration sensor 100a, 100b detects movement and position to monitor, for example, that the respiration sensor 100a, 100b has not fallen out of place with respect to the patient, that the patient has not fallen, or that the orientation of the patient's head is not obstructing the nasal and oral breathing gas flows (e.g., patient's face is downward towards pillow or bed). For example, it is desirable to obtain information about how a patient's head is positioned when the patient is lying in bed for determining the measurement of respiratory cycles from patients. When the patient is lying down on his/her back with his/her face upwards the patient can, for example, turn his/her head from left to right. In such a position, the patient can breathe in a manner that allows gas to flow freely through the nasal and/or oral cavities of the respiration sensor 100a, 100b. When the patient is lying sideways, his/her head can turn upward or downward. In this sideways position, it possible for the patient's head to face sideways or upward, such that the patient can breathe in a manner that allows gas to flow freely through the nasal and/or oral cavities of the respiration sensor 100a, 100b. It is also possible, however, in this sideways position, for the patient to turn his/her head downwardly toward the bed or a pillow, such that the gas does not flow freely or is obstructed through the nasal and/or oral cavities of the respiration sensor 100a, 100b. This uneven gas flow or obstruction of gas flow can disturb the measurement signal proportional to breathing or the patient's breathing may be prevented or deteriorated. A similar result may occur when the patient is laying on his/her stomach with his/her face downward into the bed or the pillow.

In such scenarios, the respiration sensor 100a, 100b may detect the direction in which the patient's face is pointing via the accelerometer 1150, which can also measure or detect the axial and/or angular position. The position of the patient's head is determined or calculated from the electrical signals in the x-, y-, and z-directions detected via the accelerometer 1150. In some embodiments, the respiration sensor 100a, 100b determines, via the signals proportional to the patient's position that are monitored by the accelerometer 1150, the position of the patient's head relative to the respiration sensor 100a, 100b. As a result, the respiration sensor 100a, 100b, responsive to determining that the patient's head is in a position that inhibits or obstructs gas flow therethrough and/or causes the respiration sensor 100a, 100b, to function improperly, can transmit a notification to inform of such positioning to the host monitor or other client device via Bluetooth or other communication method.

FIG. 39 illustrates the respiration sensor 100a, 100b in use on a patient to identify or detect any of a seated position 1166, a moving position 1168, and a fallen position 1170. In some embodiments, the respiration sensor 100a, 100b can identify or detect transitioning of a patient between any of a seated position 1166, a moving position 1168, and a fallen position 1170. In some scenarios, the patient may be mobile (e.g., getting up from the bed to use the restroom) and it may be desirable to monitor the patient's movement and position. For example, the patient may be recovering from a health issue and feel dizzy when getting up from a stationary position, such that the patient may pass out, fall down, or hurt himself/herself and require acute medical attention and care. In some embodiments, the respiration sensor 100a, 100b detects, via the signals proportional to the patient's position that are monitored by the accelerometer 1150, such situations and indicates or transmits a notification to inform or alert the host monitor or other client device via Bluetooth or other communication method.

As an example, the patient may be in a seated position 1166 and stand up to an upright position 1168, such that the accelerometer 1150 detects movement of the patient's head via the electrical signals in the x-, y-, and z-directions. Further, as the patient moves or walks in the upright position 1168, the accelerometer 1150 detects each step or movement the patient may make, such as when the patient gets out of bed to go to the restroom. Each step generates acceleration pulses that are detected by the accelerometer 1150 via the electrical signals proportional to acceleration in the x-, y-, z-directions. If the patient happens to fall down to the fallen position 1170, the accelerometer 1150 detects a high acceleration value proportional to a falling down magnitude. With the patient in the fallen position 1170 (e.g., lying on the floor) from the upright position 1168, the respiration sensor 100a, 100b determines that the patient has fallen down due to the accelerometer 1150 detecting a high acceleration value and determining the difference in the patient's head position in the upright position 1168 and the fallen position 1170. Responsive to the determination that the patient has fallen down, the respiration sensor 100a, 100b, transmits a notification to inform or alert the host monitor or other client device, via Bluetooth or other communication method, that the patient has fallen down and may require immediate medical care.

Additional measurements can be made based on movement of a patient's upper lip when patient talks. Talking is vibration of air coming from vocal cords and it may disturb the breathing gas flow measurement and the calculation of respiration rate (RR). The movement of the upper lip may be detected and indicate that the patient is talking. In some embodiments, movement of a patient's upper lip is detected by the accelerometer 1150.

Figure 40:
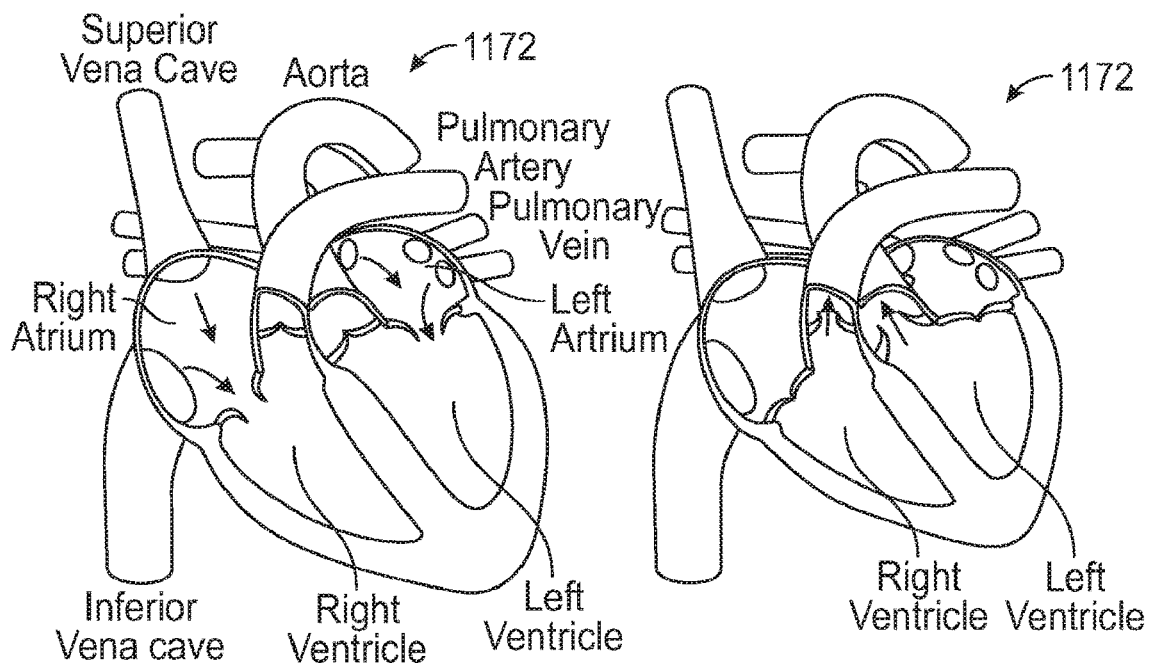
FIG. 40 illustrates a front plan view of a heart and directions of blood circulation therethrough.

Additional measurement can be made based on movement of a patient's heart. The measurements can be used to determine a heart rate of the patient. FIG. 40 illustrates blood circulation through a heart 1172 as the heart 1172 pumps blood through the body 1174, shown in FIG. 41. Blood from the systemic circulation enters the right atrium from the superior and inferior vena cava and passes to the right ventricle. From the right ventricle, blood is pumped into the pulmonary circulation, through the lungs. Blood then returns to the left atrium, passes through the left ventricle and is pumped out through the aorta back to the systemic circulation. Normally, with each heartbeat, the right ventricle pumps the same amount of blood into the lungs as the left ventricle pumps to the body. Arteries transport blood away from the heart. The heart 1172 contracts at a resting rate close to 72 beats per minute.

Figure 41:
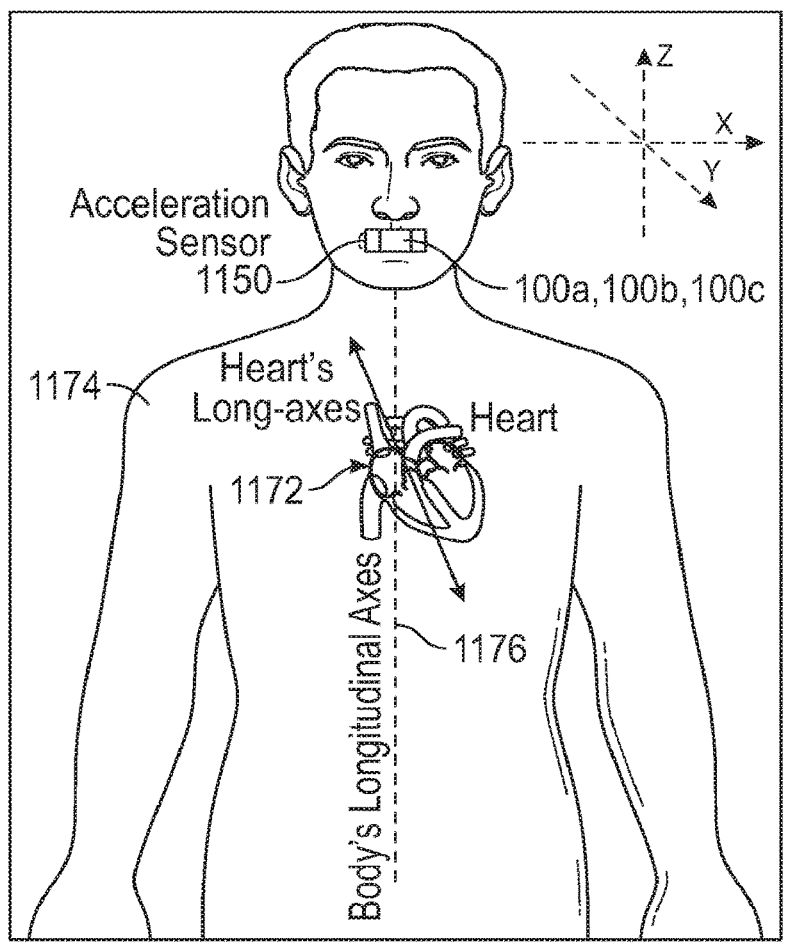
FIG. 41 illustrates a front plan view of a respiration sensor including an accelerometer for detecting body movement of a patient utilizing the respiration sensor, according to some embodiments.

Due to a specific orientation of the myocardial fibers, in a heartbeat cycle, the heart 1172 makes a wringing or twisting motion along its long-axis. On the other hand, the heart's sequential contraction, which allows superior and inferior blood to enter the right atrium and ventricle as well as allows expansion to pump blood from the left ventricle and the atrium back to the systemic and pulmonary blood circulation, generate micro movement along heart's long-axis. This back and forth movement is slightly leaned to the right regarding the body's longitudinal axis 1176, as illustrated in FIG. 41.

The heart's movement moves the whole body 1174 back and forth cyclically at the phase of a heartbeat close to the direction along body's longitudinal axis 1176. This micro movement can be detected by the accelerometer 1150 of the respiration sensor 100a, 100b. The most sensitive direction for the accelerometer 1150 to detect would be the z-axis. In some embodiments, the accelerometer 1150 contains an angular motion sensor or sensing elements, in addition or alternatively, such that it can be used to detect the heart's rotation along its long-axis, which also generates rotational force around body's longitudinal axis 1176 at a phase of the heartbeat. Either or both the body's longitudinal movement or rotational movement around the body's longitudinal axis 1176 can be transformed to a heartbeat or heartbeats per minute value from the electrical signals of accelerometer. This heart rate (HR) information can be used together with the respiration rate (RR) and flow information, by the respiration sensor 110a, 100b, in early detection and prevention of respiratory depression and other symptoms.

In some embodiments, the accelerometer 1150 can also detect rise and fall of a patient's chest or other thoracic movement. This information can be coupled with at least one of HR, RR, and other breath indicators to aid in early detection and prevention of respiratory distress and other illnesses.

VII. EtCO2 Surfaces

Figure 42A:
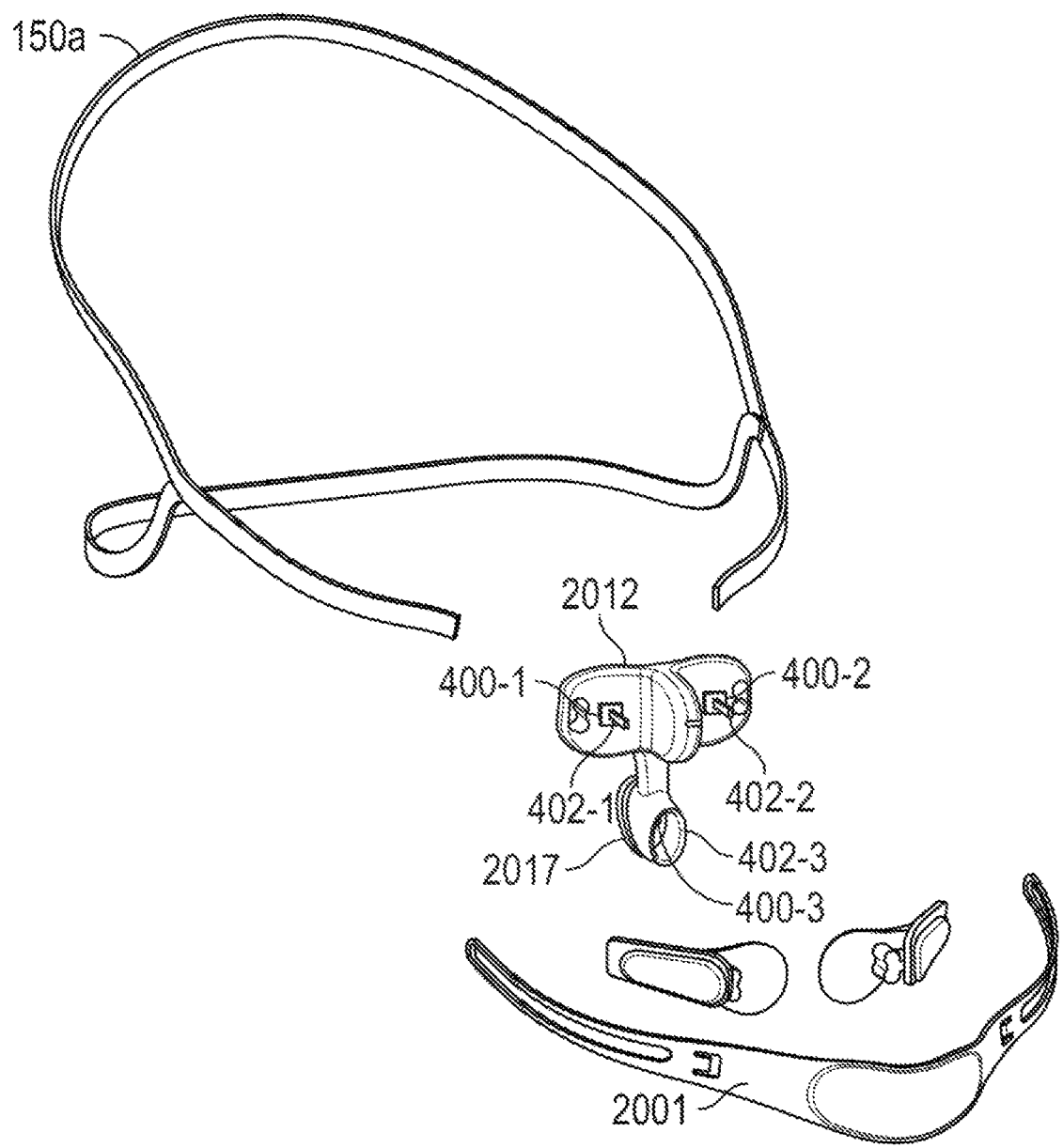
FIG. 42A illustrates a front perspective exploded view of a respiration sensor having end-tidal CO2 (EtCO2) sensitive surfaces, according to some embodiments.

In some embodiments of the present disclosure, the respiration sensor, such as, for example, the respiration sensor 100a, 100b, can include end-tidal CO2 (EtCO2) sensing features. The EtCO2 sensing features can include one or more EtCO2 sensitive surface. The one or more EtCO2 sensitive surface can be positioned on an outer surface of the shroud 2012 and on a surface of the oral shroud 2017. FIG. 42A shows a first EtCO2 sensitive surface 402-1 positioned on an outer surface of the shroud 2012 and adjacent to the thermistor 400-1, a second EtCO2 sensitive surface 402-2 positioned on an outer surface of the shroud 2012 and adjacent to the thermistor 400-2, and a third EtCO2 sensitive surface 402-3 positioned on an inner surface of the oral shroud 2017 and adjacent to the thermistor 400-3.

The EtCO2 sensitive surface can change color as a result of nasal and/or oral breath detection of CO2. For example, the EtCO2 sensitive surface can change color to indicate the presence of CO2. In some embodiments, the one or more EtCO2 sensitive surface is coupled with an electrode. As nasal and/or or oral breath moves over the EtCO2 sensitive surface, a change in resistance can occur. The change in resistance is used to determine the presence of CO2 or other breathing related conditions. In some implementations, one or more EtCO2 sensitive surfaces may be included in an electronics board of a sensor, such as the electronics board 300, as shown in FIG. 42B.

Figure 42B:
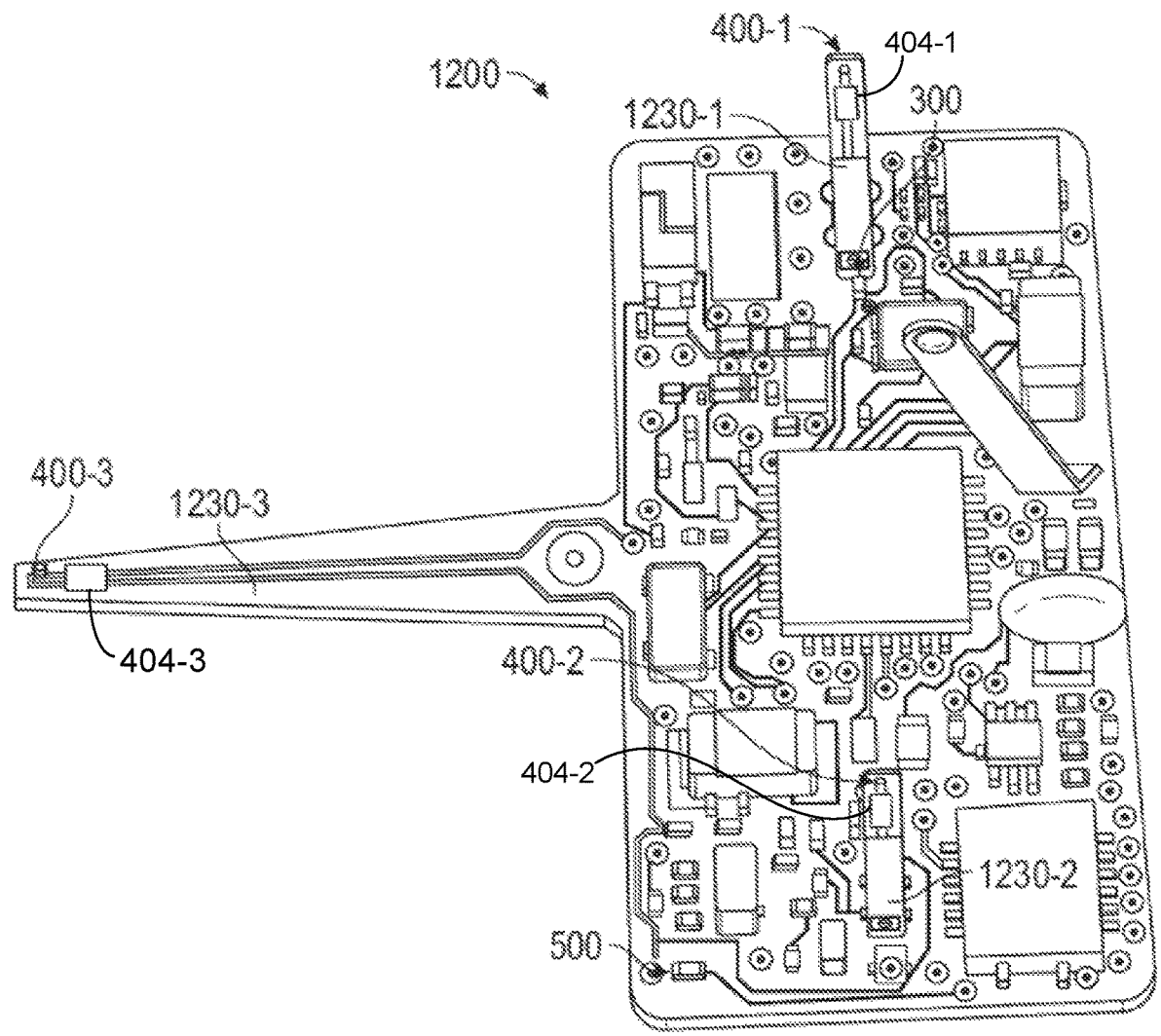
FIG. 42B illustrates a top perspective view of an electronics board of a respiration sensor having EtCO2 sensitive surfaces, according to some embodiments.

Turning now to FIG. 42B, there is shown EtCO2 sensitive surfaces 404-1, 404-2, 404-3 electrically coupled to the electronics board 300 via one or more electrical contacts of the electronics board 300. In some implementations, one or more EtCO2 sensitive surfaces 404-1, 404-2, 404-3, collectively referred to as EtCO2 sensitive surfaces 404, may be sprayed on a surface of one or more components of the electronics board 300. For example, EtCO2 sensitive surface 404-1 may be sprayed on support structure 1230-1, EtCO2 sensitive surface 404-2 may be sprayed on support structure 1230-2, and EtCO2 sensitive surface 404-3 may be sprayed on support structure 1230-3.

When sprayed on a surface of one or more components of the electronics board 300, the EtCO2 sensitive surface may be sprayed on to overlap a cathode electrical contact and an anode electrical contact of the component. For example, when EtCO2 sensitive surface 404-1 is sprayed on support structure 1230-1, the EtCO2 sensitive surface 404-1 may be sprayed on to overlap a cathode electrical contact and an anode electrical contact of the support structure 1230-1. Similarly, when the EtCO2 sensitive surfaces 404-2, 404-3 are sprayed on support structures 1230-2 and 1230-3, respectively, the EtCO2 sensitive surfaces 404-2 and 404-3 overlap cathode electrical contact and an anode electrical contact of the support structures 1230-2 and 1230-3 respectively. In some implementations, the EtCO2 sensitive surfaces 404, may be coupled to one or more electrodes of the electronics board 300. For example, EtCO2 sensitive surfaces 404-1 may be coupled to one or more electrodes of the support structure 1230-1, EtCO2 sensitive surfaces 404-2 may be coupled to one or more electrodes of the support structure 1230-2, and EtCO2 sensitive surfaces 404-3 may be coupled to one or more electrodes of the support structure 1230-3.

Each EtCO2 sensitive surface 404 forms an electrochemical cell. As described above, as nasal and/or or oral breath moves over an EtCO2 sensitive surface 404, a change in resistance can occur. The EtCO2 sensitive surfaces 404 may be configured such that a change in resistance may be proportional to the content of CO2 molecules in the nasal and/or oral breath that moved over the EtCO2 sensitive surfaces 404. The EtCO2 sensitive surfaces 404 may be coupled to an electrical circuit and the change in resistance can be transformed to a corresponding voltage via the electrical circuit. The voltage value may be transmitted to the central processing unit on the electronics board 300. In some implementations, the central processing unit on the electronics board 300 may be configured to determine the presence of CO2 and/or other breathing related conditions based on the change in resistance and/or corresponding voltage. In some implementations, the change in resistance and/or corresponding voltage may be transmitted to one or more electronic devices coupled to the sensors 100a, 100b, 100c, such as the monitoring devices described herein (e.g., hub 4, monitor 6, and the like).

VIII. Interconnectivity

Figure 43:
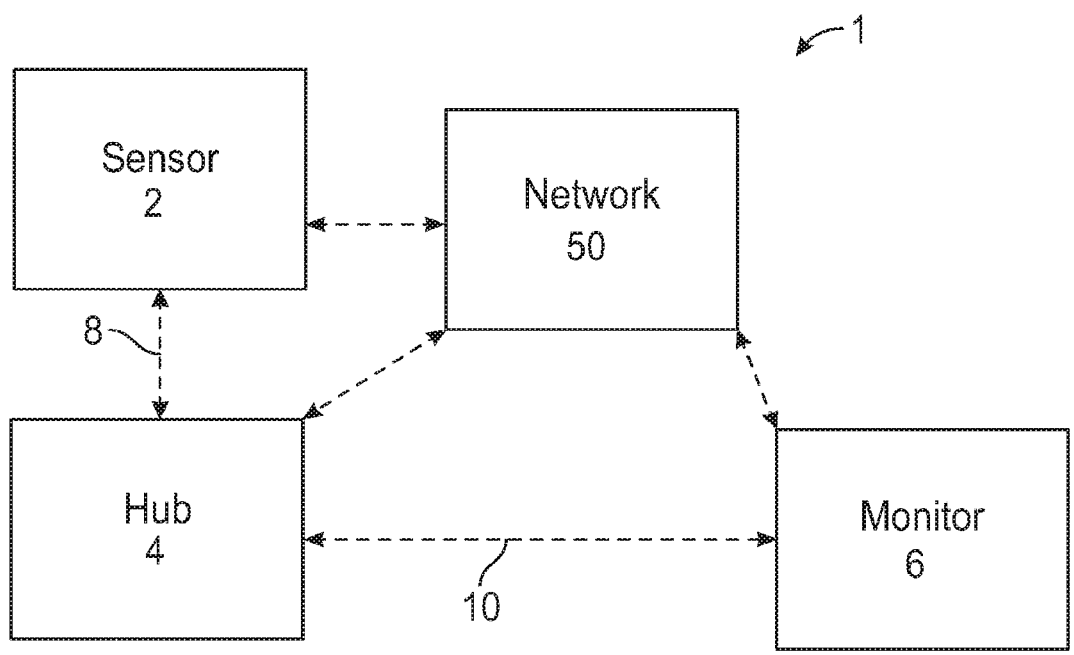
FIG. 43 illustrates a schematic view of a respiration monitoring system, according to some embodiments.

Referring to FIG. 43, a respiration monitoring system 1 is illustrated including a sensor 2, a hub 4, and a monitor 6. The sensor 2 may be the previously described sensor 10 or similarly configured as the previously described sensor 10. The sensor 2 may include one or more of the sensors described herein including, for example, sensor 100a and/or sensor 100b. The sensor 2, hub 4, and monitor 6 can be in communication with each other with wires or wirelessly. In some embodiments, any of a sensor 2, a hub 4, and a monitor 6 can be in communication with each other and with a network 50. The network can include, for example, any of a local area network (LAN), a wide area network (WAN), the Internet, a remote or cloud server, and the like. Further, network 50 can include, but is not limited to a network topologies, including any of a bus network, a star network, a ring network, a mesh network, a star-bus network, tree or hierarchical network, and the like. Although one sensor 2, hub 4, and monitor 6 are shown, it should be understood that the respiration monitoring system can include multiple sensors 2, hubs 4, and monitors 6.

Some embodiments of the respiration monitoring system can include a patient inside a hospital, a patient at home (e.g., homecare), and other original equipment manufacturer (OEM) applications. Accordingly, in some embodiments OEM parameters can be added to monitoring system (i.e., SpO2, Temp, NiBP, ECG etc.)

Communication between the sensor 2 and any of a hub 4 and a monitor 6 can be established using low energy communication 8, such as Bluetooth. A hub near the respiration sensor, for example, attached to or near a patient, can enable longer respiration sensor operation time by using low energy communication 8. The low energy communication 8 can include any of a wireless personal area network technology or Bluetooth. The hub can also provide respiration sensor pairing with patient, which can help secure patient identification information. Further, the use of a hub 4 with the sensor 2 can permit patient mobility and continuous monitoring throughout the hospital.

A long distance communication 10 protocol (e.g., Wi-Fi, cellular or other communication) may provide data transfer between the hub 4 and a monitor 6. In some embodiments, data can transfer between the hub 4 and a monitor 6 through the network 50. In some embodiments, the sensor 2 communicates with a hub in the form of a smartphone. The smartphone communicates to internet through Wi-Fi or cellular systems. Data can be transferred and saved into a cloud in real time. Patient data can be viewed in a different physical location in real time with a smartphone, a tablet, a laptop or desktop computer, a smart TV, and the like.

Figure 44:
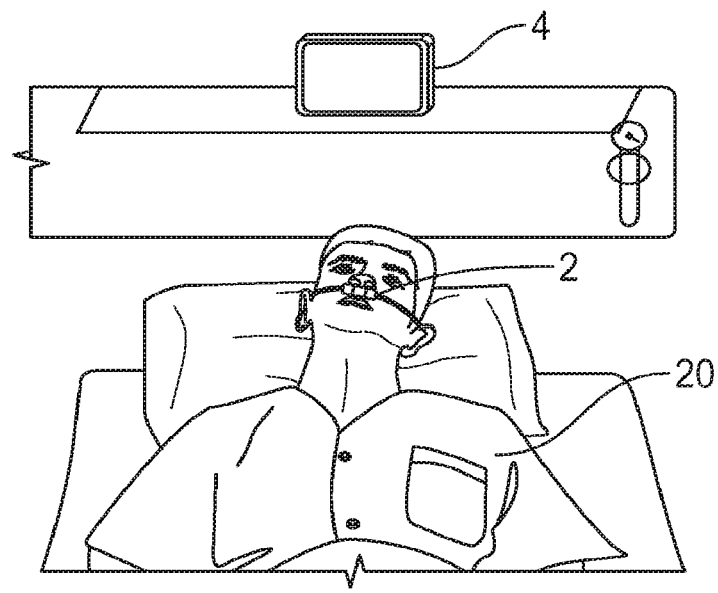
FIG. 44 illustrates a front perspective view of a respiration sensor coupled to a patient and a hub adjacent to the patient according to some embodiments.

FIG. 44 illustrates a sensor 2, such as respiration sensor 110a, 100b, coupled to a patient's 20 head, and a hub 4 positioned adjacent to the patient. The hub 4 provides a user interface to the clinician for bedside monitoring. The hub 4 can also provide connectivity and communication between the patient 20 and a network 50 of the hospital.

Figure 45:
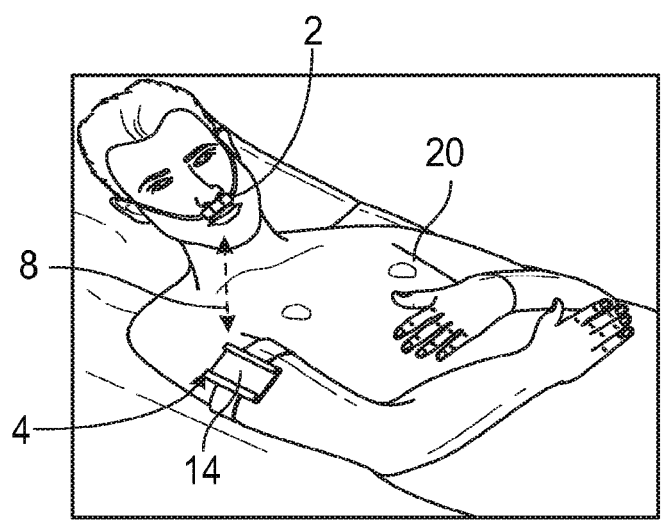
FIG. 45 illustrates a front perspective view of a respiration sensor and hub coupled to a patient, according to some embodiments.

FIG. 45 illustrates a sensor 2, such as respiration sensor 110a, 100b, coupled to a patient's 20 head, and a hub 4, in the form of a smartphone 14 connected via a band to the patient's 20 arm. The hub 4 provides a user interface to the clinician for bedside monitoring. The hub 4 can also provide connectivity and communication between the patient 20 and a network 50 of the hospital. In some embodiments of the present disclosure, the smartphone 14 can be placed on a holder adjacent to the patient. The holder can couple with the smartphone 14 to provide any of a communication interface of charging of the smartphone 14.

The smartphone 14 may include a camera, which can be used for pairing with the sensor 2; Bluetooth to communicate with a low power consumption sensor 2; Wi-Fi to communicate with cloud & hospital network; a user interface enabled for a patient and/or a caregiver; 4G, WCDMA, and GPS. In some embodiments, the smartphone 14 communication is disabled for in-hospital use, and enabled for out-of-hospital use. For example, in out-of-hospital use, when patient and user authentication may be less readily available, the smartphone 14 may perform a face recognition algorithm or other personal/visual/audible recognition algorithms to pair the patient 20 and the respiration sensor 2, and authenticate that the pairing is correct and accurate. When any information is not authenticated, smartphone 14 may issue an alert, sound an alarm, or communicate a warning to a nurse in the centralized system. In some embodiments, the smartphone 14 is configured to integrate with hospital system to provide authentication of patient and/or user during in-hospital use.

Figure 46:
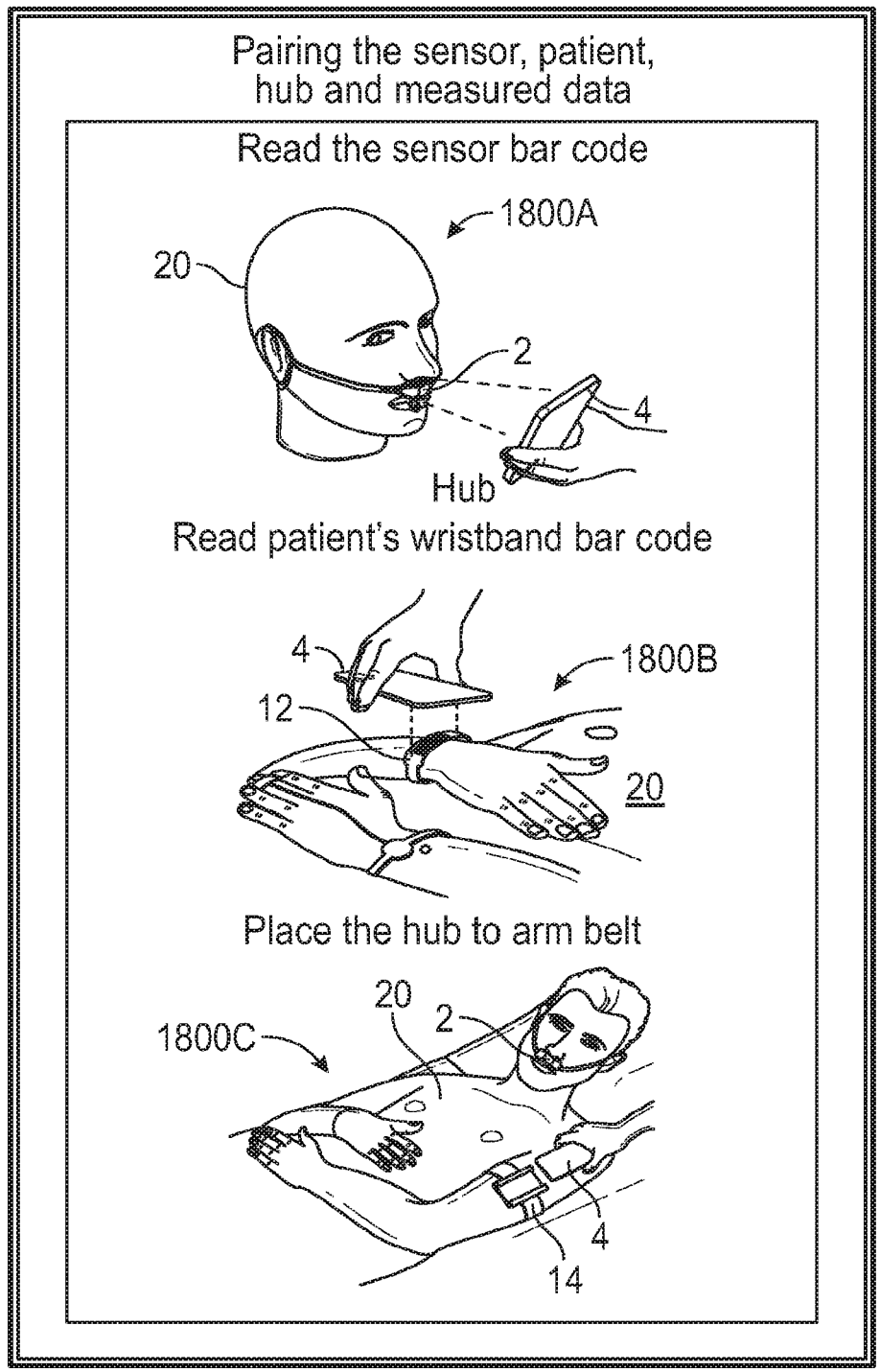
FIG. 46 illustrates perspective detail views of an interaction between a respiration sensor and a hub in a respiration monitoring system, according to some embodiments.

FIG. 46 illustrates an interaction between, for example, the sensor 2 and the smartphone 14 in a respiration monitoring system, according to some embodiments. As will be described further with reference to FIGS. 51-55, the interaction can be used to pair the sensor 2 and the hub 4, and can be used to identify the patient with the sensor 2.

In a first step 1800A, a nurse or authorized healthcare personnel may read data from the sensor 2 in a proximity mode (e.g., a sensor identification value, such as a barcode and the like). In a second step 1800B, the healthcare personnel may further read the patient's wristband 12 to log in the respiratory data in the appropriate patient record. In a third step 1800C, the healthcare personnel may securely place the smartphone 4 in an arm belt 14 on the patient 20. After connection of the hub 4 with a network 50 or a centralized server, for example, the sensor 2 can send and/or receive, in real-time, continuous respiratory data and other information to the network 50 or centralized server.

Figure 47:
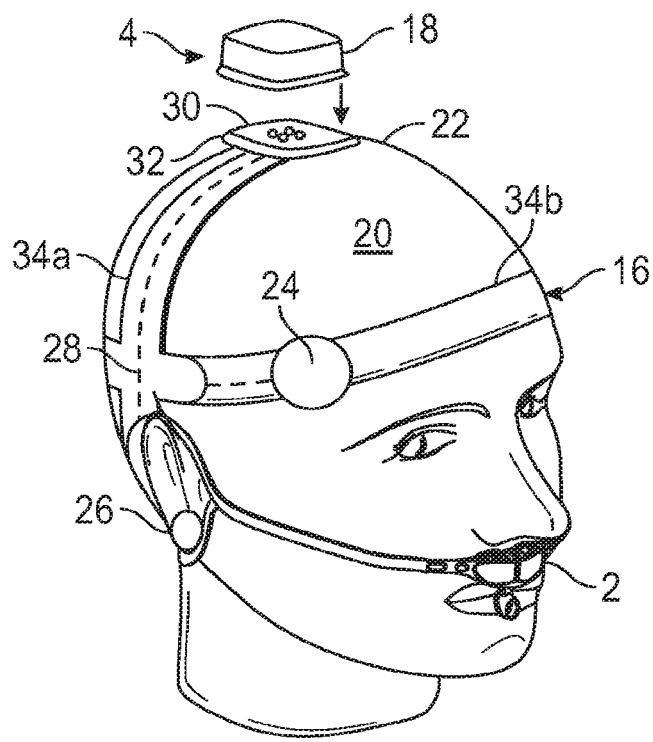
FIG. 47 illustrates a front perspective view of a respiration sensor and hub coupled with a headdress, according to some embodiments.

FIG. 47 illustrates a sensor 2, such as respiration sensor 100a, 100b, and a headdress 16 coupled to the head of a patient 20. The headdress 16 provides an easy to wear, wireless monitoring structure for a mobile patient. The headdress includes a hub 4, in the form of a pod 18 that can be coupled to the headdress 16 at a position adjacent the top of the patient's head.

The headdress 16 can contain sensors attached to, integrated into or in connection with headdress fabric. A sensor 2 (e.g., respiration sensor 100a, 100b) can measure respiration rate and flow. The pod 18 can include a pod sensor 22 to measure any of skin temperature, ambient temperature, or position, motion and acceleration of the patient.

A head sensor 24 can be configured to engage against the patient's head when the headdress is worn by the patient. In some embodiments, the head sensor 24 is positioned adjacent to the temple of the patient's head when the headdress is worn by the patient. In some embodiments, the head sensor 24 can extend across the patient's forehead. The head sensor can measure any of temperature, frontal EEG, frontal oxygen saturation, or movement of the patient. In some examples, the head sensor 24 includes electrodes positioned at different positions on the patient's head to measure full EEG.

An ear sensor 26 can be configured to engage against an ear lobe of the patient when the headdress is worn by the patient. The ear sensor 26 can measure oxygen saturation. The sensor 2 and headdress sensors 22, 24, 26 can transform physiological signals into electrical signals for measuring physiological parameters. For example, respiration sensor 100*a*, 100*b*, and/or other headdress sensors 22, 24, 26, can measure any of respiration rate (RR), breathing gas flow, nasal-SpO2, ear-SpO2, frontal-SpO2, pulse rate (PR), heart rate (HR), skin temperature, ambient temperature, core temperature, body position or movement, chest or thoracic motion, EtCO2, full-EEG, frontal EEG, or similar parameters. The sensors are located at suitable locations around the headdress, depending on the measured physical parameter, to enable optimized measurement of that parameter.

Each sensor may contain a battery to electrically power up the sensor and each sensor may also contain a transceiver to communicate with a host (e.g., network 50) or monitor further away. Preferably sensors are electrically powered through wires 28 integrated into headdress 16, which connect the sensors with a battery located into one location on the headdress 16. The sensors also communicate with the host through one transceiver located in the pod 18. The data communication between the sensors and the transceiver can be via the wires 28 integrated into headdress. This simplifies the electronics and power management infrastructure, decreases radio frequency pollution, which improves communication quality, lowers the cost, weight and size, decreases the power consumption and improves usability and patient comfort.

The sensors attached to headdress 16 only contain a minimum amount of mechanics and electronics to simplify and minimize the sensors infrastructure. For example, to enable the measurement of a physiological signal, only the parameter specific electronics to enable to transform the physiological signal of that specific parameter into an electrical signal are located into each sensor. All the electronics that have commonalities between the sensors can be combined in the pod 18, which can also include the battery, processing unit, transceiver and similar. This centralizing reduces complexity, makes size and weight smaller, increase patient comfort and usability and also reduces the cost of the sensors.

Sensors located on fixed or certain places on the headdress 16 also increase the usability and the quality of measurement as sensors locate and place optimally on patient's head regardless of patient's appearance or differences between users. Simpler, easy to dress wearable system also increases the adoption of a complex multi-parameter system.

The pod 18 can be removed for reuse, and the headdress 16 and sensors therein disposed. Disposability reduces cross contamination risk and decreases care personnel's working time needed for otherwise disinfecting products.

The pod 18 can include most of the electronics, radio transceiver, electrical power source such as a battery, processor etc. and software. The system hardware and mechanics are simplified by centralizing complex functions into a reusable pod, which also makes the system more efficient, easy to clean to prevent cross contamination between patients and low cost. Further, the top of the head is also one of the most comfortable places for the pod 18 when patient is lying, sitting or moving, but it also ensures easy device access and alarm visibility to care personnel.

Electrical signals from any of the headdress sensors 22, 24, 26 and respiration sensor 2 can be transmitted from through the electrical wires 28 to the pod 18 where they are processed into suitable form to be transmitted wirelessly to the monitor. In some embodiments, the pod 18 can communicate with any of the sensors 2, 22, 24, 26, headdress 16, and the monitor via Low energy Bluetooth or similar communication method. Preferably the communication with the monitor is via WiFi, 3G, 4G communication or similar. This ensures that data from a mobile patient can be transferred to a monitor device and hospital from any place inside or outside hospital.

To ensure data is not lost during communication interruption the pod 18 can contain internal First in first out (FiFo) memory to record data for a time of interruption. The monitor shows the processed data in a suitable form, for example on the host's display in digits and waveforms and alarms the care personnel when needed.

The pod 18 can have electrical contacts on a surface, which are configured to engage against reciprocal electrical contacts 30 on a surface of a pod frame 32 coupled to the headdress 16. In some embodiments, the electrical contacts 30 in connection with the headdress 16 are planar. When pod 18 is attached to pod frame 32 these electrical contacts 30 connect electrical power and electrical data lines to enable power and data transfer between the sensors 2, 22, 24, 26 and the pod 18 through the electrical wires integrated into to headdress 16. The attachment between the pod 18 and pod frame 32 may be mechanical sliding or pressing into rails or it may be magnetic or similar.

A battery inside the pod 18 can be rechargeable. When charging is needed, the pod 18 can be separated from the pod frame 32 and coupled to a source of electricity. In some embodiments, the pod 18 can be placed on a wireless charging table or a docking station based on for example inductive charging.

The outer surfaces of pod 18 can be smooth to prevent injury, prevent catching on fabric, and permit easy cleaning and disinfecting. Power on/off and similar functions are implemented with for example capacitive buttons rather than mechanical buttons so that the user only touches the marked areas on the surfaces of pod 18. The pod 18 can have any of an alarm light and an audible alarm. The alarm light or audible alarm can be integrated inside the pod 18. The alarm light can become visible through a partially transparent housing made of material such as plastic.

The headdress can include straps 34*a*, 34*b* that extend around at least a portion of the patient's 20 head, as illustrated in FIG. 47. The headdress 16 can be configured so that, when the headdress 16 is worn by a patient 20, a first strap 34*a* can extend over the top of the patient's head, and a second strap 34*b* can extend across the forehead of the patient. The headdress 16 can include a fastener to permit attachment of the straps 34*a*, 34*b* to each other and to adjust the headdress 16 to conform to a particular patient's head. The fastener can include any of a hook and loop fastener, button, snap, or adhesive. In some embodiments, the at least a portion of the straps 34*a*, 34*b* or headdress 16 is formed of an elastic material.

Figure 48:
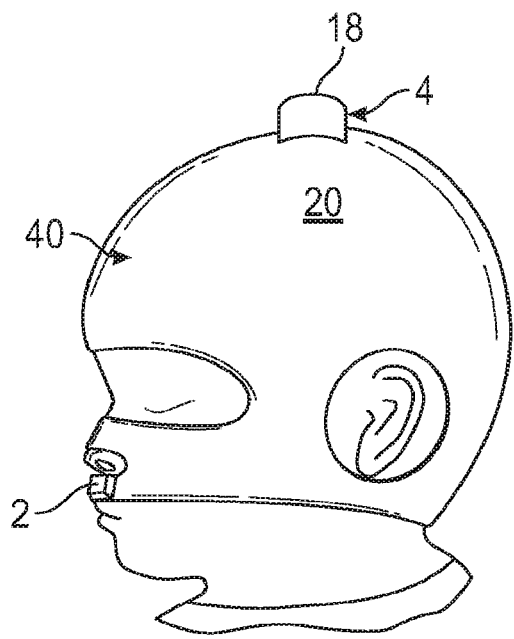
FIG. 48 illustrates a side view of a respiration sensor and hub coupled with another headdress, according to some embodiments.

FIG. 48 illustrates an embodiment of a headdress 40, which extends along a greater portion of the patient's 20 head relative to the headdress 16 illustrated in FIG. 47. When worn by a patient 20, the headdress 40 can extend along any of the patient's head top, forehead, crown, and nape, as well as the upper lip. The additional area covered by the headdress 40 distributes pressure against the patient 20 over a greater area, thereby reducing discomfort. Further, the additional area covered by the headdress 40 can resist movement of the headdress 40 relative to the patient's head. The headdress 40 can be used for adults and/or children as well as infants.

Figures 49, 50:
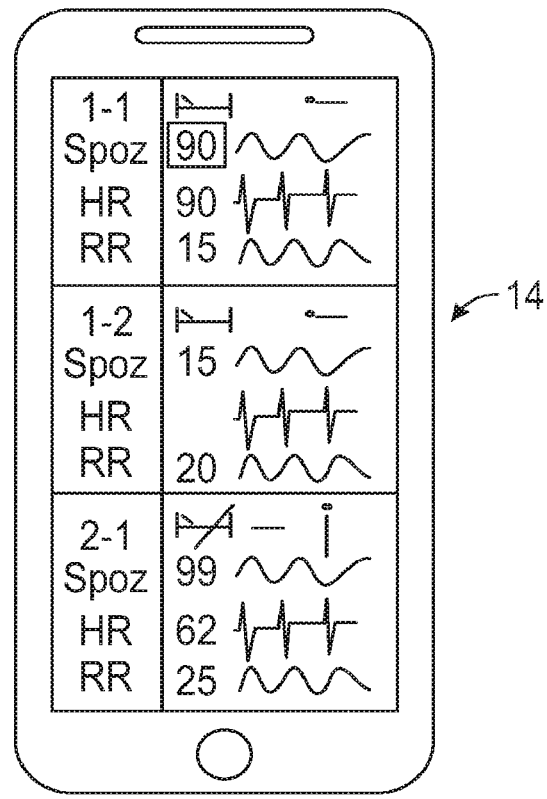
FIG. 49 illustrates a front perspective view of a smartphone as a monitor for a respiration monitoring system, according to some embodiments.
FIG. 50 illustrates a front perspective view of a central station as another monitor for a respiration monitoring system, according to some embodiments.

Referring to FIGS. 49 and 50, examples of monitors are illustrated. The monitor can be any device or system where data is received from a hub 4 or respiration sensor 2. FIG. 49 illustrates a monitor in the form of a smartphone 14. The smartphone 14 can be a patient's phone, a caregiver's phone, or the phone of another person monitoring the patient. FIG. 50 illustrates a monitor in the form of a central station 42. The central station 42 can be a television, computer station, display board, or another display that can be observed by a person monitoring the patient.

The monitor can graphically display information regarding the patient and/or data received from any of the sensor 2 and hub 4. The displayed information can include a temperature value from at least one of two nasal flow passages, a temperature value from an oral flow passage, a temperature value of a patient's skin surface, and a temperature value of a patient's environment. In some embodiments, the displayed information includes an identification of the patient and/or their location (e.g., 1-1, 1-2, 2-1), SpO2 measurement, heart rate, and respiration rate. Additionally, displayed information can include an indication of a patient's orientation or position. The patient's orientation or position can be shown in text or as a symbol. For example, the text or symbol may represent whether the patient is lying on the bed, is standing upright, is sitting up, or is in some other position.

IX. Pairing Process

As described above, the sensor device 2 may include one or more of the sensors described herein (including, for example, sensor 100*a* and/or sensor 100*b*), and at least a portion of sensor 2 may be positioned on a patient, such as on an upper lip of the patient. The sensor 2 may include or work in connection with one or more processors, such as a CPU unit 1416, and together may be configured to initiate a pairing process with a monitoring device, such as the hub 4, based on physiological parameters of the patient. Additional details of the pairing process is described herein with reference to FIG. 51.

Figure 51:
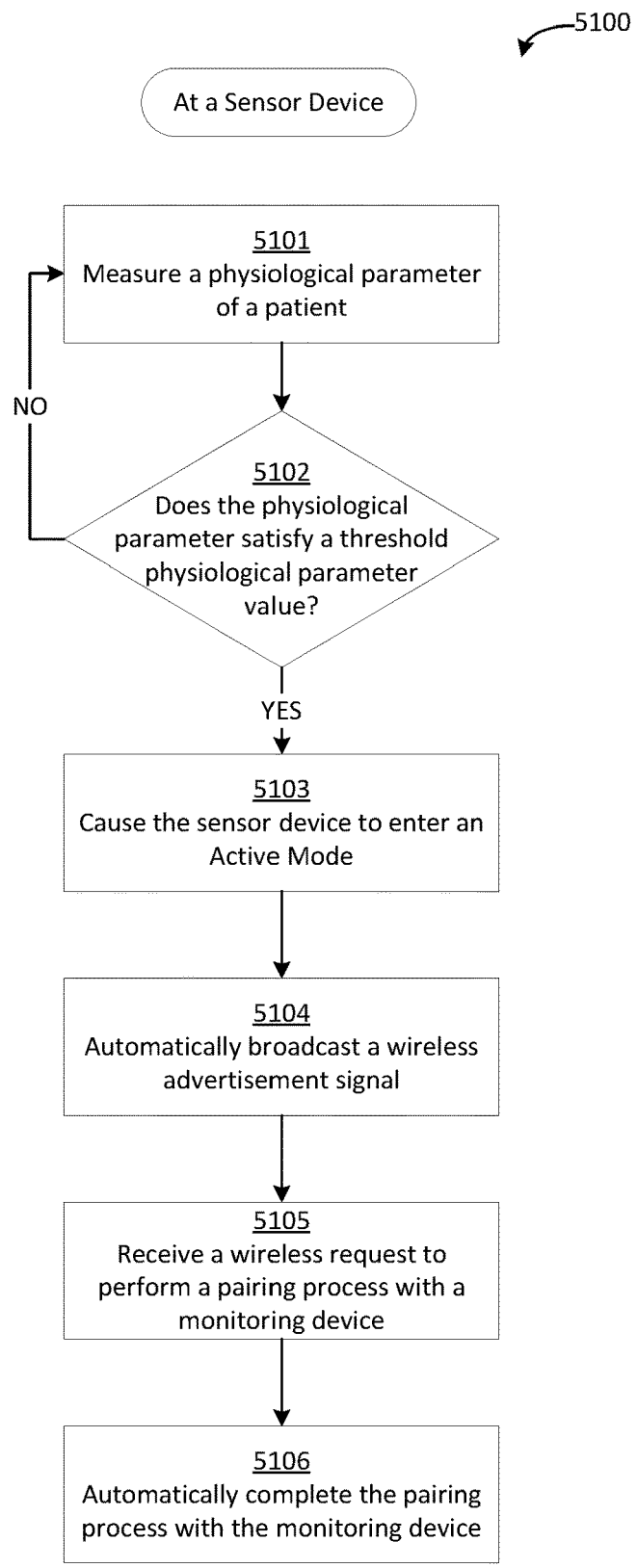
FIG. 51 is a flow chart of an example method of a sensor device detecting a physiological parameter and initiating a pairing process with a monitoring device, according to illustrative implementations.

Turning now to FIG. 51, there is shown a flowchart illustrating a pairing process of a sensor device and a monitoring device. For the purpose of illustrating a clear example, components of the monitoring system 1, and components of the respiration sensors 100*a*, 100*b*, previously described herein, may be used to describe the pairing process of a sensor device and a monitoring device.

The method 5100 includes, by a sensor device, (such as the sensor device 2), measuring a physiological parameter of a patient (block 5101). The sensor 2 may initially be in a deep sleep mode or a low-power mode prior to measuring the physiological parameter of the patient; and, in some implementations, the sensor 2 may be in the deep sleep mode or the low-power mode while measuring the physiological parameter of the patient. In a deep-sleep or low-power mode, the sensor 2 may be configured to operate using fewer associated processors (e.g., use only one of processors) than when the sensor 2 operates in a normal power mode or a high power mode. For example, in the deep-sleep or low-power mode, the sensor 2 may be configured to use only one of the associated processors, and when the sensor 2 is in a normal mode or a high power mode, the sensor 2 may be configured to use all of the associated processors. In the deep-sleep or low-power mode, the sensor 2 may be configured to only perform certain predetermined functions, such as measuring a physiological parameter of the patient and/or detecting whether the sensor 2 or portion thereof is in contact with a portion of the patient's body, such as the upper lip. By operating using fewer associated processors and/or performing only predetermined critical functions, the sensor 2 decreases power consumption and increases its battery life.

The sensor 2 may remain in the deep sleep mode or low-power mode until a threshold condition related to the physiological parameter is satisfied. For example, the sensor 2 may be configured to measure the breath of the patient (e.g., by use of any sensor and/or method described above) and convert the breath to a digital signal and/or a numerical value. The one or more processors associated with the sensor 2 may be configured to store this physiological parameter data in a storage unit of the sensor 2 or communicatively coupled to the sensor device 2. For example, the CPU unit 1416 may be configured to determine a respiration rate value and/or flow rate value based on the measured breath and store the respiration rate and/or the flow rate of the patient in the storage unit. The breath may be measured at one or more nostrils or at the mouth of the patient as described by any of the mechanisms above.

The one or more processors associated with the sensor device 2, may determine if the measured physiological parameter satisfies a threshold physiological parameter value (block 5102). In some implementations, the threshold physiological parameter value may be a certain value of the respiration rate and/or a flow rate. For example, if the physiological parameter is a breath of the patient, then the threshold physiological parameter value may be a certain level and/or a value of a respiration rate or a flow rate. In some implementations, the one or more processors associated with the sensor device 2 may be configured to determine whether the threshold physiological parameter value is satisfied based on whether a consecutive number of measurements of the physiological parameter satisfy a certain value.

In some implementations, the one or more processors associated with the sensor device 2 may be configured to determine if each of the consecutive number of measurements of the physiological parameter is at least a certain value. For example, if the measured physiological parameter is a breath of the patient, then the threshold physiological parameter may be a respiration rate and it may be specified that each of the consecutive number of measurements of the respiration rate be at least a certain level. The one or more processors associated with the sensor device 2 may be configured to track a consecutive number of measurements of the physiological parameter that satisfy a threshold value of the physiological parameter via a counter. The one or more processors associated with the sensor device 2 may be configured to reset the counter if one of the measurements of the physiological parameter does not satisfy the threshold value of the physiological parameter.

If the one or more processors associated with the sensor device 2 determines that the measured physiological parameter value does not satisfy the threshold physiological parameter value (NO' at block 5102), then the method 5100 continues to block 5101. If the one or more processors and/or the sensor device 2 determine that the measured physiological parameter value satisfies the threshold physiological parameter value (YES' at block 5103), then the method continues to block 5103.

The one or more processors associated with the sensor device 2 may be configured to cause the sensor device 2 to enter an active mode (block 5103). In the active mode, at least a majority of the modules of the sensor device 2 are powered-on, and the sensor device 2 may be configured to operate at a higher performance level than when the sensor device 2 is operating in low-power mode or deep sleep mode. The sensor device 2 may operate at a higher power level in the active mode than when the sensor device 2 is in a deep sleep or low-power mode, and the sensor device 2 may be configured to operate using all or most of the processors associated with the sensor device 2 while the sensor device 2 is in active mode. The one or more processors associated with the sensor device 2 may automatically cause the sensor device 2 to enter the active mode in response to the measured physiological parameter value satisfying the threshold physiological parameter value. The one or more processors associated with the sensor device 2 may be configured to automatically broadcast a wireless advertisement signal (block 5104). In response to the sensor device 2 entering the active mode, the one or more processors associated with the sensor device 2 may be configured to automatically broadcast the wireless advertisement signal. In some implementations, the wireless advertisement signal may be a Bluetooth signal.

The one or more processors associated with the sensor device 2 may be configured to receive a wireless request to perform a pairing process between with a monitoring device (block 5105), such as hub 4. The sensor device 2 may receive the wireless request from the monitoring device in response to automatic broadcast of the wireless advertisement signal. The one or more processors associated with the sensor device 2 may be configured to automatically complete the pairing process with the monitoring device (block 5106). After the pairing process is automatically completed, the one or more processors associated with the sensor device 2 may be configured to communicate with the monitoring device. In some implementations, the one or more processors associated with the sensor device 2 receives a patient identifier of a patient during the pairing process. For example, the monitor device, hub 4, may transmit the patient identifier of the patient to the sensor device 2 after sending the wireless request to perform the pairing process with the hub 4. In some implementations, the one or more processors associated with the sensor device 2 stores the patient identifier of the patient in a storage unit associated with and/or operably coupled to the sensor device 2. In some implementations, prior to the initiation of the pairing process, the monitoring device, such as hub 4, may be configured to capture the patient identifier of the patient. Additional details of the monitoring device capturing the patient identifier are described below with reference to FIGS. 54 and 55.

In some implementations, the one or more processors associated with the sensor device 2 may be configured to determine and associate a color with the sensor device 2. The sensor device 2 may be configured to determine the color after the sensor device 2 enters the active mode, and display the color via an electronic component of the sensor device 2 that is configured to emit or display color or colored light. Examples of such electronic components include, but are not limited to, light emitting diodes (LED), and the like. In some implementations, the LED may be a multicolor LED connected to a circuit that selects one of multiple predetermined colors to be illuminated by the LED (e.g., by providing a predetermined voltage to a pin of the LED corresponding to a particular color). Additional details of the sensor device 2 determining the color is described herein with reference to FIG. 52.

In some implementations, the sensor device 2 may continue to remain in deep sleep mode until it detects skin and/or tissue of a patient. In some implementations, one or more processors of the sensor device 2 are activated when skin and/or tissue of the patient is detected. In some implementations, the sensor device 2 may be configured to determine temperature of skin of the patient, temperature of breathe, and the like, when skin and/or tissue of the patient is detected. In some implementations, when skin and/or tissue of the patient is detected, the sensor device 2 may determine if the temperature of the skin is near 37 degrees Celsius, and in response, initiates detection of the threshold number of breaths from the patient.

Figure 52:
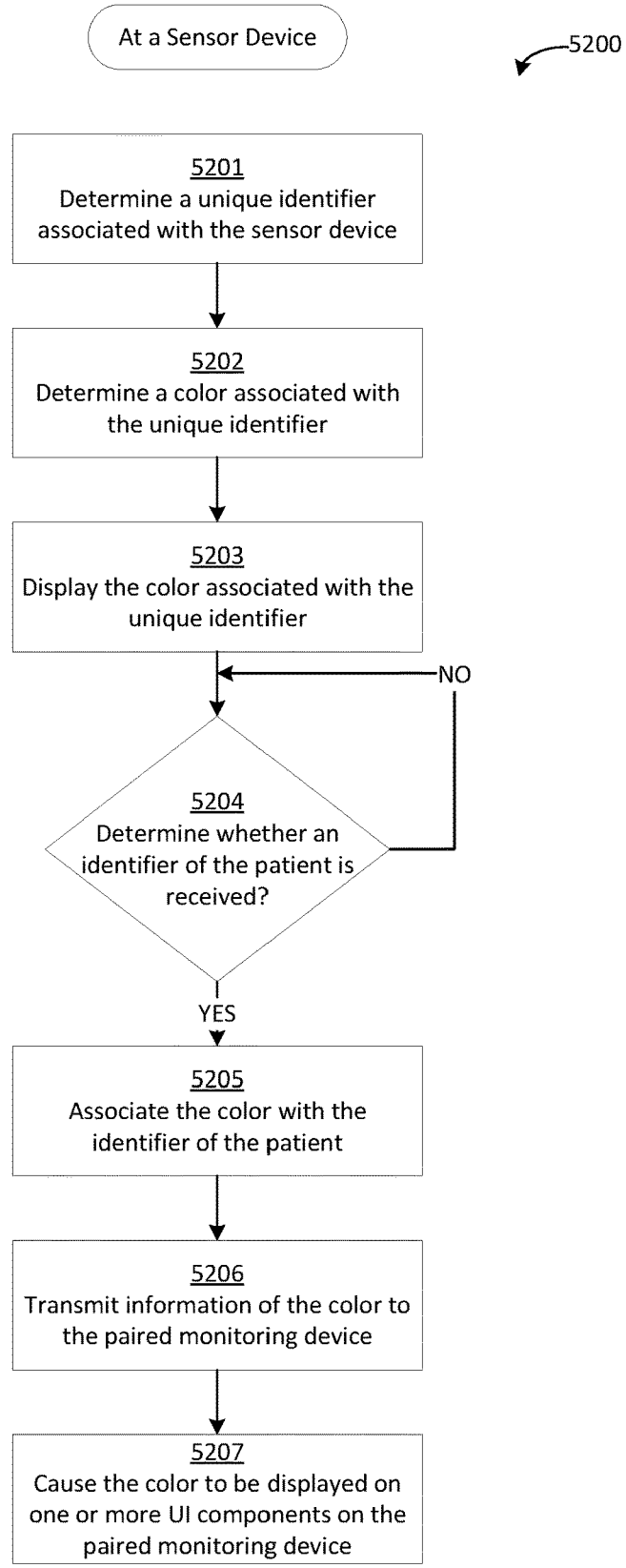
FIG. 52 is a flow chart of an example method of a sensor device determining a color for the sensor device, according to illustrative implementations.

Turning now to FIG. 52, there is shown a process to determine a color associated with a sensor device, such as the sensor device 2. The method 5200 includes, at a sensor device, such as the sensor device 2, determining a unique identifier associated with the sensor device by the one or more processors associated with the sensor device (block 5201). Each sensor device may be associated with a unique identifier and the unique identifier may be stored in a storage unit of the sensor device 2. The one or more processors associated with the sensor device 2, such as the CPU unit 1416, may be configured to determine the unique identifier by retrieving the unique identifier stored in the storage unit of the sensor device 2.

In some implementations, the color associated with the unique identifier may be determined based on a character of the unique identifier. In some implementations, the color associated with the unique identifier may be determined based on one or more characters present at one or more positions of the unique identifier. For example, the color may be determined based on a character present in the last position of the unique identifier. Similarly, the color may be determined based on characters present in the second and third positions of the unique identifier. The one or more processors and/or sensor device 2 may be configured with a set of rules that specify different colors for different characters that may be present in the desired positions of the unique identifier. For example, the set of rules may specify that if the character in the last position of the unique identifier is an "A," then the color is green. Similarly, the set of rules may specify that if the characters in the second and third positions of the unique identifier is a "1" and a "b" then the color is blue.

In some implementations, the set of rules may specify a color for each possible character that may be present in the desired positions of the unique identifier. The one or more processors associated with the sensor device 2 may be configured to determine or retrieve the unique identifier of the sensor device 2, determine the character present in the desired position (e.g., last position) of the unique identifier, and based on the set of rules and the character in the desired position, determine a color. For example, if the unique identifier of a sensor device is "4cx1oD" and the desired positions for determining a color is the last position, then the one or more processors associated with the sensor device 2, using the set of rules, may determine a color mapped to and/or associated with the character "D." In some implementations, the one or more processors associated with the sensor device 2 may be configured to associate the determined color with the sensor device 2 and store the association in a storage unit of the sensor device 2 and/or a storage unit operably and communicatively coupled to the sensor device 2.

The sensor device 2 may be configured to physically display the color associated with the unique identifier by illumination of the LED (block 5203). The one or more processors associated with the sensor device 2 may be configured to cause the color associated with the unique identifier to be displayed on or via an electronic component of the sensor device 2 (not shown). The electronic component may be a multicolored LED configured to emit or display color or colored light In some implementations, the multicolor LED may comprise a microcontroller and multiple light emitting diodes that are configured to emit colored lights, such as red, green, blue lights. The one or more processors associated with the sensor device 2 may be configured to cause a certain color to be displayed via the multicolor LED based on a combination of the different colored lights of the multicolor LED.

The one or more processors associated with the sensor device 2 may be configured to determine whether an identifier of the patient is received from a monitoring device (block 5204). As described above, the monitoring device, such as the hub 4, may be configured to transmit an identifier of the patient together or concurrently with, or after, sending the wireless request to perform the pairing process. If the one or more processors associated with the sensor device 2 determines that the identifier of the patient is not received (NO' at block 5204), then the method proceeds back to block 5204. In some implementations, the one or more processors associated with the sensor device 2 may be configured to wait a predetermined amount of time prior to proceeding back to the block 5204. For example, the one or more processors associated with the sensor device 2 may be configured to wait 10 seconds prior to proceeding to block 5204.

If the one or more processors associated with the sensor device 2 determines that the identifier of the patient is received (YES' at block 5204), then the method proceeds to block 5205. The one or more processors may be configured to associate the color with the identifier of the patient (block 5205). The one or more processors associated with the sensor device 2 may be configured to store the association of the color with the received identifier of the patient in a storage unit associated with the sensor device 2 and/or a storage unit operably coupled to the sensor device 2. In doing so, the color is associated with the patient. The one or more processors associated with the sensor device 2 may be configured to transmit information of the color to the paired monitoring device (block 5206). In some implementations, the one or more processors associated with the sensor device 2 may transmit a message to the paired monitoring device indicating the color. In some implementations, the one or more processors associated with the sensor device 2 may include the information indicating that the color is associated with the patient.

The one or more processors associated with the sensor device 2 may be configured to cause the color to be displayed on one or more user interface (UI) components on the paired monitoring device (block 5207). Examples of UI components may be graphical user interface (GUI) components displayed on a display device of the monitoring device. Examples of the UI components may include, but are not limited to, one or more GUI icons, boxes, labels, frames, background and the like. In some implementations, a portion of the UI components may be displayed in the color associated with the identifier of the patient. For example, one or more edges of a graphical icon, box, label, frame and/or background may be displayed in the color associated with the identifier of the patient. The one or more processors associated with the sensor device 2 may be configured to transmit a message or a command to the paired monitoring device, such as hub 4, to instruct the hub 4 to display the one or more UI components displayed on a display device of the hub 4 or associated with the hub 4 in a color associated with the patient.

In some scenarios, the wireless connection between the sensor device and the paired monitoring device may be lost. For example, the monitor device may be lose power, may be damaged, and/or experience other technical issues that may cause the wireless connection to the sensor device to be dropped or lost. The sensor device 2 may be configured to detect the loss of the wireless connection with the monitoring device, and the sensor device 2, in response to pairing with a new monitoring device, the sensor device 2 may be configured to associate the new monitoring device with the patient via the association of patient and the sensor device 2. Additional details of a sensor device, such as sensor device 2, associating a new monitoring device with a patient associated with a previously paired monitoring device is described with reference to FIG. 53.

Figure 53:
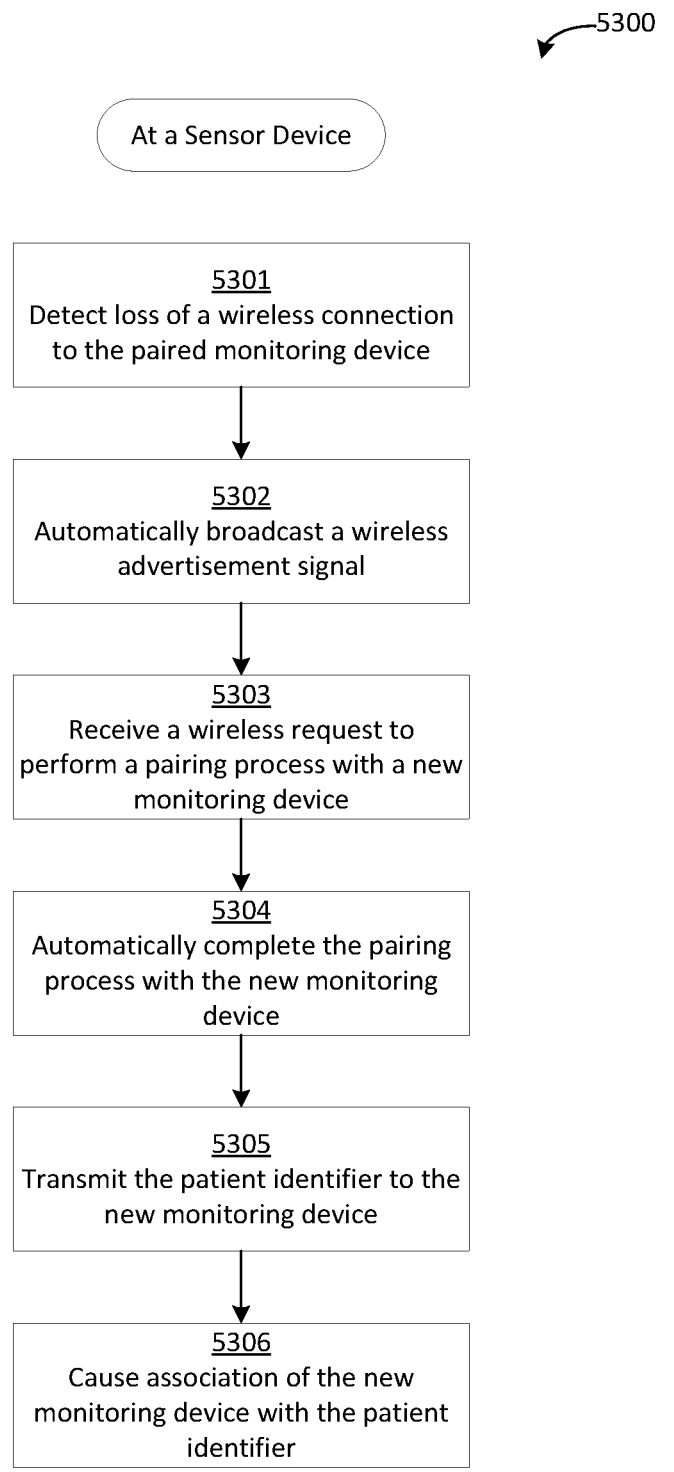
FIG. 53 is a flow chart of an example method of a sensor device associating a new monitoring device with a patient, according to illustrative implementations.

Turning now to FIG. 53, there is shown a process to associate the new monitoring device with the patient. The method 5300 includes, by a sensor device, such as the sensor device 2, detecting loss of a wireless connection to the paired monitoring device, such as hub 4 (block 5301). The one or more processors associated with the sensor device 2, via the communication module of the sensor device 2, may be configured to determine whether a wireless connection with a paired device, such as the hub 4, is still connected. The one or more processors associated with the sensor device 2 may be configured to automatically broadcast a wireless advertisement signal (block 5302). The one or more processors associated with the sensor device 2 may be configured to automatically broadcast a wireless advertisement signal in response detecting loss of a wireless connection to the previously paired monitoring device, such as the hub 4.

The one or more processors associated with the sensor device 2 may be configured to receive a wireless request to perform a pairing process with a new monitoring device (block 5303). In some implementations, the new monitoring device has not been previously associated with the patient that is associated with the sensor device, the sensor device 2. The one or more processors associated with the sensor device 2 may be configured to automatically complete the pairing process with the new monitoring device (block 5304). The one or more processors associated with the sensor device 2 may be configured to automatically complete the pairing process with the new monitoring device in response to the receiving the wireless request to perform the pairing process with the new monitoring device.

The one or more processors associated with the sensor device 2 may be configured to transmit the patient identifier to the new monitoring device (block 5305). As described above, the one or more processors associated with the sensor device 2 may store the received patient identifier from the previously paired monitoring device in a storage unit of the sensor device 2 or a storage unit operably coupled to the sensor device 2. The one or more processors associated with the sensor device 2 may be configured to retrieve the patient identifier from the storage unit and transmit the patient identifier to the new monitoring device. In some implementations, the one or more processors associated with the sensor device 2 may be configured to determine a most recently associated patient identifier with the sensor device 2 and transmit that identifier to the new monitoring device. The one or more processors associated with the sensor device 2 may be configured to cause association of the new monitoring device with the patient identifier (block 5306). In some implementations, the one or more processors associated with the sensor device 2 may be configured to transmit a message or command to instruct the monitoring device to associate the patient identifier transmitted to the new monitoring device with the new monitoring device. In some implementations, the monitoring device may be placed in a charging station, and connection with the charging station can be detected by the monitoring device (e.g., from a charging current received from the charging station, and/or an accelerometer in the monitoring device. In some implementations, the monitoring device may generate alarms if not placed within a threshold amount of time. In some implementations, the monitoring device may display a discharge button on a GUI and selection of the button sends a message to paired sensor device 2 to turn itself off.

Figure 54:
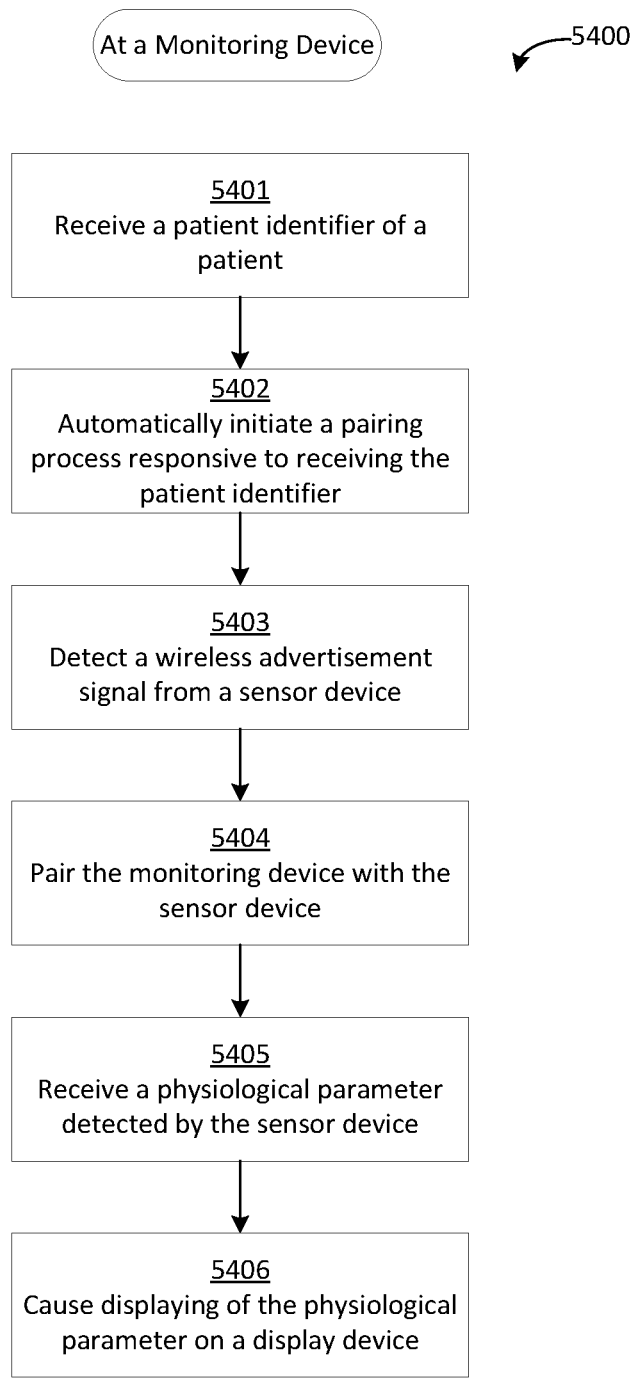
FIG. 54 is a flow chart of an example method of a pairing process with a sensor device at a monitoring device, according to illustrative implementations.

Turning now to FIG. 54, there is shown a pairing process with a sensor device at a monitoring device. The method 5400, at a monitoring device, includes receiving a patient identifier of a patient (block 5401). As described above, in some implementations, a patient identifier of the patient may be received by the monitoring device by scanning the patient identifier. For example, the monitoring device, such as the hub 4, may be configured with a scanning apparatus, such as a one-dimensional (1-D) scanner, two-dimensional (2-D) scanners, and the like. The monitoring device, hub 4, may be configured with an image capturing apparatus and may be configured to receive a patient identifier of the patient via an image of the patient identifier captured by the image capturing apparatus of the monitoring device. The one or more processors of the monitoring device, such as the hub 4, may be configured to determine a patient identifier based on the image of the patient identifier. In some implementations, the one or more processors of the monitoring device may be configured to decode data encoded in barcodes, such as linear barcodes, matrix barcodes, and the like. In some implementations, the patient identifier may be encoded in barcodes, and the one or more processors of the monitoring device may determine the patient identifier based on an image of the barcode captured by the monitoring device. An example of a monitoring device, such as hub 4, receiving a patient identifier is shown in FIG. 46.

The one or more processors of the monitoring device may be configured to automatically initiate a pairing process responsive to receiving the patient identifier (block 5402). As part of the pairing process, the one or more processors of the monitoring device may initiate searching of devices configured to communicate via wireless communication. For example, the one or more processors of the monitoring device may be configured to search for devices configured to communicate via Bluetooth technology. In some implementations, the monitoring device, such as the hub 4, may be configured to operate in a low-power mode until the monitoring device receives a patient identifier of a patient. In some implementations, the monitoring device may be configured to enter into an active mode after receiving or determining the patient identifier.

The one or more processors of the monitoring device may be configured to detect wireless advertisement signal from a sensor device (block 5403), such as the sensor device 2. In some implementations, the wireless advertisement signal may indicate that the sensor device has received a physiological parameter from the patient. The wireless advertisement signal may indicate that the sensor device has received a threshold physiological parameter data. The wireless advertisement signal may indicate that the sensor device is ready to be paired to the monitoring device. The one or more processors of the monitoring device may be configured to pair the monitoring device with the sensor device (block 5404). The one or more processors of the monitoring device may be configured to pair the monitoring device with the sensor device in response to detecting the wireless advertisement signal from the sensor device.

The one or more processors of the monitoring device may be configured to receive a physiological parameter detected by the sensor device (block 5405). As described above, examples of physiological parameter may include, but are not limited to, respiration rate, flow rate, and the like. The one or more processors of the monitoring device may be configured to cause displaying of the physiological parameter on a display device (block 5406). The one or more processors of the monitoring device may be configured to display the received data of the physiological parameter in a GUI displayed on a display device associated with the monitoring device. In some implementations, the one or more processors of the monitoring device may be configured to generate one or more visual representations of the data of the received physiological parameter. Examples of the visual representations of the data may include, but is not limited to, trendlines, and the like.

Figure 55:
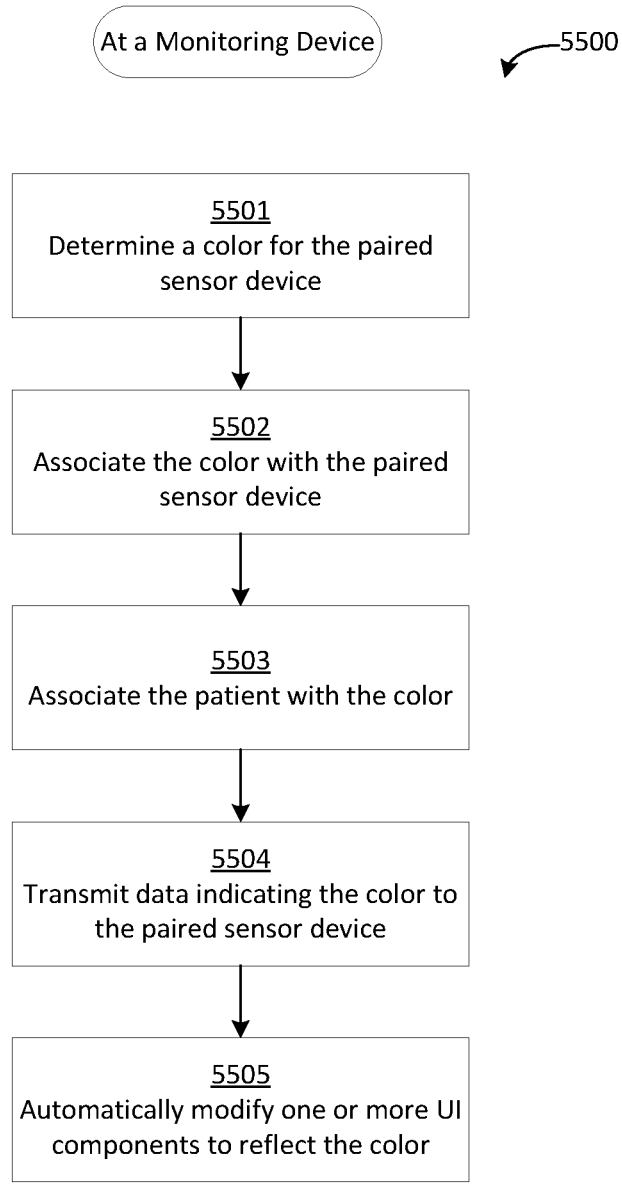
FIG. 55 is a flow chart of an example method of a monitoring device determining a color for a patient, according to illustrative implementations.

In some implementations, the monitoring device may be configured to determine a color for one or more sensor devices paired with the monitoring device and modify one or more UI components displayed on the monitoring device based on the determined color. Additional details of the monitoring device determining a color are described herein with reference to FIG. 55. Turning now to FIG. 55, there is shown a process of determining a color for the paired sensor device by the monitoring device. The method 5500, at a monitoring device, includes determining a color for the paired sensor device (block 5501). In some implementations, the one or more processors of the monitoring device may be configured to determine a list of colors that are in use or associated with other sensor devices, and determines a color that is available for the paired sensor device based on the list of colors. In some implementations, the monitoring device may be configured with an exception list of colors that cannot be associated with any sensor devices. For example, the colors on the exception list of colors may be colors that are used for emergency scenarios in medical facility. The one or more processors may be configured to determine a color for the paired sensor device based on the exception list of colors and the determined list of colors that are in use.

The one or more processors of the monitoring device may be configured to associate the color with the paired sensor device (block 5502). The one or more processors of the monitoring device may be configured to store the association of the color with the paired sensor device in a storage unit of the monitoring device or a storage unit operably coupled to the monitoring device. The one or more processors of the monitoring device may be configured to associate the color with the patient (block 5503). In some implementations, the one or more processors of the monitoring device may be configured to store the association of the color with the patient in a storage unit of a centrally located server. In some implementations, the one or more processors of the monitoring device may be configured to store the association of the color with the patient in a storage unit of the monitoring device.

The one or more processors of the monitoring device may be configured to transmit data indicating the color to the paired sensor device (block 5504). In some implementations, the one or more processors of the monitoring device may be configured to transmit an instruction to the sensor device specifying that the sensor device display the transmitted color via an electronic component of the sensor device, such as an LED. The one or more processors of the monitoring device may be configured to automatically modify one or more UI components to reflect the color (block 5505). As described above, examples of UI components may be graphical user interface (GUI) components displayed on a display device of the monitoring device. The UI components may include, but are not limited to, one or more GUI icons, boxes, labels, frames, background and the like. In some implementations, the one or more processors of the monitoring device may be configured to modify color of portion of the UI components in the color transmitted to the sensor device. In some implementations, one or more edges of a graphical icon, box, label, frame and/or background may be displayed in the color transmitted to the sensor device.

X. Speech Detection

Detection of a patient's speech during a monitoring session of a patient may assist in identifying whether the patient is awake, lucid, and/or experiencing any pain. Furthermore, detection of a patient's speech while a sensor device comprising breathing sensors is actively measuring respiratory and/or flow rates of a patient may assist in improving accuracy of the measured breathing pattern data and provide a more accurate report to a user, such as a nurse or a doctor. The systems and methods described herein provide for detection of a patient's speech and improvement in the accuracy of the displayed breathing pattern data. Additional details of speech detection and improving accuracy of breathing pattern data are described herein with reference to FIG. 56.

Figure 56:
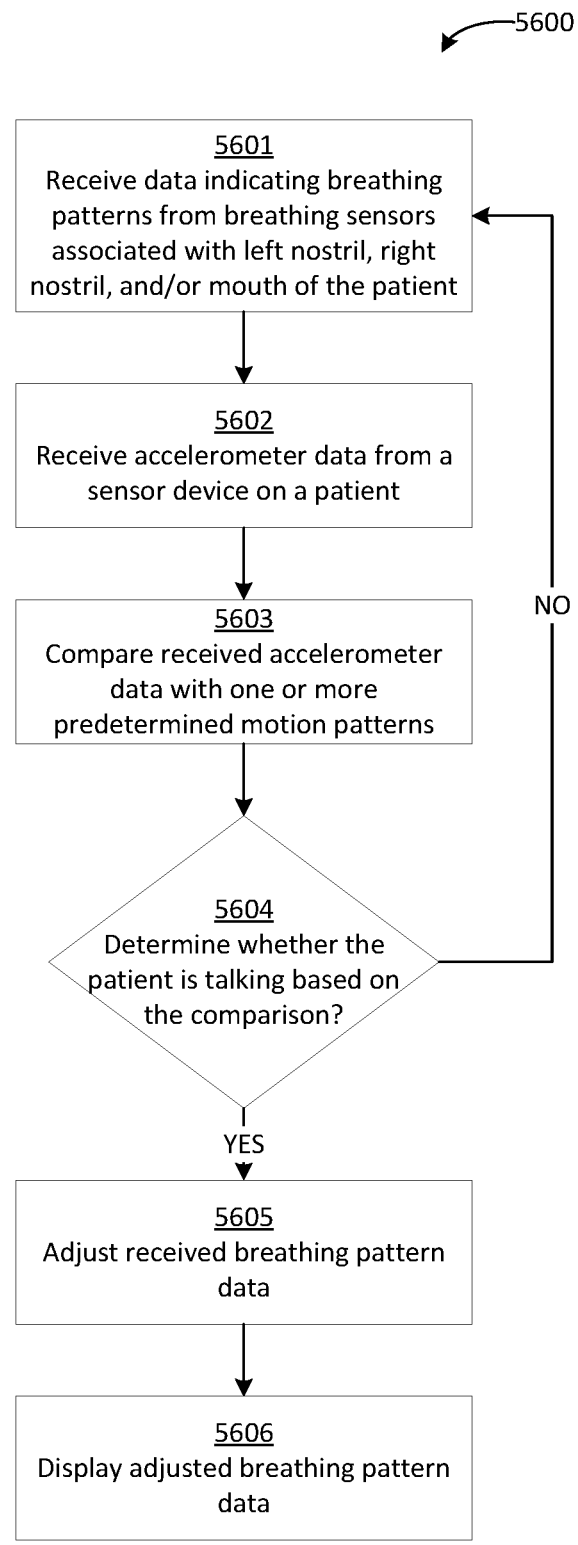
FIG. 56 is a flow chart of an example method of detecting speech by a patient, according to illustrative implementations.

Turning now to FIG. 56, there is shown a flow chart to detect speech of a patient and adjust breathing pattern data. For the purpose of illustrating a clear example, components of the monitoring system 1, and components of the respiration sensors 100a, 100b, previously described herein, may be used to describe the process of determining whether a patient is speaking and adjusting breathing pattern data.

The method 5600 includes receiving, by one or more processors of a monitoring device, data indicating breathing patterns from breathing sensors associated with left nostril, right nostril, and/or mouth of patient (block 5601). As described above, a sensor device, such as sensor device 2, may include one or more breathing sensors, and in some implementations, at least one breathing sensor may be configured to be proximal to a left nostril, a right nostril, and/or a mouth of the patient when the sensor device is placed on the patient. As described above, the sensor device, such as the sensor device 2, may be configured to send the breathing pattern data to the monitoring device The breathing sensor proximal to the left nostril may be associated with the left nostril. Similarly, a breathing sensor proximal to the right nostril may be associated with the right nostril, and a breathing sensor proximal to the mouth may be associated with the mouth. As described herein, the term "data indicating breathing patterns" will be referred to as breathing pattern data.

The breathing pattern data from the breathing sensor associated with the left nostril, right nostril, and mouth may represent respiration rates, and/or a flow rates from the left nostril, the right nostril, and mouth, respectively. In some implementations, this breathing pattern data may include information that specifies that the data may be associated with the left nostril, right nostril, and/or mouth. The one or more processors of the monitoring device may be configured to store the received breathing pattern data of the left nostril, the right nostril, and/or mouth in a storage unit of and/or associated with the monitoring device.

The one or more processors of the monitoring device receive accelerometer data from the sensor device on the patient (block 5602). As described above, the sensor device, such as sensor device 2, may be configured to transmit accelerometer data from one or more accelerometer sensors and/or gyroscope sensors of the sensor device to the paired monitoring device. The accelerometer data may indicate movement of the patient and/or a portion of a patient. For example, the accelerometer data may indicate movement of a lip, such as an upper lip, of the patient. The sensor device may be configured to measure accelerometer data while the breathing pattern data is measured. For example, the accelerometer data may be measured simultaneously with the breathing pattern data. In some implementations, the one or more processors of the monitoring device may be configured to determine a current placement location of the sensor device on a patient based on the received breathing pattern data. For example, the one or more processors may be configured to determine a current placement location of the sensor device on a lip of the patient based on the received breathing pattern data.

The one or more processors of the monitoring device compare the received accelerometer data with one or more predetermined motion patterns (block 5603). The one or more predetermined motion patterns may be motion patterns related to movement of a mouth, a lip (e.g. upper lip), and the like of a human. In some implementations, data related to and/or models associated with the one or more predetermined motion patterns may be stored in a storage unit associated with the monitoring device. As described above, the storage unit associated with the monitoring device may include, but are not limited to, one or more storage units included in the monitoring device, one or more storage units located remotely from the monitoring device and communicatively coupled with the monitoring device, and the like. In some implementations, the one or more processors of the monitoring device may be configured to determine the placement location of the sensor device on the patient. In some implementations, the one or more processors may be configured to initiate comparison of the received accelerometer data (or motion data determined based on accelerometer data) and the predetermined motion data patterns in response to determining the placement location of the sensor device. The one or more processors may be configured to determine whether the determined placement location is within a predetermined distance of a lip of the patient.

The one or more processors of the monitoring device may be configured to determine a motion pattern based on the accelerometer data. As described above, in some implementations, the one or more processors of the monitoring device may be configured to determine a frequency at which the motion pattern occurs. The one or processors of the monitoring device may be configured to determine a similarity level between the determined motion pattern and the one or more predetermined motion patterns based on the comparison. In some implementations, the similarity level may be represented by a value, such as a numerical score, alphanumerical score, a probability value, and the like. In some implementations, the one or more processors may store the determined similarity level in a storage unit associated with the monitoring device.

The one or more processors determine whether the patient is talking based on the comparison (block 5604). The one or more processors may be configured to compare the similarity level with a predetermined threshold similarity level to determine a likelihood that the patient is talking. The predetermined threshold similarity level may indicate a minimum level at which a motion pattern indicated by the accelerometer data and the one or more predetermined motion patterns should match. The predetermined threshold similarity level may be represented in the same format as the determined similarity level. For example, if the similarity level is represented by a numerical value, then the threshold similarity level may also be represented by a numerical value.

Based on the comparison, if the one or processors determine that the similarity level satisfies a predetermined threshold similarity level, then the one or more processors determine a high likelihood that the patient is talking. If the one or more processors determine that the similarity level does not satisfy a predetermined threshold similarity level, then the one or more processors determine a low likelihood that the patient is talking. In some implementations, the one or more processors of the monitoring device may receive audio data from a microphone of the sensor device. The received audio data may be for the same time period during which the accelerometer data was captured. For example, the sensor device may be configured to capture the audio data and the accelerometer data simultaneously. The one or more processors may be configured to determine a decibel level of the received audio data, and compare the decibel level with a threshold decibel level to determine whether the decibel level of the audio data satisfies the threshold decibel level. If the decibel level satisfies a threshold decibel level, then the one or more processors may increase the likelihood that a patient is talking. If the decibel level does not satisfy a threshold decibel level, then the one or more processors may decrease the likelihood that a patient is talking. In some implementations, the one or more processors may first determining whether the decibel level satisfies the threshold decibel level, and if the decibel level satisfies the threshold decibel level, then the one or more processors compare accelerometer data or the determined motion pattern with one or more predetermined motion patterns.

The one or more processors may be configured to compare the generated likelihood value that a patient is talking with a predetermined threshold likelihood value of a patient talking. The one or more processors of the monitoring device may determine that the patient is talking if the generated likelihood value satisfies the predetermined threshold likelihood value of the patient talking. For example, if predetermined threshold likelihood of a patient talking is set at a 90% confidence level, then the one or more processors may determine that the patient is talking if the generated likelihood value also indicates a 90% confidence level that the patient is talking.

If the one or more processors determine that the patient is not talking (NO' at block 5604), then the method 5600 proceeds to block 5601. If the one or more processors determine that the patient is talking (YES' at block 5604), then the method 5600 proceeds to block 5605. The one or more processors adjust the received breathing pattern data (block 5605). Prior to adjusting the breathing pattern data, the one or more processors may be configured to determine whether the received breathing pattern data differs from a baseline breathing pattern data of the patient by a threshold amount. The baseline breathing pattern data of the patient may be determined by the one or more processors of the monitoring device based on breathing pattern data received over multiple previous periods of time. If the one or more processors determine that the received breathing pattern data does not differ from the baseline breathing pattern data by threshold amount, then the one or more processors may not adjust the received breathing pattern data in block 5605, and the method proceeds to block 5606.

If the one or more processors determine that the received breathing pattern data differs from the baseline breathing pattern data by a threshold amount, then the one or more processors adjusts the received breathing pattern data. As described above, the one or more processors of the monitoring device may be configured determine a respiratory and/or flow rate for the left nostril, right nostril, and/or mouth based on the received breathing pattern data. The one or more processors may be configured to adjust the received breathing pattern data by adjusting the respiratory and/or flow rates of the left nostril, right nostril, and/or mouth by a predetermined amount. The predetermined amount may be selected based on one or more machine-learned models that were trained to determine an effect on respiratory and/or flow rates of patients when talking. In some implementations, the one or more processors may be configured to adjust the breathing pattern data by decreasing the determined respiratory and/or flow rates. For example the breathing pattern data may be decreased to reduce the difference between the determined respiratory and/or flow rate data and threshold respiratory and/or flow rate data. In some implementations, if the patient is not talking and the breathing pattern data cannot be measured correctly, then the one or more processors may generate alarm for sleep apnea condition.

The one or more processors display the adjusted breathing pattern data (block 5606). The one or more processors may be configured to display the adjusted breathing pattern data by causing the adjusted breathing pattern data to be displayed on a display device associated with the monitoring device. A display device included with the monitoring device and/or communicatively coupled to the monitoring device may be referred to herein as associated with the monitoring device.

While the above describes one or more processors of the monitoring device performing the process of detecting speech and adjusting breathing pattern data, one skilled in the art should recognize that one or more processors of the sensor device 2 may be configured to perform the process of detecting speech and adjusting breathing pattern data in accordance with the process described in FIG. 56.

XI. Monitoring Device

As described above, a monitoring device, such as a hub 4, may be configured to receive physiological parameter data from a sensor device and display information and/or data related to the received physiological parameter data on a display device of and/or associated with the monitoring device. Based on the received physiological parameter data, the monitoring device 4 may be configured to determine whether the patient is at risk of experiencing certain physiological and/or medical conditions, such as sleep apnea, physical pain, nasal cavity conditions, and the like, generate alerts based on the determined physiological conditions, and/or provide alerts to one or more users, such as a nurse, a doctor, other clinicians, friends, and/or family members of a patient. The monitoring device may be configured to determine a position of the sensor device on a face of a patient based on the physiological parameter data. The position may be a location on the face relative to a facial feature such as the nose, mouth/lips, or neck of the patient. The monitoring device may be configured to determine whether a sensor device is properly positioned on the patient based on the position of the sensor device.

Furthermore, the monitoring device 4 may be configured to receive location and/or movement data of the patient, e.g., from the sensor device 2. The location data may include, but is not limited to, data from one or more wireless transmitter devices configured to transmit their identifiers, such as beacon devices, and the like. The monitoring device may also be configured to receive movement data of the patient, e.g., from the sensor device 2. Examples of movement data of a patient include, but are not limited to, data from one or more accelerometer sensors and/or gyroscope sensors on and/or associated with a patient (e.g., embedded in sensor device 2). The monitoring device 4 may be configured to determine medical conditions based on the movement data of the patient. For example, the monitoring device 4 may identify sleep apnea based on the movement data of the patient. The monitoring device 4 may be configured to modify and/or update user interfaces based on location of the monitoring device 4. Additional details of monitoring a patient are described herein with reference to FIGS. 57-62.

Figure 57:
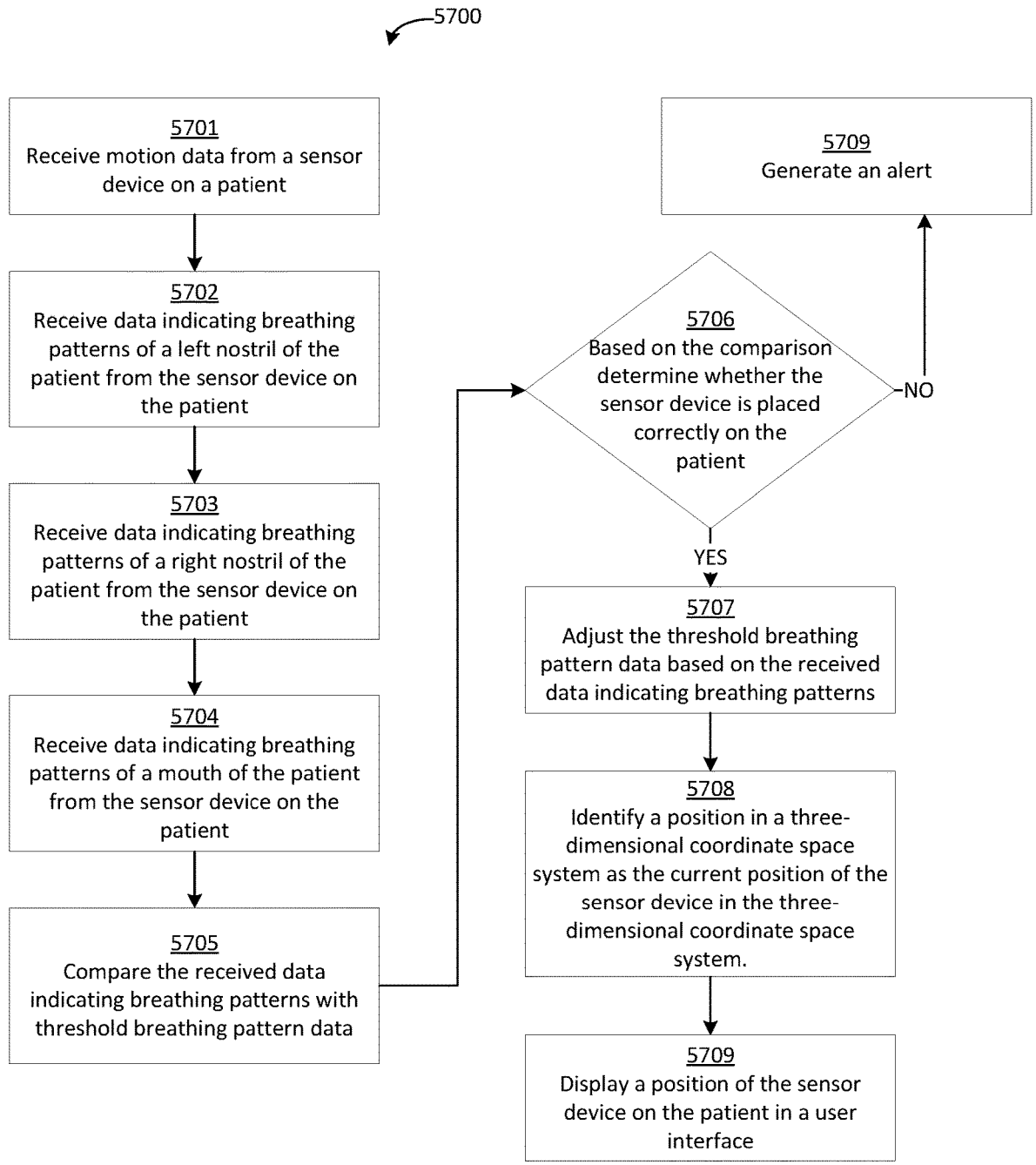
FIG. 57 is a flow chart of an example method of displaying a position of a sensor device on a patient, according to illustrative implementations.

Turning now to FIG. 57, there is shown a process to determine a position of a sensor device on a patient. For the purpose of illustrating an example, components of the monitoring system 1, and components of the respiration sensors 100*a*, 100*b*, previously described herein, may be used to describe the process of determining a position of a sensor device on a patient. In some implementations, a monitoring device 4 may include a memory storage unit. In some implementations, a monitoring device may be communicatively coupled with a remotely located storage unit (e.g., a cloud-based storage unit). One or more processors of the monitoring device may be configured to store data in any storage unit associated with the monitoring device.

The method 5700 includes, by a monitoring device 4 receiving motion data (including, e.g., accelerometer data) from a sensor device on a patient (block 5701). As described above, the sensor device, such as sensor device 2, may be configured to transmit motion data measured by one or more accelerometer sensors and/or gyroscope sensors of the sensor device to the paired monitoring device. The motion data may indicate movement of the patient. For example, the motion data may indicate the patient moving their head. The one or more processors of the monitoring device receive data indicating breathing patterns of a left nostril of the patient from the sensor device on the patient (block 5702). As described above, a sensor device, such as sensor device 2, may include one or more breathing sensors, and in some implementations, at least one breathing sensor may be configured to be positioned proximal to a left nostril of the patient when the sensor device is placed on the patient. The breathing sensor proximal to the left nostril may be programmatically associated with the left nostril (e.g., via coded instructions). As described herein, the term "data indicating breathing patterns" will be referred to herein as breathing pattern data. The breathing pattern data from the breathing sensor associated with the left nostril may represent a respiration rate, and/or a flow rate from the left nostril, and, in some implementations, may include information that specifies that this breathing pattern data is associated with the left nostril (e.g., an identification of the left nostril). The one or more processors of the monitoring device may be configured to store the received breathing pattern data of the left nostril in a memory storage unit associated with the monitoring device.

According to various aspects, one or more processors of the monitoring device receive data indicating breathing patterns of a right nostril of the patient from the sensor device on the patient (block 5703). Similar to the breathing sensor associated with the left nostril, a breathing sensor positioned proximal to the right nostril may be programmatically associated with the right nostril. The breathing pattern data from the breathing sensor associated with the right nostril may represent a respiration rate, and/or a flow rate from the right nostril. In some implementations, this breathing pattern data may include information that specifies that the data is associated with the right nostril (e.g., an identification of the right nostril). The one or more processors of the monitoring device may be configured to store the received breathing pattern data of the right nostril in a storage unit of and/or associated with the monitoring device.

The one or more processors of the monitoring device receive data indicating breathing patterns of a mouth of the patient from the sensor device on the patient (block 5704). Similar to the breathing sensors associated with the left and right nostrils, the breathing pattern data from the breathing sensor associated with the mouth may represent a respiration rate, and/or a flow rate from the mouth, and may include information that specifies that the data is associated with the mouth. The one or more processors of the monitoring device may be configured to store the received breathing pattern data of the mouth in a memory storage unit associated with the monitoring device.

The sensor device may transmit the breathing pattern data of the left nostril, right nostril, and/or the mouth to the monitoring device 4 at periodic intervals. In some implementations, the sensor device may transmit the breathing pattern data in real time or near real time such that the breathing pattern data received by the monitoring device represents the current respiration rate and/or flow rate of the patient in real time or near real time. As data is received, one or more processors of the monitoring device may be configured to timestamp the breathing pattern data, or otherwise associate the received breathing pattern data with an instance of time or a period of time. In some implementations, the associated instance or period of time may represent the time at which the breathing pattern data is captured by the sensor device. In some implementations, the associated instance or period of time may represent the time at which the breathing pattern data is received by the monitoring device. The one or more processors may be configured to store in the memory storage unit the received breathing pattern data along with an indication of time (e.g., a timestamp) that represents and/or specifies the associated instance or period of time.

The one or more processors of the monitoring device compare the received data indicating breathing patterns with threshold breathing pattern data (block 5705). The monitoring device may be configured with a threshold breathing pattern data for each type of breathing pattern data. For example, a threshold breathing pattern data for a left nostril, a threshold breathing pattern data for a right nostril, and/or a threshold breathing pattern data for a mouth may be stored in a storage unit associated with the monitoring device. The one or more processors of the monitoring device may be configured to compare the received breathing pattern data of the left nostril with threshold breathing pattern data for the left nostril. Similarly, the one or more processors may be configured to compare the received breathing pattern data of the right nostril and the mouth with threshold breathing pattern data of the right nostril and the mouth, respectively.

In some implementations, the threshold breathing pattern data may be predetermined and provided as an input to the monitoring device. In some implementations, the monitoring device may determine the threshold breathing pattern data based on a profile of the patient, such as a biographical and/or physiological profile of the patient. For example, the monitoring device may be configured to determine an expected respiratory rate and/or a flow rate (e.g., for the left nostril, right nostril, and/or mouth) based on a patient's age, weight, height, and the like. In some implementations, the monitoring device may be configured with one or more machine learned modules that implement a machine-learned model trained to determine an expected respiratory rate and/or flow rate based on biological and/or physiological factors related to the patient, such as age, weight, height, and the like. Based on the comparison, the one or more processors of the monitoring device may be configured to calculate a difference between the received breathing pattern data and the threshold breathing pattern data and store the difference in the memory storage unit associated with the monitoring device. For example, the one or more processors may calculate a difference between the left nostril breathing pattern data and the left nostril threshold breathing pattern data, and store the difference in a storage unit of the monitoring device. Similarly, the one or more processors may calculate and store a difference between the right nostril breathing pattern data and the right nostril threshold breathing pattern data, and the mouth breathing pattern data and the mouth threshold breathing pattern data.

Based on the comparison, the one or more processors of the monitoring device determine whether the sensor device is placed correctly on the patient (block 5706). The one or more processors of the monitoring device may determine whether the calculated difference between the received breathing pattern data and the threshold breathing pattern data satisfies a threshold difference. If the calculated difference satisfies the threshold difference, then the one or more processors may determine that the sensor device is placed correctly on the patient. For example, if a threshold difference is a three percent difference from the threshold breathing pattern data, then the one or more processors of the monitoring device determines that the sensor device is placed correctly if the calculated difference for the left nostril, right nostril, and the mouth are within three percent of corresponding threshold breathing pattern data. If the calculated difference does not satisfy the threshold difference, then the one or more processors may determine that the sensor device is placed incorrectly on the patient.

In some implementations, the one or more processors of the monitoring device may be configured to identify a portion of the sensor that is not positioned properly if a calculated difference is close to threshold difference but does not satisfy the threshold difference. For example, if the calculated difference for a left nostril is close to the threshold difference but does not satisfy the threshold difference, then the one or more processors may generate an alert indicating that the positioning of the sensor device on the patient needs adjustment near the left nostril. Similarly, if the one or more processors determine that the calculated difference for the right nostril is close to the threshold difference but do not satisfy their respective threshold differences, then the one or more processors may generate an alert indicating that the position of the sensor device on the patient needs adjustment near the right nostril or the mouth.

If the one or more processors of the monitoring device determine that the sensor device is not placed correctly on the patient (NO' at block 5706), then the method 5700 proceeds to block 5709. The one or more processors of the monitoring device generate alert (block 5709). The alert may specify that the sensor device is not positioned properly on the patient. In some implementations, the one or more processors may specify instructions in the generated alert to reposition the sensor device to an appropriate position on the patient.

If the one or more processors of the monitoring device determine that the sensor device is places correctly on the patient (YES' at block 5706), then the method 5700 proceeds to block 5707. The one or more processors of the monitoring device adjust the threshold breathing pattern data based on the received data indicating breathing patterns (block 5707). In some implementations, the one or more processors may be configured to adjust the threshold breathing pattern data based on a statistical measurement (e.g., a weighted average) of the threshold breathing pattern data and the received breathing pattern data. In some implementations, the one or more processors may store the adjusted threshold breathing pattern data in a storage unit of a monitoring device.

The one or more processors of the monitoring device may be configured to (e.g., using accelerometer data received from sensor device 2) identify a position in a three-dimensional coordinate space system as the current position of the sensor device on the patient (block 5708). The one or more processors of the monitoring device may be configured to determine a set of coordinates in a three-dimensional (3D) coordinate space system and identify the set of coordinates as the position of the sensor device in the 3D coordinate space system. For example, the one or more processors may identify a set of coordinates at a center of a coordinate space system, such as coordinates 0, 0, 0, and identify the set of coordinates 0, 0, 0 as the position of the sensor device in this 3D coordinate system. According to various implementations, the coordinate space may be mapped to the patient's face (or a default face for a patient). The default coordinates (e.g., 0, 0, 0) may be mapped to a facial feature, such as the nose, lips/mouth, chin, or neck of the patient. The one or more processors may store this set of coordinates in a storage unit associated with the monitoring device as a position or a first position of the sensor device. Using the received motion data, the one or more processors of the monitoring device may calculate an offset from the first position. Based on the offset, the one or more processors of the monitoring device may determine a second set of coordinates in the 3D coordinate space system and identify the second set of coordinates as a new or a second position of the sensor device in the 3D coordinate space system. The one or more processors may store the second set of coordinates in a storage unit of the monitoring device as an updated position or a second position of the sensor device in the 3D coordinate space system.

The one or more processors of the monitoring device display a position of the sensor device on the patient in a user interface (block 5709). The one or more processors of the monitoring device may be configured to present a graphical user interface (GUI) on a display device, and display the position of the sensor device in the GUI. The one or processors of the monitoring device display the sensor device in the GUI based on the stored position of the sensor device in the 3D coordinate space system described above. In some implementations, the one or more processors may be configured to generate a virtual representation of a patient's face, head, and/or body and display the sensor device at an appropriate position on the patient's face, head, and/or body. For example, the one or more processors display the sensor device on an upper lip and below the nostrils of the patient's face. In some implementations, the one or more processors may display the virtual representation of a patient's face, head, and/or body with reference to the 3D coordinate space system described above, and display the position of the sensor device based on one or more of the stored positions described above. In some implementations, the monitoring device may receive data from a capacitive sensor and/or skin thermistor of sensor device 2 and based on that data and respiration and accelerometer data, the monitoring device may detect position of the sensor device 2 on the patient.

In some implementations, the one or more processors may be configured to detect a movement of sensor device based on received breathing data and display the movement in real-time in a user interface. Additional details of detecting the movement and displaying the movement in real-time are described below with reference to FIG. 58.

Figure 58:
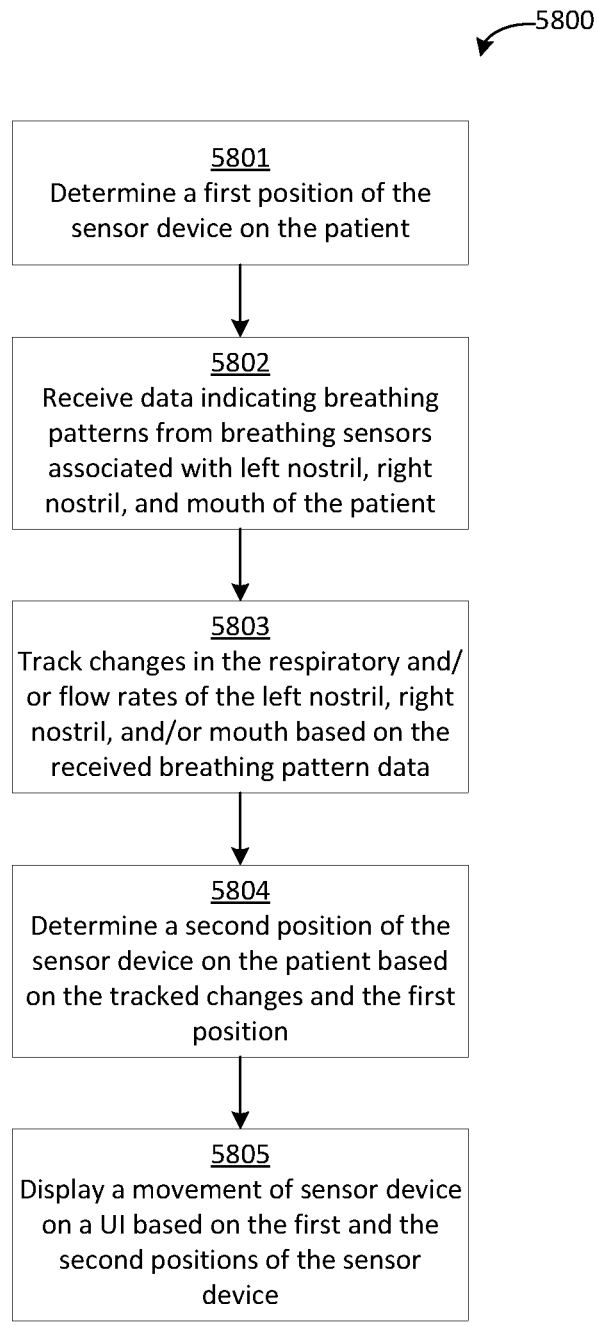
FIG. 58 is a flow chart of an example method of displaying movement of a sensor device on a patient in real-time in a user interface, according illustrative implementations.

Turning now to FIG. 58, there is shown a process to detect a movement of the sensor device on a patient and display the movement in real-time in a user interface. For the purpose of illustrating a clear example, components of the monitoring system 1, and components of the respiration sensors 100a, 100b, previously described herein, may be used to describe the process of detecting a movement of the sensor device based on breathing pattern data and displaying the movement.

The method 5800 includes determining, by a monitoring device, such as the hub 4, a first position of the sensor device on a patient (block 5801). As described above, the one or more processors of the monitoring device may store a position of the sensor device on the patient in a storage unit associated with the monitoring device. The one or more processors of the monitoring device may determine the first position of the sensor device based on the position data stored in the storage unit associated with the monitoring device. For example, the one or more processors may retrieve the most recently stored position data and determine the first position of the sensor device as the most recently stored position. As described above, the monitoring device may receive data from the sensor device in real-time or near real-time, therefore, the determined first position may be the current position of the sensor device on the patient.

The one or more processors of the monitoring device receive data indicating breathing patterns from breathing sensors associated with left nostril, right nostril, and mouth of the patient (block 5802). As described above, such data may be referred to herein as breathing pattern data. The one or more processors track changes in the respiratory and/or flow rates of the left nostril, right nostril, and/or mouth (block 5803). Based on the received breathing pattern data, the one or more processors may determine a respiratory rate and/or flow rate of the left nostril, right nostril, and the mouth of the patient for a current period of time. As described above, the one or more processors may be configured to store respiratory and/or flow rates for each period of time in a storage unit associated with the monitoring device. The one or more processors may compare each determined respiratory and/or flow rate with the respiratory and/or flow rates at previous periods of time. For example, the one or more processors may compare the respiratory and/or flow rate of the left nostril with the respiratory and/or flow rates of the left nostril at previous periods of time. Similarly, the one or more processors may compare the respiratory and/or flow rate of the right nostril and/or the mouth with previously received respiratory and/or flow rates of the right nostril and/or the mouth, respectively. Based on the comparison, the one or more processors may track changes in the respective respiratory and/or flow rates.

The one or more processors of the monitoring device determine a second position of the sensor device on the patient based on the tracked changes and the first position (block 5804). Based on the tracked changes, the one or more processors may determine whether the respiratory and/or flow rates are increasing, decreasing, or are unchanged. The one or more processors may determine that the respiratory and/or flow rates are increasing if the change in the rates are above a threshold amount, decreasing if the change in the rates are below a threshold amount, and unchanged if the change is within a threshold amount. The one or more processors may determine whether the respiratory and/or flow rates are increasing, decreasing, or are unchanged over multiple time periods.

The one or more processors may be configured to compare the changes in the respiratory and/or flow rates for the left nostril, right nostril, and/or mouth with each other to determine a direction of movement of the sensor device on the patient. For example, if the changes for both nostrils (and, in some instances, the mouth) indicate a decrease in the respective respiratory and/or flow rates in a first time period, and data for a first nostril (e.g., the right nostril) indicates an increase in a second subsequent time period, then the one or more processors may determine that the sensor device moved towards the side of the patient corresponding to the opposing nostril (e.g., the left side of the patient, or beyond the left nostril). Based on the direction of movement, the one or more processors may be configured to determine the second position. In some implementations, the one or more processors may be configured to determine a second position by adjusting the first position in the 3D coordinated space system by a predetermined offset amount in the direction of movement.

The one or more processors may display a movement of the sensor device on a user interface based on the first and the second positions of the sensor device (block 5805). The one or more processors may be configured to generate a graphical movement of the sensor device from the first position to the second position, and display the movement on the user interface (e.g. a GUI). As described above, the user interface may display a face and the one or more processors may display the movement of the sensor device on the face.

Figure 59:
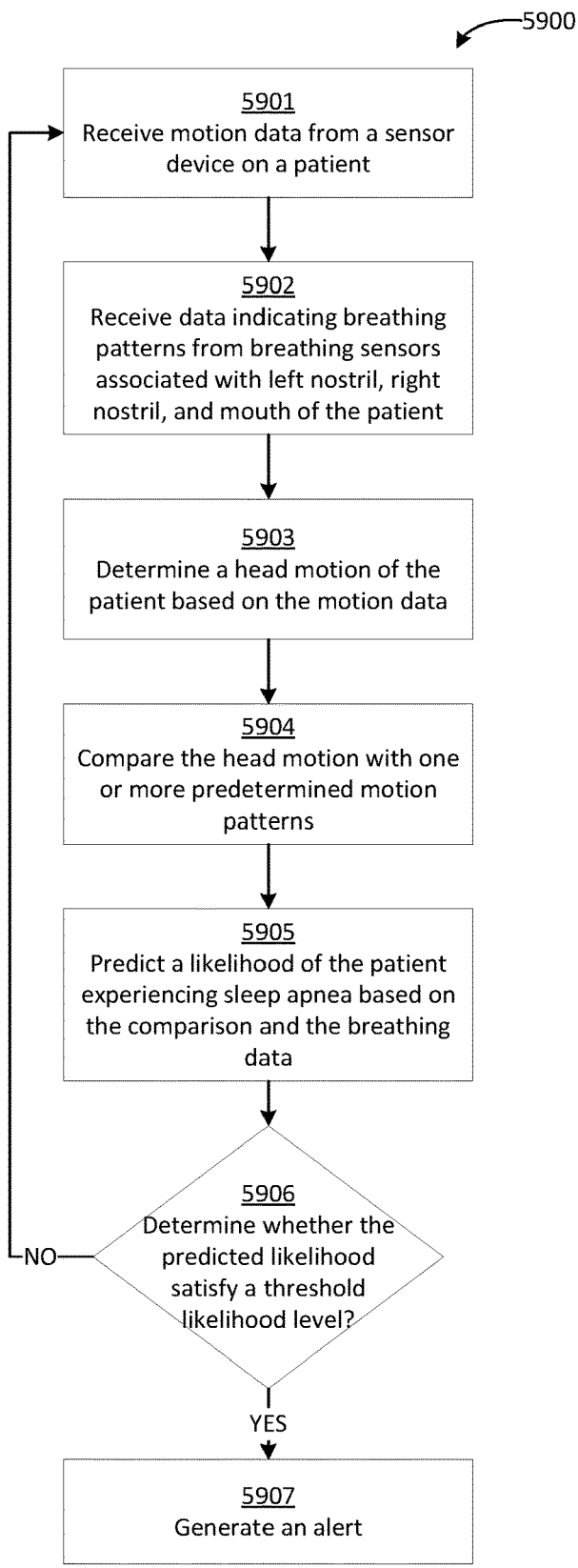
FIG. 59 is a flow chart of an example method of a monitoring device detecting a sleep apnea of a patient, according to illustrative implementations.

Turning now to FIG. 59, there is shown a process to predict a likelihood of the patient experiencing sleep apnea. For the purpose of illustrating an example, components of the monitoring system 1, and components of the respiration sensors 100a, 100b, previously described herein, may be used to describe the process of predicting a likelihood of the patient experiencing sleep apnea.

The method 5900 includes receiving, by a monitoring device, motion data from a sensor device on a face of a patient (block 5901). One or more processors of the monitoring device receive data indicating breathing patterns from breathing sensors associated with left nostril, right nostril, and/or mouth of the patient (block 5902). The one or more processors determine a head motion of the patient based on the received motion data (block 5903). Based on this data, the one or more processors may determine a pattern (e.g., up and down, side to side, and the like) of the head motion. The one or more processors may also be configured to determine a frequency at which the head is moving in a certain pattern. For example, based on the motion data, if the determined pattern of the patient's head motion is up and down, the one or more processors may determine a number of times per ten seconds that a head moves up and down.

The motion data and the breathing data may be compared with one or more predetermined sleep patterns to determine whether the patient is in a normal state of sleep or is experiencing distress. According to various implementations, at least one of the one or more predetermined sleep patterns associated with an indication of sleep apnea. The one or more predetermined sleep patterns may include a predetermined movement pattern of a patient's head relative to a fixed position during a predetermined period of time associated with a predetermined breathing pattern for the predetermined period of time. In some implementations, the movement pattern may correspond to a lip or mouth movement (instead of, e.g., the entire head). An apnea score may be generated based on a strength of similarity between the predetermined movement pattern and a current movement pattern identified by the received motion data, and the predetermined breathing pattern and a current breathing pattern identified by the received breathing data, for a period of time equivalent to the predetermined period of time.

In this regard, the one or more processors compare the determined head motion with the one or more predetermined motion patterns (block 5904). The one or more predetermined motion patterns may be patterns of a head movement associated with sleep patterns. In some implementations, the patterns of a head movement associated with sleep patterns may be head movement patterns associated with sleep apnea. In some implementations, the one or more predetermined motion patterns may be motion patterns identified using machine learned models that were trained using head motion data of patients that suffered sleep apnea. The one or more processors may be configured to generate a an indicator (e.g., a sleep apnea score) that represents how closely the determined head motion matches one or more predetermined head motion patterns based on the comparison of the determined head motion with the one or more predetermined motion patterns.

The one or more processors predict a likelihood of the patient experiencing sleep apnea based on the comparison and the received breathing pattern data (block 5905). The one or more processors may be configured to determine whether the generated indicator satisfies a threshold match level. If the generated indicator does not satisfy the threshold level, then the one or more processors may decrease a likelihood that the patient may experience sleep apnea. If the generated indicator satisfies the threshold level, then the one or more processors may increase the likelihood that the patient may experience sleep apnea. The one or more processors may be configured to further adjust the likelihood that the patient may experience sleep apnea based on the received breathing pattern data. In some implementations, the one or more processors may be configured to identify any irregularities in the patient's breathing, and determine whether any irregularities occur at or near the same time period as the patient's head motion. If any irregularities in the patient's breathing occur at the same time as the patient's head motion, then the one or more processors may increase the likelihood that the patient may experience sleep apnea, and if the irregularities do not occur at or near the same time period as the patient's head motion, then the one or more processors may decrease the likelihood that the patient may experience sleep apnea.

The one or more processors of the monitoring device determine whether the predicted likelihood satisfies a threshold likelihood level (block 5906). In some implementations, the predicted likelihood may be a value that indicates a probability that the patient may experience sleep apnea. In some implementations, the predicted likelihood may be the probability that the patient may experience sleep apnea within a threshold amount of time from a current instance or period of time. If the one or more processors of the monitoring device determine that the predicted likelihood does not satisfy the threshold likelihood level (NO' at block 5906), then the method 5900 proceeds to block 5901. If the one or more processors determine that the predicted likelihood satisfies the threshold likelihood level (YES' at block 5906), then the method proceeds to block 5907. The one or more processors may generate an alert (block 5907). The one or more processors may cause the alert and/or an indication of the alert to be displayed on a display device associated with the monitoring device. In some implementations, on a display device associated with the monitoring device, the one or more processors may cause the alert or the indication of the alert to be displayed together with a graphical representation of the sensor device. In some implementations, the one or more processors may cause the alert to be transmitted to an identifier (e.g., email address, phone number, and the like) of a user, such as a nurse, a doctor, and the like.

In some implementations, the one or more processors may be configured to compare the determined head motion of the patient with one or more predetermined head motion patterns associated with pain. The one or more processors may be configured to generate a pain indicator (e.g., a pain score) that indicates a likelihood that the patient is experiencing pain based on the comparison. For example, the one or more processors may generate a score based on how closely the determined head motion matches one or more predetermined head motion patterns associated with pain. The one or more processors may be configured to display a graphical element indicating the likelihood that the patient is experiencing pain. For example, the one or more processors may cause the generated pain score to be displayed in a GUI on a display device associated with the monitoring device.

According to various implementations, the motion data and/or the breathing data may be compared with one or more predetermined distress patterns to determine whether the patient is in a normal state of sleep or is experiencing distress. In this regard, at least one of the one or more predetermined motion patterns associated with an indication of distress. The one or more predetermined distress patterns may include a predetermined movement pattern of a patient's head relative to a fixed position during a predetermined period of time associated with a predetermined breathing pattern for the predetermined period of time. In some implementations, the movement pattern may correspond to a lip or mouth movement (instead of, e.g., the entire head). A distress or pain score may be generated based on a strength of similarity between the predetermined movement pattern and a current movement pattern identified by the received motion data, and the predetermined breathing pattern and a current breathing pattern identified by the received breathing data, for a period of time equivalent to the predetermined period of time.

Figure 60:
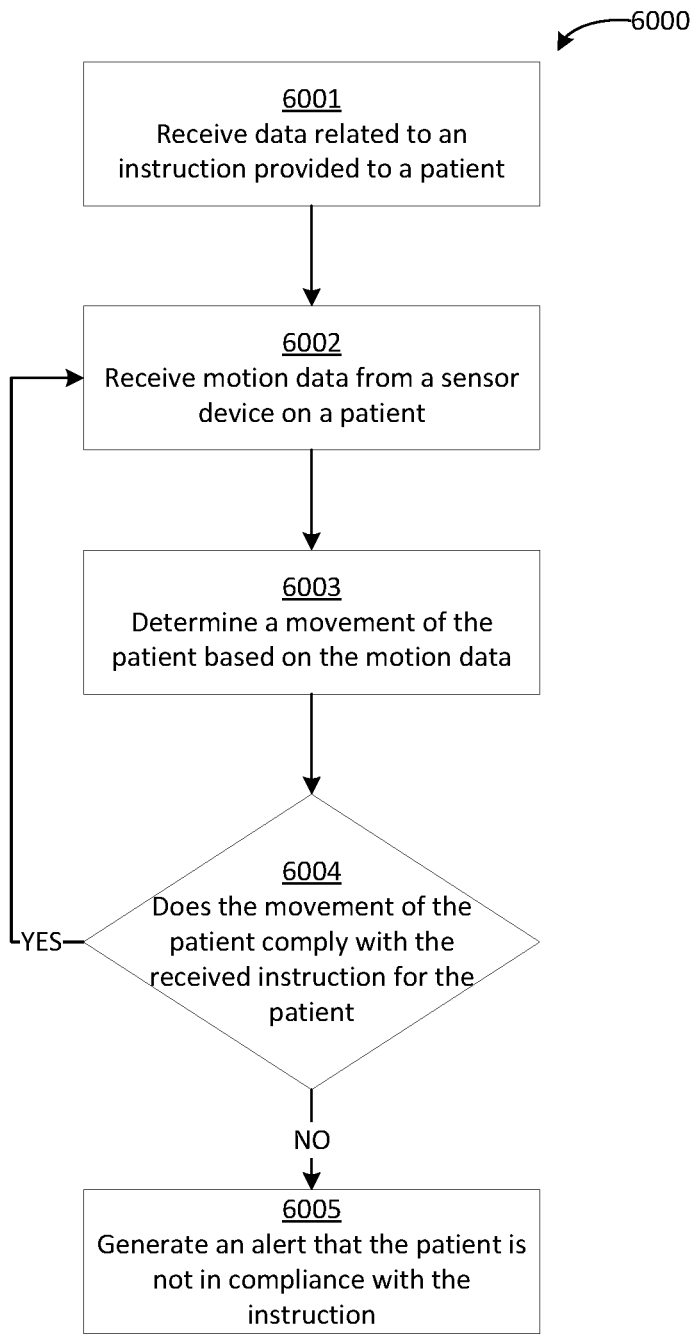
FIG. 60 is a flow chart of an example method of a monitoring device determining whether a patient is in compliance with instructions of a clinician, according to illustrative implementations.

Turning now to FIG. 60, there is shown a process to determine whether a patient is complying with an instruction from a clinician. For the purpose of illustrating a clear example, components of the monitoring system 1, and components of the respiration sensors 100a, 100b, previously described herein, may be used to describe the process of determining whether a patient is complying with an instruction from a clinician.

The method 6000 includes receiving, by a monitoring device, data related to an instruction provided to a patient (block 6001). The data related to the instruction provided to the patient may be provided via an input device associated with the monitoring device. For example, if the instruction provided to the patient is not get out of the bed, then, using a touchscreen display of the monitoring device, the clinician may provide information about the instruction provided to the patient, and the one or more processors may receive the instruction. The one or more processors receive accelerometer data from a sensor device on the patient (block 6002). The one or more processors determine a movement of the patient based on the accelerometer data (block 6003). The one or more processors may be configured to determine a motion based on the received accelerometer data and compare the determined motion with predetermined motion patterns that indicate a movement of a patient. Based on the comparison, the one or more processors may determine a movement (e.g., sitting up, standing up, walking, and the like) of the patient.

The one or more processors determine whether the movement of the patient complies with the received instruction for the patient (block 6004). For example, if the received instruction is that the patient should lie down, and the determined movement indicates that the patient is sitting up, then the one or more processors determine that the movement of the patient does not comply with the received instructions. If the one or more processors determine that the movement of the patient complies with the received instruction (YES' at block 6004), then the method proceeds to block 6002. If the one or more processors determine that the movement of the patient does not comply with the received instruction (NO' at block 6004), then the method proceeds to block 6005. The one or more processors generate an alert that the patient is not in compliance with the instruction (block 6005). The one or more processors may cause the alert to be displayed on a display device associated with the monitoring device. In some implementations, the one or more processors may cause the alert to be transmitted to an identifier (e.g., email address, phone number, and the like) of a user, such as a nurse, a doctor, and the like.

Figure 61:
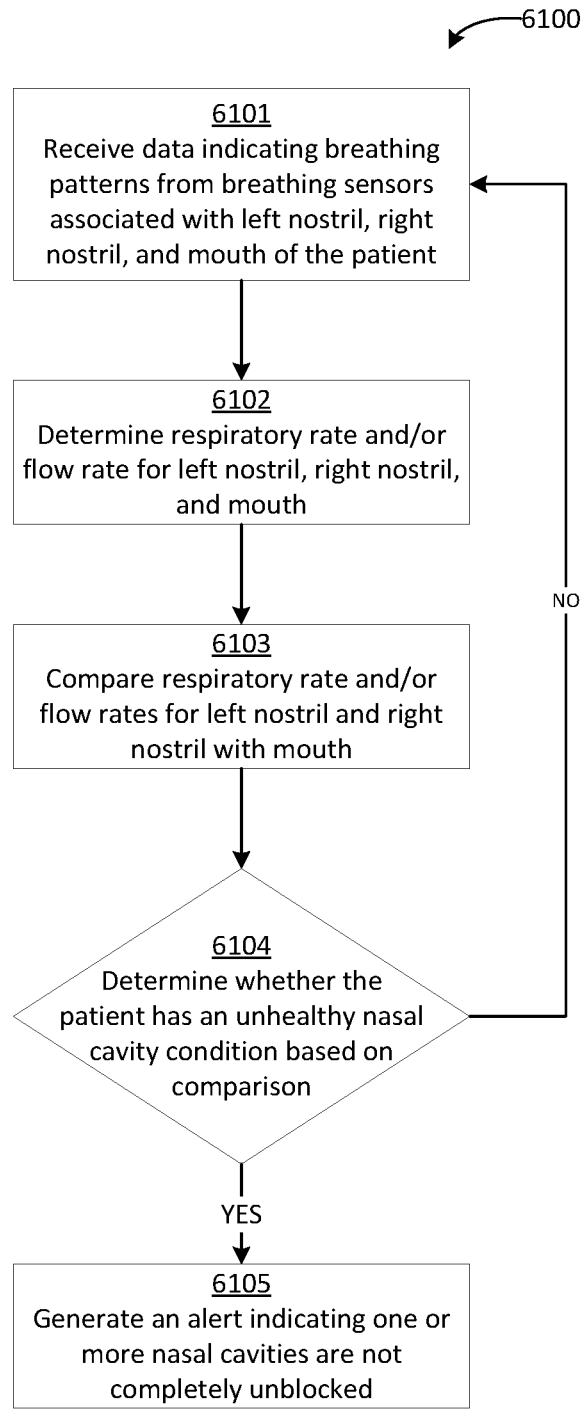
FIG. 61 is a flow chart of an example method of a detecting nasal cavity conditions based on received breathing pattern data, according to illustrative implementations.
Figure 62:
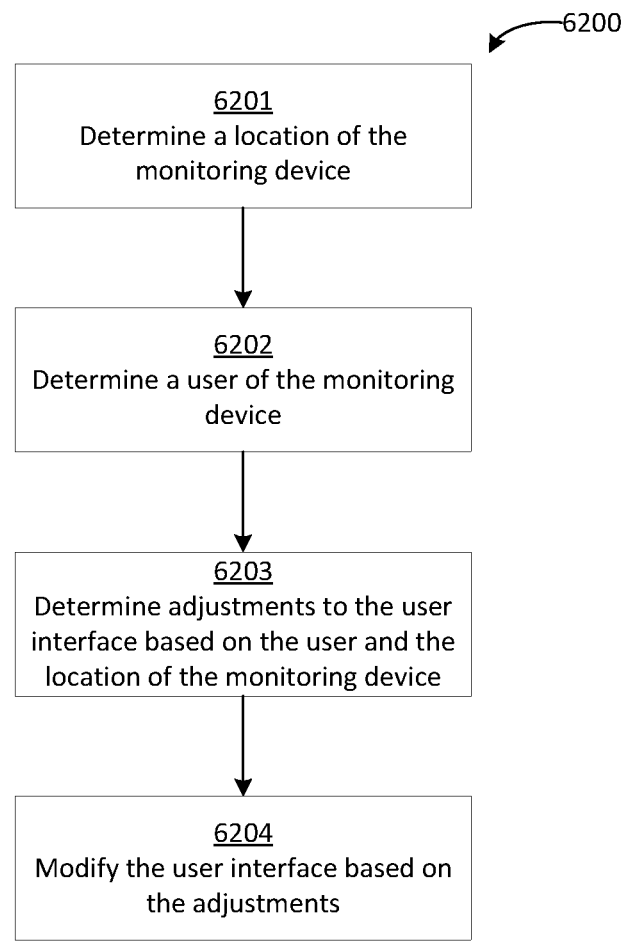
FIG. 62 is a flow chart of an example method of adjusting a user interface of a monitoring device, according to illustrative implementations.

Turning now to FIG. 61, there is shown a process to detect nasal cavity conditions based on received breathing pattern data. For the purpose of illustrating a clear example, components of the monitoring system 1, and components of the respiration sensors 100a, 100b, previously described herein, may be used to describe the process of detecting nasal cavity conditions based on received breathing pattern data.

The method 6100 includes receiving, by one or more processors of the monitoring device, data indicating breathing patterns from breathing sensors associated with left nostril, right nostril, and mouth of the patient (block 6101). The one or more processors determine respiratory rate and/or flow rate for left nostril, right nostril, and mouth based on the received breathing pattern data (block 6102). The one or more processors compare respiratory and/or flow rates of the left nostril and right nostril with the respiratory and/or flow rates of mouth of the patient (block 6103). The one or more processors may be configured to calculate a difference based on the comparison of the respiratory and/or flow rates. For example, the one or more processors may calculate a difference between respiratory and/or flow rates of left nostril and mouth of the patient, and calculate another difference between respiratory and/or flow rates of right nostril and mouth of the patient. The one or more processors may be configured to store the calculated differences in a storage unit associated with the monitoring device.

The one or more processors determine whether the patient has an unhealthy nasal cavity condition based on the comparison (block 6104). The one or more processors determine the patient has an unhealthy nasal cavity condition if the respiratory and/or flow rate of mouth of the patient is greater than the respiratory and/or flow rate left nostril and/or right nostril. In some implementations, the one or more processors may be configured to compare the calculated and/or stored differences with predetermined threshold difference values associated with nasal cavity conditions. If the one or more processors determine that a calculated difference satisfies a predetermined threshold difference value, then the one or more processors may be configured to determine that corresponding nasal cavity is not completely unblocked or healthy.

For example, the one or more processors may compare the calculated difference between the left nostril and mouth with a threshold difference, and if the calculated difference satisfies the threshold difference, then the one or more processors may determine that the nasal cavity of the left nostril is not completely unblocked or healthy. Similarly, if the one or more processors compare the calculated difference between the right nostril and mouth with a threshold difference, and if the calculated difference satisfies the threshold difference, then the one or more processors may determine that the nasal cavity of the right nostril is not completely unblocked or healthy. The one or more processors of the monitoring device generates an alert indicating one or more nasal cavities are not completely unblocked (block 6105). In some implementations, the one or more processors may indicate each nasal cavity that is determined to not to be completely unblocked in the alert. For example, if the one or more processors determine that the left nasal cavity is not completely unblocked, then the one or more processors may indicate in the alert that the left nasal cavity is not completely unblocked. Similarly, if the one or more processors determine that the right nasal cavity not completely unblocked, then the one or more processors may indicate in the alert that the right nasal cavity is not completely unblocked. The one or more processors may cause the generated alert to be displayed on a display device associated with monitoring device. The one or processors may generate an alert indicating one or more nasal cavities are not unhealthy Turning now to FIG. 62, there is shown a process to adjust or modify a user interface based on location of the monitoring device. For the purpose of illustrating a clear example, components of the monitoring system 1, and components of the respiration sensors 100a, 100b, previously described herein, may be used to describe the process of adjusting or modifying a user interface based on a location of the monitoring device.

The method 6200 includes determining, by one or more processors of a monitoring device, a location of the monitoring device (block 6201). In some implementations, the monitoring device may be configured with a geographical positioning system, and the one or more processors may be configured to determine a location of the monitoring device based on data from the geographical position system related to location information of the monitoring device. In some implementations, the monitoring device may be configured to receive location information from one or more beacon devices, and the one or more processors may be configured to determine location of the monitoring device based on the location information received from one or more beacon devices. The one or more processors may be configured to associate certain area or units within a medical facility with certain location information. The one or more processors may determine an area or unit with a medical facility based on the location information and the stored associations. For example, if a certain location information is associated with a general ward and certain other location information is associated with intensive care unit, and if the received location information matches the location information associated with the general ward, then the one or more processors may determine that the current monitoring device is in the general ward.

The one or more processors determine a user of the monitoring device (block 6202). The one or more processors may be configured to determine whether any user is currently logged into the monitoring device. For example, based on a stored login data, the one or more processors determine an identifier of a user that is currently logged in, and the based on the identifier, the one or more processors may determine a current user of the monitoring device. The one or more processors determine adjustments to the user interface based on the user and the location of the monitoring device (block 6203). The one or more processors may be configured to track and store information related to various user interface adjustments made by a user over certain period of time and associate such adjustments with the user and the location of the monitoring device. For example, a user, such as a nurse, may adjust a default user interface by adding certain graphical components and/or removing certain graphical components, and the user may make these adjustments over period of 15 days every time the user interacts with a monitoring device in a general ward area, then the one processors may track the addition and deletion of the graphical items and associate these additions and deletions with the nurse and the general ward.

Based on the determined user of the monitoring device and the location of the monitoring device, the one or more processors may determine the adjustments that may be made to the user interface. The one or more processors modify the user interface based on the determined adjustments (block 6204). The one or more processors may modify the user interface by adding and/or deleting graphical components. Similarly, the one or more processors may modify the user interface by adjusting size of the graphical components, text displayed in the user interface, the manner in which data is displayed to a user and the like. Thus, once the user is ready to interact with the monitoring device at a particular location (e.g., an intensive care unit), then the monitoring device automatically modifies the user interface in order to display a user interface that the user desires.

XII. Chronic Obstructive Pulmonary Disease (COPD) Monitoring

Figure 63:
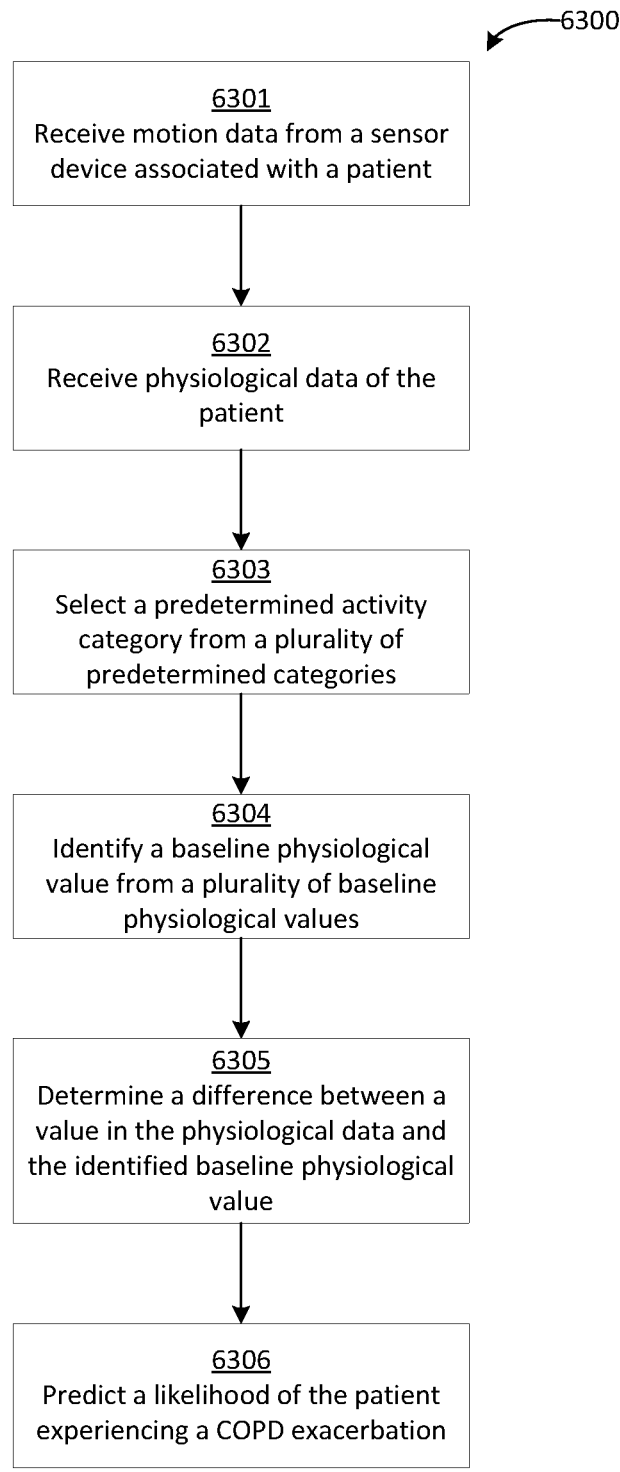
FIG. 63 is a flow chart of an example method of predicting a likelihood of a chronic obstructive pulmonary disease (COPD) exacerbation, according to illustrative implementations.

Turning now to FIG. 63, there is shown a process to predict a likelihood of a patient experiencing a chronic obstructive pulmonary disease (COPD) exacerbation. In some implementations, an exacerbation of COPD may refer to worsening of COPD symptoms. For the purpose of illustrating an example, components of the monitoring system 1, and components of the sensor device 2 (including e.g., respiration sensors 100*a*, 100*b*), previously described herein, may be used to describe the process of predicting a likelihood of a patient experiencing a COPD exacerbation. As described above, in some implementations, a monitoring device 4 may include a memory storage unit and/or may be communicatively coupled with a remotely located storage unit (e.g., a cloud-based storage unit). One or more processors of the monitoring device may be configured to store data in any storage unit associated with the monitoring device.

The method 6300 includes receiving, by a monitoring device 4, motion data (e.g., movement data) from a sensor device associated with a patient (block 6301). As described above, motion data may include data from an accelerometer (and/or gyroscope) of a sensor device, such as the sensor device 2. The motion data may indicate a movement of the patient. For example, the motion data may indicate whether a patient is moving or whether a patient is at rest. In some implementations, the monitoring device 4 may determine a heart rate of a patient based on the motion data.

The monitoring device 4 may determine a heart rate of the patient based on the detected movements of the body of the patient. As described above, an accelerometer, such as the accelerometer 1150 (shown in FIG. 41), of the sensor device, such as the sensor device 2, may be configured to detect back and forth cyclical movement of the body of a patient at the phase of a heartbeat of the patient. In some implementations, the accelerometer 1150 of the sensor device 2 may be configured to detect the heart's rotation along its long-axis, which also generates rotational force around longitudinal axis of the patient's body at a phase of the heartbeat. The monitoring device 4 may detect the longitudinal movement or rotational movement around the patient's body's longitudinal axis and determine a heartbeat or heartbeats per minute value from the data of the accelerometer. In some implementations, the accelerometer 1150 can also detect rise and fall of a patient's chest or other thoracic movement and determine a heart rate based on the detected rise and fall of the patient's chest.

The monitoring device 4 receives physiological data of the patient from the sensor device (block 6302). The physiological data of the patient may include data indicating breathing patterns from breathing sensors of the sensor device 2. In some implementations, the monitoring device 4 may be coupled to one or more external medical devices, such as a pulse oximeter. The monitoring device 4 may receive physiological data that includes amount of oxygen in patient's blood from the one or more external medical devices, such as the pulse oximeter. The monitoring device 4 may determine a level of activity of the patient based on the physiological data. For example, the monitoring device 4 may determine a level of activity of the patient based on the heart rate and/or peripheral capillary oxygen saturation (SpO2) data of the patient. A level of activity may indicate a certain activity (e.g., walking, exercising, running, and the like) and may be associated with a predetermined activity category. Additional details of determining a level of activity are described herein with reference to FIG. 64.

As described above, predetermined activity category may be associated with a level of activity. The monitoring device 4 may be configured to determine a predetermined activity category based on a determined level of activity. As shown in FIG. 63, the monitoring device 4 selects the predetermined activity category from a plurality of predetermined activity categories (block 6303). The monitoring device 4 may be configured to receive location data related to the patient from sensor device 2. The monitoring device 4 may determine a path travelled by the patient based on the location data and the motion data of the patient.

In some implementations, the monitoring device 4 may be configured to determine a number of times a patient travelled a path, and the one or more processors of the monitoring device 4 may be configured to display the number of times the patient travelled a path in a GUI on a display device associated with the monitoring device 4. In some implementations, the monitoring device 4 may be configured to generate a graphical path line for each path travelled by the patient, and displays the generated graphical path lines on a GUI displayed on a display device associated with the monitoring device 4. The monitoring device 4 may be configured to indicate a number of times the path travelled by the patient by a size of a graphical path generated. For example, for each time the patient travelled a path, the monitoring device 4 may increase the size of the graphical path. Similarly, in some implementations, the monitoring device 4 may decrease size of the graphical path if a patient does not travel on a path for a threshold period of time. In some implementations, the monitoring device 4 may be configured to determine whether a patient travelled vertically based on the motion data. As described above, the motion data may include accelerometer data, positional data, and/or orientation data, and the monitoring device 4 may determine whether a patient travelled vertically (e.g., going up stairs, going down stairs, and the like). The monitoring device 4 may be configured to display a vertical position of the patient in a GUI on a display device associated with the monitoring device 4.

In some implementations, the monitoring device 4 may be configured to associate one or more baseline physiological values with a path. In some implementations, the monitoring device 4 may associate a baseline physiological value with a determined activity category of the patient. The monitoring device 4 may generate the baseline physiological value based on physiological data measured during a period of time the patient traveled the associated path and/or during which the motion data of the patient is collected and/or measured.

The monitoring device 4 identifies a baseline physiological value from a plurality of baseline physiological values (block 6304). The monitoring device 4 may be configured to identify the baseline physiological value based on the determined activity category and/or path travelled by the patient. The monitoring device determines a difference between a value in the physiological data and the identified baseline physiological value (block 6305). For example, the monitoring device 4 may calculate a difference between the baseline respiration rate and the respiration rate indicated by the received breathing pattern data. Similarly, the monitoring device 4 may calculate a difference between the baseline flow rate and the flow rate indicated by the received breathing pattern data. The monitoring device 4 predicts a likelihood of the patient experiencing a COPD exacerbation (block 6306). The monitoring device 4 may predict the likelihood based on the calculated difference between the baseline flow rate and respiration rate and the flow rate and respiration rate received from the data indicated by breathing pattern data.

While the above describes one or more processors of the monitoring device performing the process to predict a likelihood of a patient experiencing a COPD exacerbation, one skilled in the art should recognize that one or more processors of the sensor device may be configured to perform the process to predict a likelihood of a patient experiencing a COPD exacerbation in accordance with the process described in FIG. 63.

Figure 64:
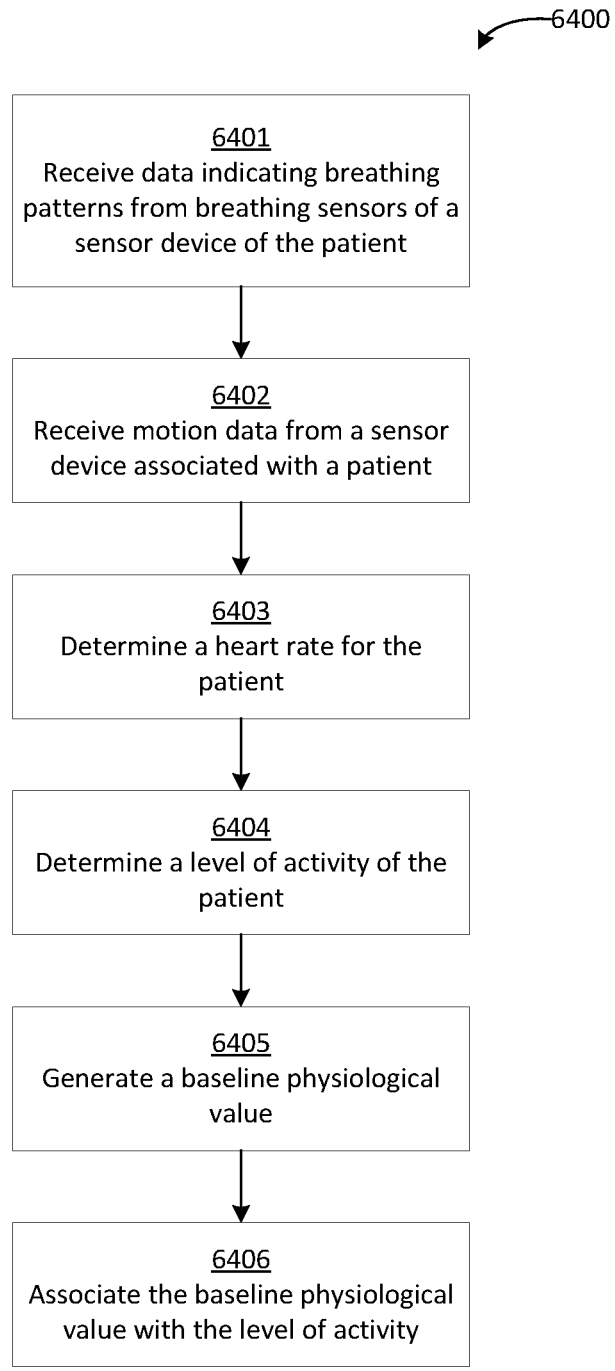
FIG. 64 is a flow chart of an example method of determining an activity level of a patient and associating the activity level with one or more baseline physiological values, according to illustrative implementations.

Turning now to FIG. 64, there is shown a process to determine an activity level of a patient and associate the activity level with one or more baseline physiological values. For the purpose of illustrating an example, components of the monitoring system 1, and components of the respiration sensors 100a, 100b, previously described herein, may be used to describe the process of determining an activity level of a patient and associating the activity level with one or more baseline physiological values.

The method of 6400 includes receiving, by one or more processors of a monitoring device 4, data indicating breathing patterns from breathing sensors of a sensor device of the patient (block 6401). As described above, the breathing pattern data may indicate breathing patterns from breathing sensors associated with left nostril, right nostril, and/or mouth of the patient. In some implementations, the one or more processors of the monitoring device 4 may determine a respiration rate and/or flow rate of the patient based on the received breathing pattern data. In some implementations, the received breathing pattern data may include a respiration rate and/or flow rate of the patient. The one or more processors of the monitoring device 4 receive motion data from a sensor device associated with the patient (block 6402). The motion data may include data from an accelerometer, such as the accelerometer 1170, of the sensor device. The received motion data may indicate how frequently a patient is moving. The received motion data may be captured and/or measured while the received breathing pattern data is collected and/or measured. The one or more processors of the monitoring device 4 may associate the received breathing pattern data with the received motion data, and may store the received breathing pattern data in association with the received motion data in a storage unit associated with the monitoring device 4.

The one or more processors of the monitoring device 4 determines a heart rate of the patient (block 6403). The received motion data may include data from an accelerometer, such as the accelerometer 1170, of the sensor device, such as the sensor device 2. As described above, the one or more processors of the monitoring device 4 may determine a heart rate based on the data from the accelerometer of the sensor device. The one or more processors of the monitoring device 4 determines a level of activity of the patient (block 6404). The one or more processors of the monitoring device 4 may determine a level of activity of the patient based on a heart rate of the patient. The monitoring device 4 may be configured with a set of rules that specify different levels of activity for different ranges of heart rates.

For example, the set of rules may specify that a patient is moving if a heart rate of the patient is between a first range of heart rates, such as a heart rate between 80 and 100, is resting or idle if the heart rate of the patient is between a second range of heart rates, such as a heart rate between 70 and 75, is sleeping if the heart rate is between a third range of heart rates, such as a heart rate between 55 and 60, and is engaged in a high effort activity if the heart rate is between a fourth range of heart rates, such as a heart rate between 110 and 175. Examples of a high effort activity may include, but are not limited to, exercise, running, walking up and/or down a set of stairs, and the like. The one or more processors of the monitoring device 4 may be configured to determine a level of activity based on the set of rules and the heart rate of the patient.

In some implementations, for each level of activity, the set of rules may specify a threshold amount of time during which a heart rate of patient should satisfy the corresponding range of heart rates. For example, the set of rules may specify that a heart rate of a patient should be between 80 and 100 for at least 5 seconds to determine that the patient is walking. In some implementations, the set of rules may specify different threshold amounts of time for different levels of activity. Continuing with the previous example, the set of rules may specify that a heart rate of a patient should be between 110 and 175 for at least 15 seconds to determine that the patient is engaged in a high effort activity. The one or more processors of the monitoring device 4 may be configured to determine a level of activity of the patient based on whether a heart rate of a patient is within a range of heart rates for a threshold amount of time.

As described above, the sensor device, such as the sensor device 2, may be configured to transmit data continuously in real-time or near real-time, and the one or more processors may be configured to store the determined heart rates of the patient in association with the time at which the heart rate is determined and/or the time at which corresponding accelerometer data is received and/or captured. The one or more processors of the monitoring device 4 may be configured to determine a level of activity of the patient by determining whether the heart rate of the patient is within a specified range of heart rates for the level of activity for a corresponding threshold duration of time based on the stored heart rates and their associated times. For example, the one or more processors of the monitoring device 4 may determine whether the patient is engaged in a high effort activity by determining whether the heart rate of a patient is between 80 and 100 for at least 5 seconds based on the stored heart rates for the past 5 seconds.

The one or more processors of the monitoring device 4 may be configured to store the received breathing pattern data in association with the determined level of activity in a storage unit associate with the monitoring device. The one or more processors of the monitoring device 4 generates a baseline physiological value (block 6405). The one or more processors of the monitoring device may be configured to determine a baseline physiological value based on corresponding physiological values over a threshold period of time. As described above, examples of physiological values may include, but are not limited to, respiration rate of a patient, a flow rate of the patient, and the like.

As described above, in some implementations, the received breathing pattern data may include respiration rate of the patient and/or flow rate of the patient, and the one or more processors of the monitoring device 4 may be configured to store the respiration rate and/or flow rate in association with information related to a time at which the respiration rate and/or flow rate is captured and/or measured. For example, if the threshold period of time is 30 days, then the one or more processors of the monitoring device 4 may determine a baseline respiration rate based on respiration rates of the patient over the last 30 days. Similarly, if the threshold period of time is 30 days, then the one or more processors of the monitoring device may determine a baseline flow rate based on the flow rates of the patient over the last 30 days.

In some implementations, the one or more processors of the monitoring device 4 may determine whether the determined level of activity is associated with a baseline physiological value. If the determined level of activity is associated with a baseline physiological value, then the one or more processors of the monitoring device may be configured to generate a new baseline physiological value by updating the associated baseline physiological value based on the received breathing pattern data. For example, if the determined level of activity of the patient is associated with a baseline respiration rate and a baseline flow rate, then the one or more processors of the monitoring device 4 may generate a new baseline respiration rate and a new baseline flow rate based on the received respiration rate and received flow rate, respectively.

The one or more processors of the monitoring device 4 may associate the generated baseline physiological value with the determined level of activity (block 6406). For example, if the determined level of activity of the patient is moving, then the one or more processors may store the generated baseline respiration rate in association with the determined level of activity. Similarly, the one or more processors may store the generated baseline flow rate in association with the determined level of activity.

While the above describes one or more processors of the monitoring device performing the process to determine an activity level of a patient and associate the activity level with one or more baseline physiological values, one skilled in the art should recognize that one or more processors of the sensor device may be configured to determine an activity level of a patient and associate the activity level with one or more baseline physiological values in accordance with the process described in FIG. 64.

Figure 65:
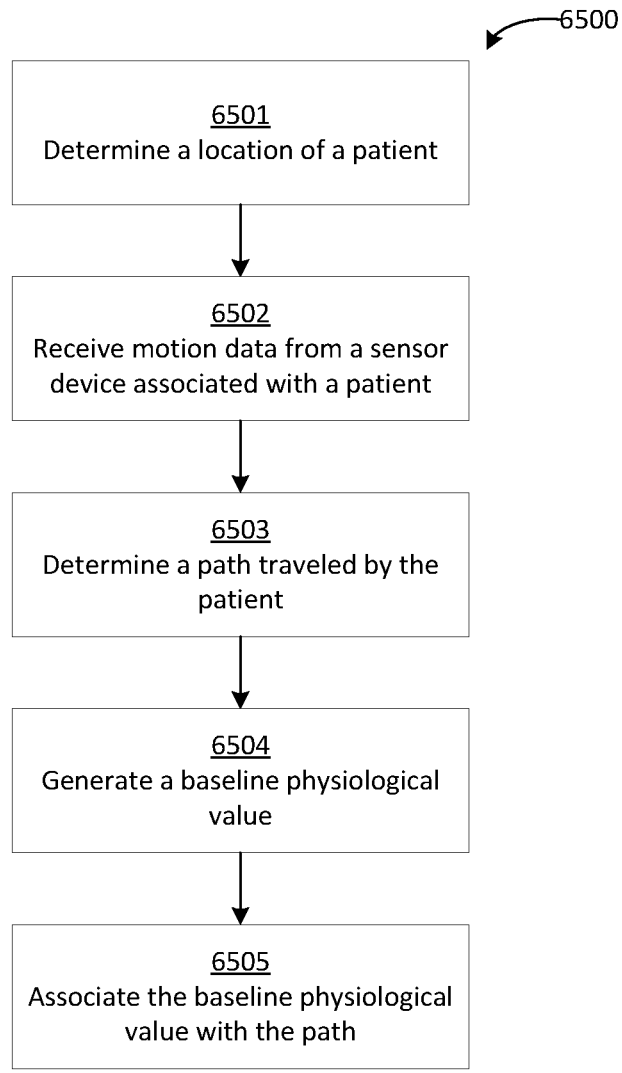
FIG. 65 is a flow chart of an example of determining a path traveled by the patient and associating the path with one or more baseline physiological values, according to illustrative implementations.

Turning now to FIG. 65, there is shown a process to determine a path traveled by the patient and associate the path with one or more baseline physiological values. For the purpose of illustrating an example, components of the monitoring system 1, and components of the respiration sensors 100*a*, 100*b*, previously described herein, may be used to describe the process of determining a path traveled by the patient and associate the path with one or more baseline physiological values.

The method 6500 includes determining, by one or more processors of a monitoring device 4, location of a patient (block 6501). As described above, in some implementations, the monitoring device may be configured with a geographical positioning system, and the one or more processors may be configured to determine a location of the monitoring device based on data from the geographical position system related to location information of the monitoring device. In some implementations, the monitoring device may be configured to receive location information from one or more beacon devices, and the one or more processors may be configured to determine location of the monitoring device based on the location information received from one or more beacon devices.

The one or more processors may be configured to associate an area (e.g., kitchen, living room, bedroom, and the like) of a patient's home with location information. The one or more processors may determine an area of a patient's home based on the location information and the stored associations. For example, if location information is associated with the kitchen and other location information is associated with living room, and if the received location information matches the location information associated with the kitchen, then the one or more processors may determine that the current monitoring device is in the kitchen.

The one or more processors of the monitoring device 4 receive motion data from a sensor device associated with a patient (block 6502). As described above, the one or more processors of the monitoring device 4, determine a level of activity of the patient based on the motion data. The one or processors of the monitoring device 4 determine a path traveled by the patient (block 6503). The one or more processors of the monitoring device 4 determine the path based on the determined location of the patient and the received motion data. For example, the one or more processors may determine whether the patient is moving and determine a second location of the patient based on the movement of the patient. In some implementations, the motion data from the sensor device may include acceleration, position, angular rotation, and/or orientation data related to the patient, and the one or more processors of the monitoring device may determine whether the patient is travelling in a vertical direction based on the acceleration, position, angular rotation, and/or orientation data related to the patient.

In some implementations, the monitoring device 4 may be configured with one or more machine learned models that are trained to detect paths travelled by a patient. The one or more machine learned models may be trained with inputs from a sensor device, such as motion data, breathing patterns of a person associated with the sensor device, and the like. In some implementations, the one or more machine learned models may be trained to detect stairs or other structures based on the movement data of the patient. For example, the one or more machine learned models may be trained to detect stairs based on orientation data received from the sensor device, and the patient moving vertically. In some implementations, the one or more machine learned models may be trained to detect obstacles (e.g., couch, table, and the like) in a path travelled by the patient.

Figure 66A:
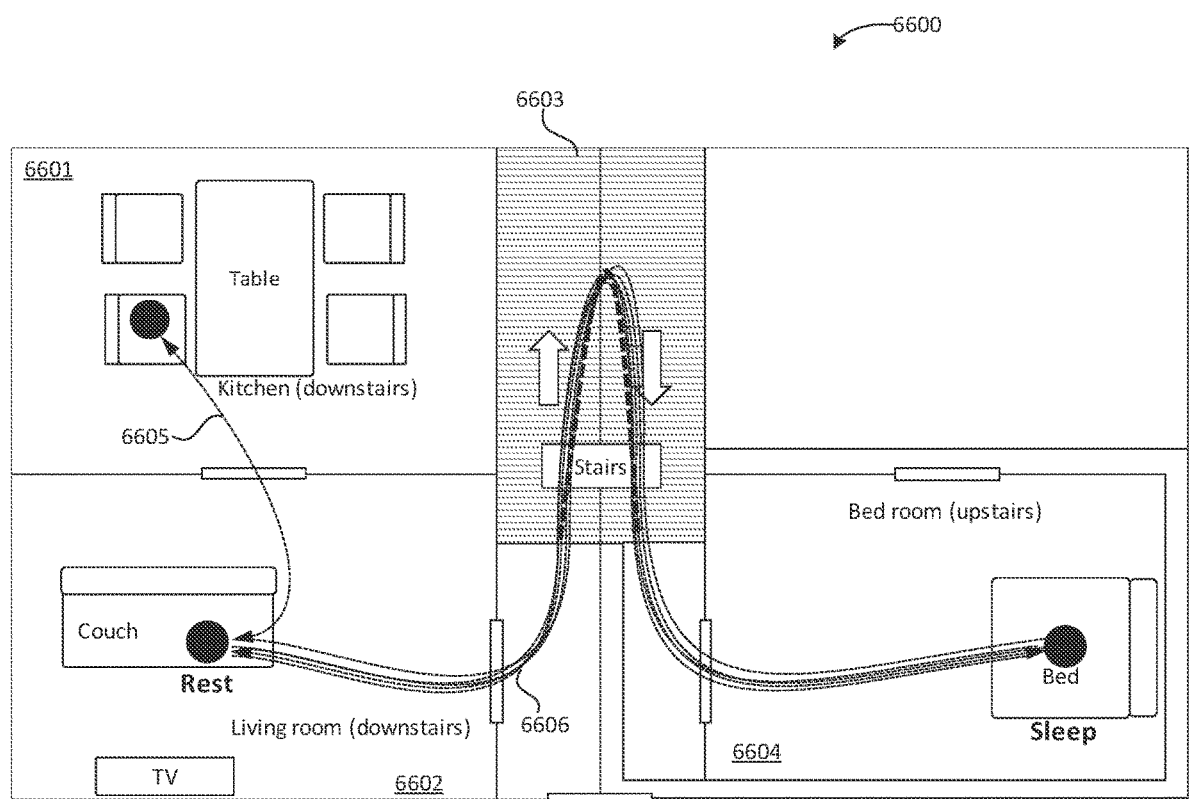
FIG. 66A illustrates an example graphical representation of a bounded area displaying graphical representations of paths travelled by a patient, according to illustrative implementations.

The one or more processors may be configured to generate a graphical representation of a bounded area, such as a virtual map or a virtual floor plan of a structure where the patient resides. As described above, the one or more processors may be configured to generate graphical lines that indicate the paths travelled by the patient. The one or more processors may include the generated graphical lines in the generated graphical representation of the bounded area. An example of a generated graphical representation of a bounded area including the graphical representation of paths travelled by a patient is shown in FIG. 66A. As shown in FIG. 66A, graphical representation of bounded area 6600 includes graphical generated paths 6605, 6606. In some implementations, a user and/or a patient may provide inputs to a monitoring device that indicate location information, such as kitchen 6601, living room 6602, bedroom 6604, and the like, for certain portions of the graphical representation of the bounded area, and the one or more processors of the monitoring device may display the location information in the generated graphical representation of a bounded area, as shown in FIG. 66A.

The one or more processors of the monitoring device generate a baseline physiological value (block 6504). As descried above, the one or more processors of the monitoring device may determine a baseline physiological value, such as a baseline respiration rate value and/or baseline flow rate value, based on the respiration rate data, and flow rate data, respectively. The one or more processors of the monitoring device associate the generated baseline physiological value with the determined path (block 6505). The one or more processors of the monitoring device may store the generated physiological value in association with the determined path in a storage device associated with the monitoring device.

In some implementations, an existing baseline physiological value may be associated with the determined path, and an indicator may be stored in a memory of the monitoring device indicating that the determined path is associated with a baseline physiological value. The one or more processors of the monitoring device may identify existing baseline physiological value based on the determined path, and generate a new baseline physiological value by updating the existing baseline physiological value associated with the determined path based on received physiological data. For example, as described above, the one or more processors of the monitoring device may generate a new baseline respiration rate by updating an existing baseline respiration rate based on the respiration rate data. Similarly, the one or more processors may generate a new baseline flow rate by updating an existing baseline flow rate based on the flow rate data. The one or more processors of the monitoring device may associate the generated new baseline physiological value with the determined path.

While the above describes one or more processors of the monitoring device performing the process to determine a path traveled by the patient and associate the path with one or more baseline physiological values, one skilled in the art should recognize that one or more processors of the sensor device may be configured to determine a path traveled by the patient and associate the path with one or more baseline physiological values in accordance with the process described in FIG. 65.

Figure 66B:
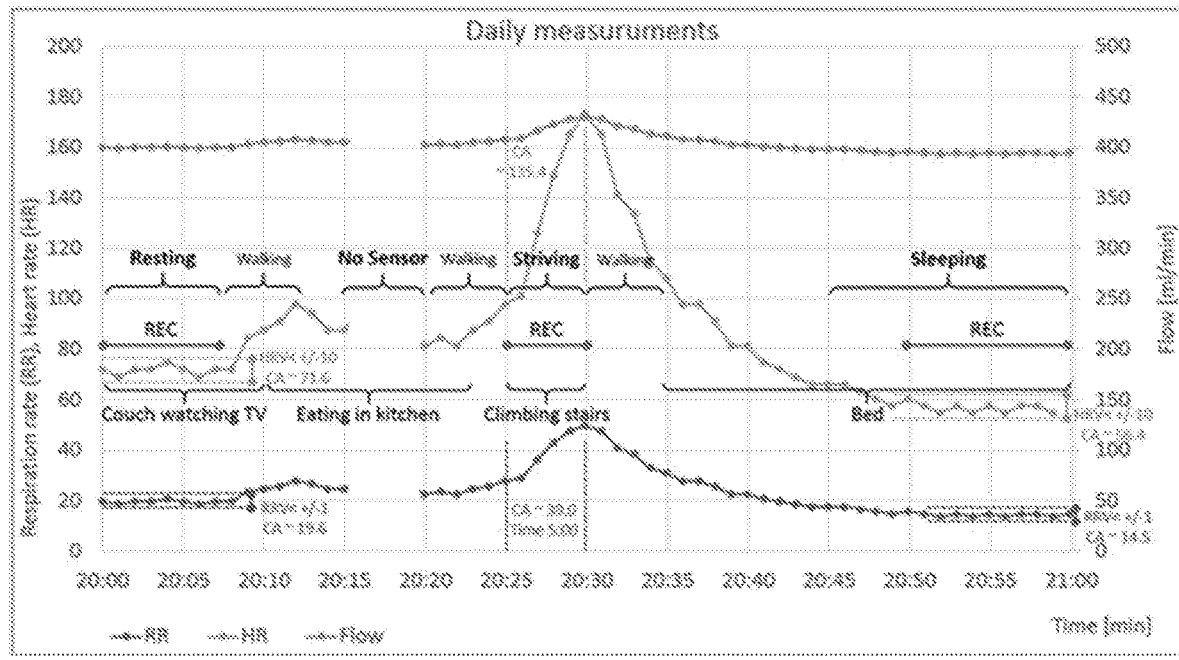
FIG. 66B illustrates an example graphical display of real time measurements for indicating whether a patient is likely to experience a health event, according to illustrative implementations.

FIG. 66B illustrates a first graphical display of real time measurements for indicating whether a patient is likely to experience a health event, according to various aspects of the subject technology. The patient's physiological parameters measured with the sensor device 2. For example, respiration flow (Flow), respiration rate (RR), the sensor location on face, as well as position/movement (e.g., head posture/movement, walking, falling down), and hear rate (HR) may be determined as previously described above. The patient's location may also be detected and tracked based on various technologies (e.g., within the device or in communication with various aspects of the system). For example, location may be detected using SiLabs BTLE tracking device, Wifi tracking, GPS, and the like. In this regard, monitoring device 4 may determine the patient's real time location, movement, path, and time used for the movement.

The device and system of the subject technology enable the patient's location and movement in a house can be detected with less than 25 cm accuracy (e.g., using BTLE tracking, which may include three dimensional vector with direction ($\alpha$, $\beta$) and length L=>location/speed). This location information can then be mapped with the layout of patient's house, as described above. Changes in patient's efforts can be approximated by combining patient's location/movement & time with the parameter data from the sensors. Oxygenation can also be detected, which may affect to efforts of working approximations. Approximations may then be made and graphically displayed as in FIGS. 66A and 66B.

In the depicted example, the patient may be resting for a period of time ("Resting"). A rest state measurement may include, for example, no movement by the patient over a period of time ($\alpha$, $\beta$, L constant). For example, the patient may be watching television (e.g., on a couch) in the living room. The monitoring device 4 may identify the location as a couch and/or living room based on previously inputted data for the patient and location data received from sensor device 2. In the depicted example, location and sensor information are recorded for example for 10 minutes to get rest state trend in the living room. Data received from the sensor device 2 shows that patient is in the upright position (sitting), but no movement. RR and flow are constant, as well as HR. The monitoring device 4 determines, based on a combination of these factors, that the patient is resting, and the designation is visually indicated on the graphical display of FIG. 66B.

The graphical display depicts an amount of flow or respiration over a period of time. IN the depicted example, the period of time is one hour. In some sub-periods of time during the example hour, no sensor activity may be detected. For example, the patient may go in to the kitchen to eat. In this regard, the patient location detection shows movement from the couch in the living room to the kitchen chair ($\alpha$, L) and no movement after that ($\alpha$, $\beta$, L constant). The sensor first shows upright position and walking (steps). Then the sensor device 2 detects that the patient is in the upright position and location on the chair. From this data the monitoring device 4 may indicate that the patient is sitting on the chair by the kitchen table.

During another period, the sensor location shows that sensor is not on the face (RR, Flow and HR=0) and measurement is stopped. From this data, the monitoring device may indicate that the patient took the sensor away from the face for the time of eating. The sensor location then shows that sensor is on the face again (RR, Flow and HR 0) and measurement is started again. The patient placed the sensor on the face again. All of these events may be presented as graphical indicators in the graphical display.

In one period the patient is shown to be striving ("Striving"). In this regard, the measured data indicates that the patient climbs to upstairs into the bedroom to sleep, and the graphical display indicates measurements during high effort. In association with this period, the location data indicates that the patient is moving through the living room towards the stairs (α, L). The data further indicates that patient is in the upright position and walking (steps). RR, flow and HR is markedly increased due to the effort by the patient. The monitoring device 4 determines, based on a combination of these factors, that the patient is striving, and the designation is visually indicated on the graphical display.

The monitoring device 4 detects, based on the location data, that the patient is close to the first step of the (pre-programmed) stairs. Location and sensor information recording may be ongoing, or started (e.g., at a higher rate) at this time. The monitoring device 4 detects movement through the stairs and climbing (α, β, L). RR, flow and HR increase, and the sensor data shows the patient in an upright position and walking (steps). The monitoring device 4 then detects and visually indicates that the that patient is close to the last step of the stairs. At this point, the location and sensor information recording may be reduced in frequency or paused/stopped.

In one period the patient is shown to be sleeping ("Sleeping"). In this regard, the location data indicates that patient is moving towards the living room upstairs (α, L) and finally reaches the bed. The sensor shows that patient is in the upright position and walking (steps) and finally lays down. RR, flow and HR start to decrease. The monitoring device 4 determines, based on a combination of these factors, that the patient is sleeping, and the designation is visually indicated on the graphical display. According to the depicted example, location and sensor information recording may be started when patient's position stationary, laying down and breathing stable (for example RR and flow variance <1 and HR variability <10).

Figure 66C:
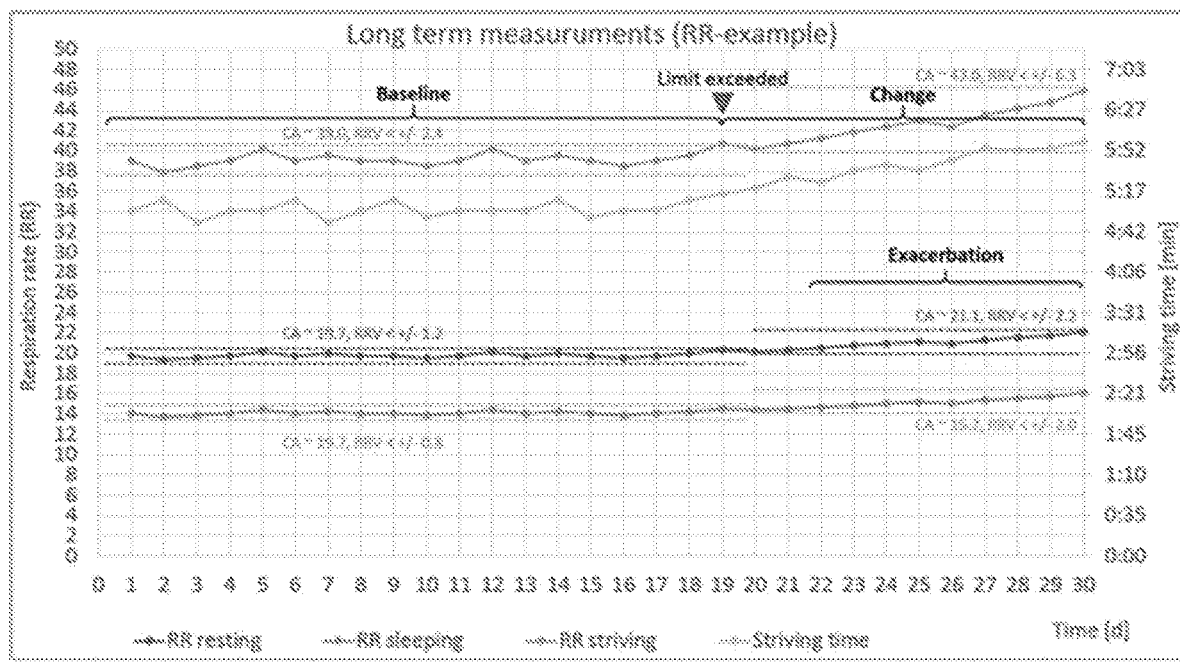
FIG. 66C illustrates another example graphical display of real time measurements for indicating whether a patient is likely to experience a health event, according to illustrative implementations.

FIG. 66C illustrates a second graphical display of real time measurements for indicating whether a patient is likely to experience a health event, according to various aspects of the subject technology. The depicted example, graphical display visually indicates the patient baseline, and where a limit has been exceeded. Graphical display further depicts when the deviation from the baseline is representative of a patient exacerbation or health event. On detecting the patient exacerbation or health event, monitoring device 4 may provide a visual indication or alert on graphical display ("Exacerbation") that is distinguishable from other indications on the display. In some implementations, detection of the patient exacerbation or health event may further cause monitoring device 4 to provide a notification to a remote device, such as a mobile device of a caregiver associated with the patient.

XIII. Sensor Rise Times

Figure 67:
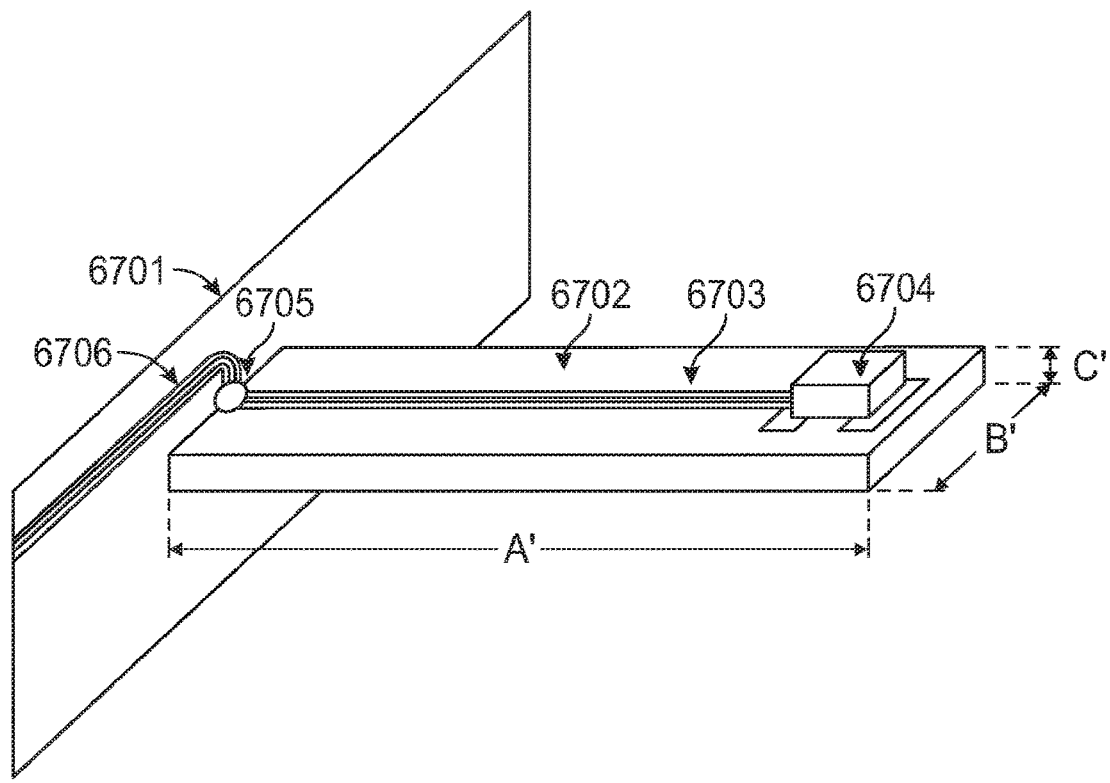
FIG. 67 illustrates a side perspective detail view of an electronics assembly of a sensor device, according to illustrative implementations.

Turning now to FIG. 67, there is shown a detailed view of an electronics assembly 6700 for a sensor device, such as sensor device 2. As described above, sensor device 2 may be any of a respiration sensor 100*a*, 100*b*, 100*c*. The electronics assembly 6700 may include support structures, such as support structure 6702. Examples of support structure 6702 may include support structures 1230-1, 1230-2, 1230-3, as shown in FIG. 30. The support structure 6702 may be configured to support sensors, such as sensor 6704. Examples of sensor 6704 may include, but are not limited to, thermistors, such as thermistors 400-1, 400-2, 400-3, as shown in FIG. 30, thermocouples, and the like.

In some implementations, as described above, the support structure 6702 may include electrically and/or thermally insulating material. In some implementations, the support structure 6702 may include, but are not limited to, fiberglass, epoxy resin, flame retardant material, and the like, and/or any combination thereof. In some implementations, thermal conductivity of the materials of the support structure 6702 may be less than 0.29 watt/(meter*kelvin) (W/(m*K)). In some implementations, the thermal conductivity of the support structures may be between 0.29 W/(m*K) and 0.343 W/(m*K).

As shown in FIG. 67, size of the support structure 6702 may be of a length A', a width B', and of a thickness or a height C'. In some implementations, a length A' of the support structure 6702 may be between 10 millimeters (mm) and 50 mm. For example, the length A' of the support structure 6702 may be 20 mm. In some implementations, a width B' of the support structure 6702 may be between 0.1 mm and 5 mm. For example, the width B' of the support structure 6702 may be 1 mm. A thickness or height C' of the support structure 6702 may be between 0.01 mm and 0.5 mm. For example, the thickness or height C' of the support structure 6702 may be 0.1 mm.

The support structure 6702 may be electrically connected to the electronics board 6701. For example, the support structure 6702 may be soldered to the electronics board 6701, such as at position 6705, to form electrical connections between the electrical connection of electronics board 6701, such as electrical connections 6706, and the electrical connections of the support structure, such as electrical connections 6703. In some implementations, width of the electrical connection 6703 may be between 25 μm and 200 μm. For example, the width of the electrical connection 6703 may be 150 μm. In some implementations, thickness of the electrical connection 6703 may be between 5 μm and 50 μm. For example, the thickness of the electrical connection 6703 may be 30 μm. In some implementations, electrical connections 6703 and 6704 may comprise electrical wires. The material of electrical wires of the electrical connections 6703 and 6704 may be copper.

The sensor 6704 may be electrically connected to the support structure 6702. For example, the sensor 6704 may be soldered to the electrical connections 6703 of the support structure 6702. In some implementations, a length of the sensor 6704 may be between 0.1 mm and 2 mm. For example, the length of the sensor 6704 may be 1 mm. In some implementations, a width of the sensor 6704 may be between 0.1 mm and 1 mm. For example, the width of the sensor 6704 may be 0.5 mm. In some implementations, a thickness or height of the sensor 6704 may be between 0.1 mm and 1 mm. For example, the thickness or height of the sensor 6704 may be 0.5 mm.

Materials included in the components surrounding the sensor 6704, and/or size of the components surrounding the sensor 6704 may affect the thermal mass surrounding the sensor 6704. Thermal mass surrounding the sensor 6704 may affect a rise time of the sensor 6704, and/or a response time of the sensor 6704. For example, an increase in thermal mass may result in an increased rise time and/or a slower response time of the sensor 6704. Similarly, a decrease in thermal mass may result in a decreased rise time and/or faster response time of the sensor 6704. In some implementations, as referred to herein a rise time of a sensor may be the time taken to change from a first value to a second value. In some implementations, the first value may be a first percentage of a final output value of the sensor, and the second value may be a second percentage of the final output value. For example, the first value may be 10% of the final output value of the sensor 6704, and the second value may be 90% of the final output value.

Figure 68:
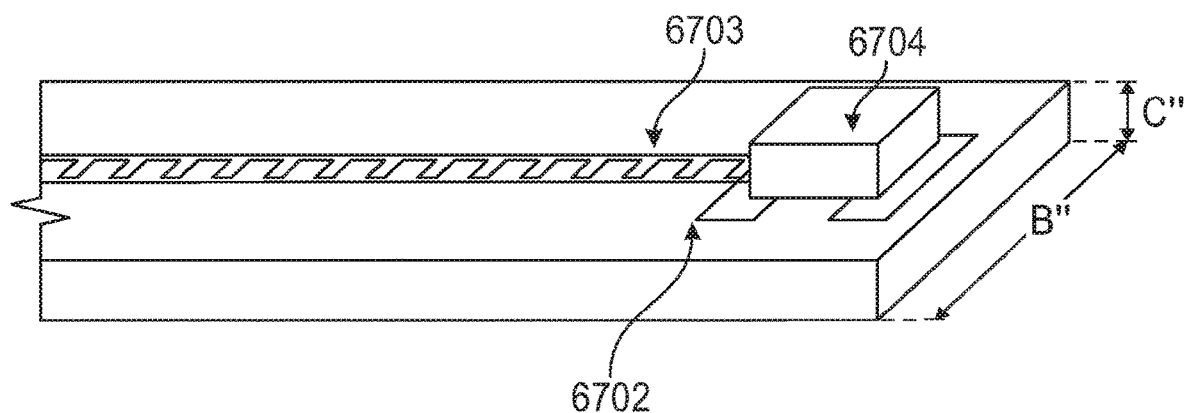
FIG. 68 illustrates a side perspective detail view of an electronics board of a sensor device, according to illustrative implementations.

In some implementations, thermal mass surrounding the sensor 6704 may be reduced by using materials with very low thermal conductivity and/or very high thermal insulating properties in the components surrounding the sensor. For example, thermal mass of support structure 6702 may be reduced by using materials with a thermal conductivity of less than 0.29 W/(m*K). In some implementations, the thermal mass surrounding a sensor may be reduced by reducing the size and/or dimensions of the components around the sensor 6704. For example, as shown in FIG. 68, the size of the support structure 6702 may be reduced by reducing the width B' and thickness C' of the support structure 6702. As an example, the width B' of the support structure 6702 may be reduced to 0.7 mm and the thickness C' of the support structure may be reduced to 0.08 mm.

In some implementations, the thermal mass surrounding the sensor 6704 may be reduced by reducing size of the electrical connections 6703. For example, a width of an electric connection may be reduced to 50 μm and a thickness of the electric connection may be reduced to 14 μm. In some implementations, the thermal mass surrounding the sensor 6704 may be reduced by reducing size of the sensor 6704. For example, the size of the sensor 6704 may be reduced to have a length of 0.5 mm, a width of 0.25 mm, and a thickness of 0.25 mm. In some implementations, the thermal mass surrounding the sensor 6704 may be reduced based on a pattern of the electrical connection 6703. For example, the electrical connection 6703 may be implemented on the support structure 6702 in an undulated pattern, as shown in FIG. 68.

Reducing the thermal mass surrounding the sensor 6704 may optimize the sensitivity of the sensor 6704 to thermal changes. In some implementations, the improvement to sensitivity of the sensor 6704 may configure the sensor 6704 to detect thermal changes across a range of breath frequencies and/or respiration rates of the patient. For example, if the sensor 6704 is a thermistor, such as the thermistor 401-1 (shown in FIG. 30), then the sensor 6704 may detect thermal changes at respiration rates of 120 breaths per minute (bpm) or greater. Similarly, the sensor 6704 may detect thermal changes at respiration rates of 10 bpm or less. In some implementations, the sensor 6704 may also detect thermal changes between respiration rates of 10 bpm and 120 bpm.

In some implementations, a rise time of the sensor 6704 may be between 0.3 degrees Celsius per second (° C./s) and 2.6° C./s. For example, the rise time of the sensor 6704 may be 0.32° C./s. In some implementations, a rise time of the sensor 6704 may be between 0.7° C./s and 1.6° C./s. In some implementations, it may be preferred to have a high response time to detect changes in temperatures more rapidly and the rise time of the sensor 6704 may be preferred to be between 0.7° C./s and 1.6° C./s. For example, the rise time of the sensor 6704 may be 0.77° C./s. In some implementations, it may be preferred to capture more detailed changes in temperatures at very high respiration rates (e.g., 120 breaths per minute) and the rise time of the sensor 6704 may be preferred to be greater than 1.29° C./s, such as between 1.3° C./s and 1.6° C./s.

Figure 69:
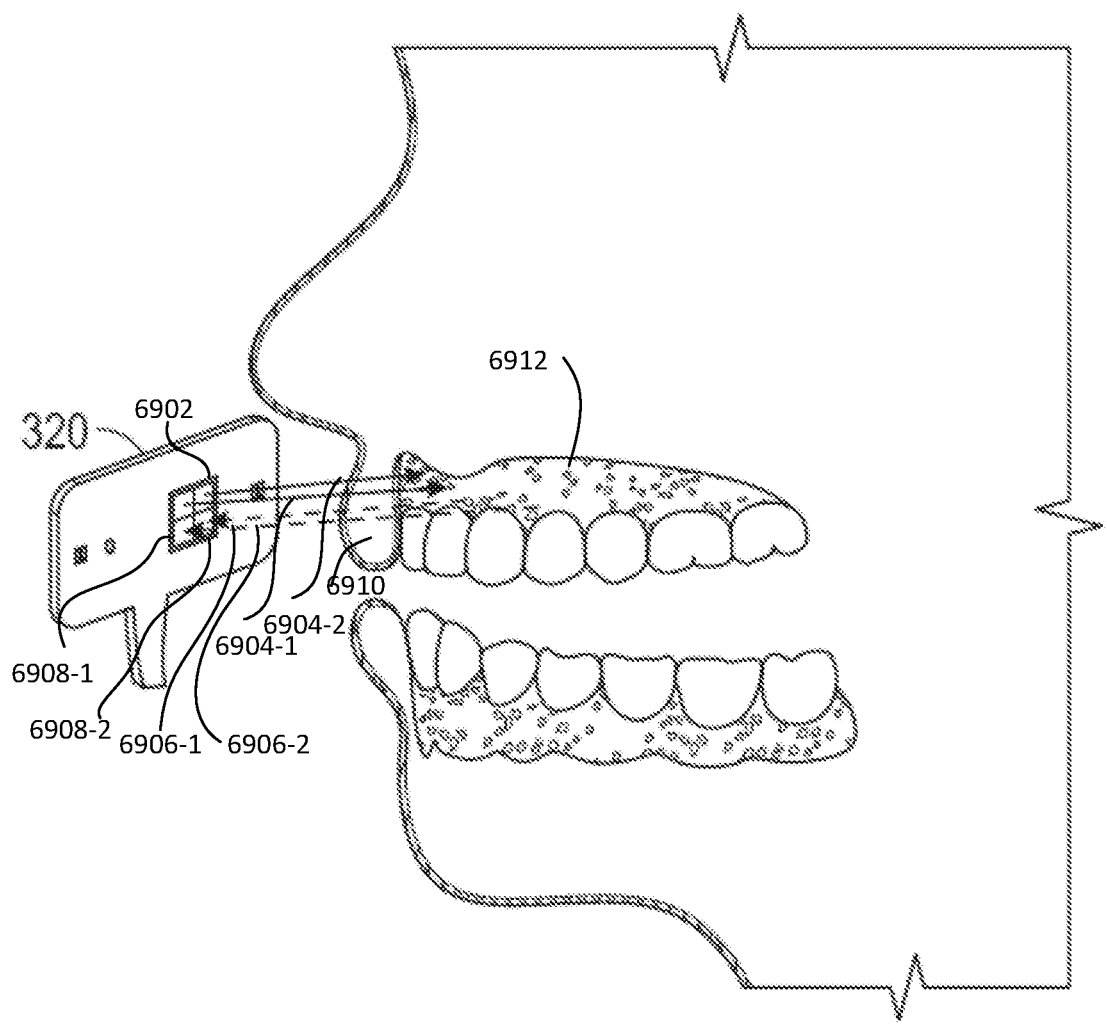
FIG. 69 illustrates a side perspective detail view of an electronics board of a sensor device, according to illustrative implementations.

In some implementations, a sensor device 2, (including e.g., respiration sensors 100*a*, 110*b*) may be configured with a sensor to measure SpO2 and/or oxygen saturation of a patient. An example of the sensor device 2 configure with a sensor to measure SpO2 and oxygen saturation of a patient is shown FIG. 69. In FIG. 69, sensor 6902 may be coupled to a frame sensor device, such as frame 320, as described above with reference to FIG. 28. The sensor 6902 may be placed against a lip 6910 of a patient when the patient wears the sensor device.

The sensor 6902 may be configured with at least one light emitting diode configured with emitting a red light 6904-1 and at least one light emitting diode emitting an infrared light 6904-2. The sensor 6902 may be configured to transmit the red light 6904-1 and the infrared light 6904-2. When transmitted from the sensor 6902, the red light 6904-1 and the infrared light 6904-2 transmit through the lip 6910 of the patient and reflect off a bone behind the lip 6910 of the patient, such as bone 6912 of the patient.

The sensor 6902 may be configured with a red light detector 6908-1 and an infrared light detector 6908-2, and the reflected red light 6906-1 may be detected and/or measured by the red light detector 6908-1 and the reflected infrared light 6906-2 may be detected and/or measured by the infrared light detector 6908-2. The sensor 6902 may be configured to calculate the levels of the measured red light and infrared light. The sensor 6902 may be configured to calculate oxygen saturation based on the calculated levels of the red light and the infrared light.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A respiration sensor comprising: a housing having a first nasal flow passage and a second nasal flow passage that extend therethrough, wherein the first and second nasal flow passages are disposed in parallel to one another with respect to a nasal respiratory flow direction; and an electronics board comprising a first nasal thermistor and a second nasal thermistor, the electronics board coupled to the housing such that the first and second nasal thermistors are positioned into each of the first and second nasal flow passages, respectively.

Clause 2. The respiration sensor of Clause 1, wherein the electronics board comprises a support structure, the support structure having a proximal portion coupled to the electronics board and a distal portion transverse to a plane defined by a top of the electronics board, wherein, when the electronics board is positioned within the housing, the distal portion of the support structure extends into at least one of the first and second nasal flow passages.

Clause 3. The respiration sensor of Clause 2, wherein any of the first or second nasal thermistors are coupled to the distal portion of the support structure.

Clause 4. The respiration sensor of any of Clauses 1 and 2, further comprising an oral flow passage and an oral thermistor, the oral flow passage disposed transverse to the first and second nasal flow passages, along an oral respiratory flow direction.

Clause 5. The respiration sensor of Clause 4, wherein the electronics board comprises a support structure having a proximal portion coupled to the electronics board and a distal portion extending along a plane defined by a top of the electronics board wherein, when the electronics board is positioned within the housing, the distal portion of the support structure extends into at least one of the first and second nasal flow passages.

Clause 6. The respiration sensor of Clause 5, wherein the oral thermistor is coupled to the distal portion of the support structure.

Clause 7. The respiration sensor of any of Clauses 4 to 6, further comprising at least one oral flow guide disposed in the oral flow passage.

Clause 8. The respiration sensor of Clause 7, wherein a first oral flow guide of the at least one oral flow guide is disposed proximate an oral inlet of the oral flow passage and a second oral flow guide of the at least one oral flow guide is disposed proximate an oral outlet of the oral flow passage.

Clause 9. The respiration sensor of Clause 8, wherein any of the oral inlet and the oral outlet is elliptical.

Clause 10. The respiration sensor of any of Clauses 8 and 9, wherein the oral flow passage tapers from the oral inlet toward the oral outlet.

Clause 11. The respiration sensor of any of Clause 1 to 10, further comprising a third thermistor and a fourth thermistor, wherein the third thermistor is an ambient thermistor and the fourth thermistor is a skin thermistor configured to determine whether the respiration sensor is properly positioned against a patient's physiognomy.

Clause 12. The respiration sensor of Clause 11, wherein the electronics board further comprises a filter configured to subtract a first electrical signal detected by the skin thermistor from a second electrical signal detected by the ambient thermistor.

Clause 13. The respiration sensor of any of Clauses 11 and 12, wherein the electronics board further comprises a filter configured to subtract a first electrical signal detected by the skin thermistor and a second electrical signal detected by any of the first and second nasal thermistors and an oral thermistor from a third electrical signal detected by the ambient thermistor.

Clause 14. The respiration sensor of any of Clauses 1 to 13, further comprising a shroud configured to protect the electronics board and to form at a least a portion of the first and second nasal flow passages.

Clause 15. The respiration sensor of any of Clauses 1 to 14, wherein the electronics board further comprises an accelerometer configured to detect movement of the respiration sensor.

Clause 16. The respiration sensor of Clause 15, wherein the accelerometer is configured to determine whether the respiration sensor has fallen from a face of a patient or the patient has fallen.

Clause 17. The respiration sensor of any of Clauses 1 to 16, wherein the electronics board further comprises a radio transceiver configured to communicate with an external device that is coupled with a network.

Clause 18. The respiration sensor of any of Clauses 2 to 17, wherein the electronics board comprises a capacitive sensor configured to detect a contact between the housing and a patient's face, when the respiration sensor is in condition for use.

Clause 19. The respiration sensor of any of Clauses 1 to 18, further comprising at least one nasal flow guide disposed in each of the first and second nasal flow passages.

Clause 20. The respiration sensor of Clause 19, wherein a first nasal flow guide of the at least one nasal flow guide is disposed proximate a nasal inlet of one of the first and second nasal flow passages, and a second nasal flow guide of the at least one nasal flow guide is disposed proximate a nasal outlet of the one of the first and second nasal flow passages.

Clause 21. The respiration sensor of any of Clauses 1 to 20, further comprising a battery.

Clause 22. A respiration sensor comprising: one or more thermistors configured to detect at least one of an inspiratory temperature, an expiratory temperature, an ambient temperature adjacent the respiratory sensor, or a temperature of a patient's skin engaged against the respiration sensor; an accelerometer configured to detect at least one of a movement of the patient, a position of the patient, a heart rate, or a respiration rate; and an electronics board coupled to the one or more thermistors and the one or more thermistors.

Clause 23. The respiration sensor of Clause 22, comprising a thermistor configured to detect a temperature of a patient's skin engaged against the respiration sensor.

Clause 24. The respiration sensor of Clause 22, comprising a EtCO2 sensitive surface configured to detect the presence of CO2.

Clause 25. A system, comprising: a server having a memory storing commands, and a processor configured to execute the commands to: receive, from a hub, a data indicative of a respiratory condition of a patient; transfer the data into a memory in a remote server; provide the data to a mobile computer device, upon request; and instruct the mobile computer device to graphically display the data, wherein the data comprises a temperature value from at least one of two nasal flow passages, a temperature value from an oral flow passage, a temperature value of a patient's skin surface, and a temperature value of a patient's environment.

Clause 26. The system of Clause 25, wherein the processor is configured to determine a respiration rate from the data indicative of the respiratory condition of a patient.

Clause 27. The system of any of Clauses 25 to 26, wherein the processor is configured to determine a respiration magnitude from the data indicative of the respiratory condition of a patient.

Clause 28. The system of any of Clauses 25 to 27, wherein the processor is configured to determine a probability of a patient having a stroke or the patient being under an opioid based on a variance of the data indicative of the respiratory condition of a patient.

Clause 29. A method, comprising: receiving, from a hub, a data indicative of a respiratory condition of a patient; transferring the data into a memory in a remote server; providing the data to a monitor, upon request; and instructing the monitor to graphically display the data, wherein the data comprises a temperature value from at least one of two nasal flow passages, a temperature value from an oral flow passage, a temperature value of a patient's skin surface, and a temperature value of a patient's environment.

Clause 30. The method of Clause 29, further comprising determining a respiration rate from the data indicative of the respiratory condition of a patient.

Clause 31. The method of any of Clauses 29 to 30, further comprising determining a respiration magnitude from the data indicative of the respiratory condition of a patient.

Clause 32. The method of any of Clauses 29 to 31, further comprising determining a probability of a patient having a stroke or the patient being under an opioid based on a variance of the data indicative of the respiratory condition of a patient.

Clause 33. The method of any of Clauses 29 to 32, further comprising associating, in the remote server, a patient record with the respiratory condition of the patient.

Clause 34. The method of any of Clauses 29 to 33, wherein the patient is one of a hospital patient or a home-care patient, the method further comprising alerting an emergency care unit when the respiratory condition of the patient indicates a catastrophic event.

Clause 35. A respiration sensor system comprising: a respiration sensor comprising a housing having a nasal flow passage that extends therethrough, wherein the nasal flow passage is aligned with a nasal respiratory flow direction, and an electronics board comprising a nasal thermistor, the electronics board coupled to the housing such that the nasal thermistor is positioned into the nasal flow passage; and a hub configured to move data between the respiration sensor and a network.

Clause 36. The respiration sensor system of Clause 35, wherein the hub is a smartphone.

Clause 37. The respiration sensor system of Clause 35, further comprising a monitor configured to receive data from an of the respiration sensor and the hub.

Clause 38. A method, comprising: monitoring data using a respiration sensor; receiving, by a hub separate from the respiration sensor, data from a respiration sensor; transmitting, from the hub to a network, the data from the respiration sensor; and transmitting, from the network to a monitor, the data from the respiration sensor.

Clause 39. The method of Clause 38, wherein the data monitored by the respiration sensor is monitored via at least one of a skin thermistor, an ambient thermistor, at least one nasal thermistor, an oral thermistor, an accelerometer, and a breath indicator.

Clause 40. The method of Clause 39, further comprising receiving, by the hub from the respiration sensor, a notification indicating a correctly-placed-no-breath state, wherein receiving the notification is in response to the respiration sensor determining that the skin thermistor is detecting a skin temperature, the ambient thermistor is detecting an ambient air temperature, one of the at least one nasal thermistor and the oral thermistor is detecting the ambient air temperature, and the breath indicator is detecting breaths.

Clause 41. The method of any of Clauses 39 to 40, further comprising receiving, by the hub from the respiration sensor, a notification indicating a loose state, wherein receiving the notification is in response to the respiration sensor determining that the skin thermistor is detecting an ambient air temperature, the ambient thermistor is detecting the ambient air temperature, one of the at least one nasal thermistor and the oral thermistor is detecting a gas flow temperature, and the breath indicator is detecting breaths.

Clause 42. The method of any of Clauses 39 to 41, further comprising receiving, by the hub from the respiration sensor, a notification indicating any of a detached or no breath state, wherein receiving the notification is in response to the respiration sensor determining that the skin thermistor is detecting an ambient air temperature, the ambient thermistor is detecting the ambient air temperature, one of the at least one nasal thermistor and the oral thermistor is detecting the ambient air temperature, and the breath indicator is detecting no breaths.

Clause 43. The method of any of Clauses 39 to 42, further comprising receiving, by the remote hub from the respiration sensor, a notification indicating an operating temperature exceeded state, wherein receiving the notification is in response to the respiration sensor determining that the skin thermistor is detecting a skin temperature and the ambient thermistor is detecting a temperature equal to or greater than the skin temperature.

Clause 44. A method, comprising: measuring, by a first sensor device, a physiological parameter of a patient proximate to the first sensor device; automatically broadcasting, by the first sensor device, responsive to measuring the physiological parameter, a wireless advertisement signal configured to facilitate a pairing process between the first sensor device and a first monitoring device; receiving, by the first sensor device after broadcasting the wireless advertisement signal, a wireless request to perform the pairing process between the first sensor device and the first monitoring device; and automatically completing the pairing process responsive to receiving the wireless request.

Clause 45. The method of Clause 44, further comprising: receiving, during the pairing process, a patient identifier of a patient, wherein the patient identifier is collected prior to the pairing process being initiated; and completing the pairing process based on receiving the patient identifier.

Clause 46. The method of Clause 45, further comprising: automatically associating, by the first sensor device, responsive to receiving the patient identifier, the patient identifier with an identifier associated with the first sensor device.

Clause 47. The method of any of Clauses 44 to 45, further comprising: prior to broadcasting the wireless advertisement signal, determining whether a value of the measured physiological parameter satisfies a threshold physiological parameter value; and automatically transmitting the wireless advertisement signal when the value of the measured physiological parameter satisfies the threshold physiological parameter value.

Clause 48. The method of Clause 47, wherein the value of the measured physiological parameter satisfying the threshold physiological parameter value requires a predetermined number of measurements of the physiological parameter being at or above a predetermined value.

Clause 49. The method of any of Clauses 44 to 48, further comprising: receiving, at the first sensor device, data related to a color associated with the first sensor device from the monitoring device, and displaying the color on an LED of the first sensor device.

Clause 50. The method of clause 49, further comprising: providing, by the sensor device to the monitoring device, before receiving the data related to the color, an identifier associated with the first sensor device, wherein the color is based on the identifier associated with first sensor device.

Clause 51. The method of clause 49, wherein the color is determined based on colors associated with other sensor devices within a threshold distance of the first sensor device.

Clause 52. The method of any of Clauses 44 to 51, further comprising: detecting a loss of a wireless connection to the first monitoring device; receiving, responsive to broadcasting a second wireless advertisement signal, a second wireless request to perform a second pairing process between the first sensor device and a second monitoring device; transmitting, immediately after completing the second pairing process, the patient identifier to the second monitoring device; and causing association of the second monitoring device with the patient.

Clause 53. A method comprising: receiving, by a monitoring device, breathing data indicating a breathing pattern of a patient and motion data indicating a movement of the patient while the breathing data is collected; comparing, by the monitoring device, the motion data and one or more predetermined motion patterns associated with a lip movement; determining, by the monitoring device, based on the comparison, that the motion data was collected when the patient is talking; and adjusting, by the monitoring device, based on the determination, the breathing data.

Clause 54. The method clause 53, further comprising: determining, by the monitoring device, based on the received breathing data, a current placement location of the sensor device on a face of the patient; and initiating the step of comparing the motion data and the one or more predetermined motion patterns associated with the lip movement, in response to determining the placement location of the sensor device.

Clause 55. The method of clause 54, wherein the placement location is a location within a predetermined distance of a lip of the patient.

Clause 56. The method of clause 53, further comprising: determining, by the monitoring device, a similarity level between the motion data and at least one of the one or more predetermined motion patterns; determining that the motion data was collected when the patient is talking based on the similarity level satisfying a threshold similarity level; and adjusting, by the monitoring device, the breathing data based on determining that the motion data was collected when the patient is talking.

Clause 57. The method of clause 53, further comprising: receiving, by the monitoring device, from the sensor device, audio data collected by a microphone of the sensor device while the breathing data is collected; determining, by the monitoring device, based on the audio data and the comparison, that the patient is talking; and; adjusting, by the monitoring device, the breathing data based on determining that the motion data was collected when the patient is talking.

Clause 58. The method of clause 57, further comprising: determining, by the monitoring device, whether a decibel level of the audio data satisfies a threshold decibel level; and initiating the step of comparing the motion data and the one or more predetermined motion patterns in response to determining the decibel level satisfies the threshold decibel level.

Clause 59. The method of clause 53, further comprising: determining, by the monitoring device, a difference between the breathing data and baseline breathing data indicating baseline breathing patterns of the patient; determining, by the monitoring device, whether the difference satisfies a threshold difference; and; adjusting, by the monitoring device, based on the determination that the difference satisfies the threshold difference and the determination that the patient is talking, the breathing data.

Clause 60. The method of clause 59, wherein the breathing data is adjusted to reduce the difference and satisfy the threshold difference.

Clause 61. The method of clause 59, wherein the breathing data is received for a first period of time.

Clause 62. The method of clause 61, further comprising: determining, by the monitoring device, the baseline breathing data based on breathing data indicating breathing patterns of the patient for a second period of time, wherein the second period of time occurs prior to the first period of time.

Clause 63. A method comprising: receiving, by a monitoring device, from a sensor device, breathing data indicating a breathing pattern of a patient and motion data indicating a movement of the patient while the breathing data is collected; determining, by the monitoring device, based on the received motion data and the received breathing data, a position of the sensor device on a face of the patient in a three-dimensional space; and providing, by the monitoring device, for display on a display device, a graphical representation of the position.

Clause 64. The method of clause 63, further comprising: comparing the motion data and the breathing data with one or more predetermined sleep patterns, at least one of the one or more predetermined sleep patterns associated with an indication of sleep apnea; generating an apnea score, by the monitoring device, based on the comparing, indicating a likelihood that the patient is experiencing sleep apnea; generating an alert when the generated apnea score satisfies a threshold likelihood level; and providing, by the monitoring device, for display on the display device, an indication of the alert together with the graphical representation of the position.

Clause 65. The method of clause 63, further comprising: determining, by the monitoring device, based on the breathing data, a first breathing pattern indicating a first respiratory rate and flow rate of a first nostril of the patient and a second breathing pattern indicating a second respiratory rate and flow rate of a second nostril of the patient; comparing the first breathing pattern and the second breathing pattern with one or more predetermined breathing patterns; and determining, based on comparing the first breathing pattern and the second breathing pattern with the one or more predetermined breathing patterns, the position of the sensor device on the face of the patient.

Clause 66. The method of clause 65, further comprising: determining a third breathing pattern indicating a third respiratory rate or a flow rate of a mouth of the patient; determining that the third respiratory rate or flow rate is greater than at least one of the first respiratory rate or flow rate and the second respiratory rate or flow rate; and generating, based on determining that the third respiratory rate or flow rate is greater, an alert indicating a nasal cavity condition.

Clause 67. The method of clause 65, further comprising: detecting that the sensor device moved in a horizontal direction based on changes in the first respiratory rate or flow rate and the second respiratory rate or flow rate.

Clause 68. The method of clause 63, further comprising: determining, based on the motion data, a physical position of the patient in the three-dimensional space, the physical position being selected from a sitting position, standing position, and lying position; determining whether the physical position of the patient breaches a predetermined medical instruction associated with the patient; and generating an alert when the physical position breaches the medical instruction.

Clause 69. The method of clause 63, further comprising: determining, by the monitoring device, a geographical location of the monitoring device; and automatically modifying, by the monitoring device, based on the geographical location of the monitoring device and a user identifier granted access to the monitoring device, a GUI of the monitoring device by adding or removing one or more graphical components on the GUI.

Clause 70. The method of clause 63, further comprising: comparing the motion data with one or more predetermined motion patterns associated with an indication of pain; generating a pain score, by the monitoring device, indicating a likelihood that the patient is experiencing pain based on the comparing; and providing, by the monitoring device, for display on the display device, a graphical element indicating the likelihood that the patient is experiencing pain.

Clause 71. The method of clause 63, wherein the motion data includes accelerometer data collected by an accelerometer embedded in the sensor device.

Clause 72. The method of clause 64, wherein the one or more predetermined sleep patterns comprises a predetermined movement pattern of a patient's head relative to a fixed position during a predetermined period of time associated with a predetermined breathing pattern for the predetermined period of time, and wherein the apnea score is generated based on a strength of similarity between the predetermined movement pattern and a current movement pattern identified by the received motion data, and the predetermined breathing pattern and a current breathing pattern identified by the received breathing data for a period of time equivalent to the predetermined period of time.

Clause 73. A method comprising: receiving, by a monitoring device, physiological data of a patient and physical motion data indicating movement of the patient data from a sensor device associated with a the patient, wherein the motion data is measured while the physiological data is collected and the physical movement data are measured during a same period of time; selecting, by the monitoring device, based on the physical movement motion data, a predetermined activity category from a plurality of predetermined activity categories; identifying, by the monitoring device, based on the selected predetermined activity category, a baseline physiological value from a plurality of baseline physiological values; determining, by the monitoring device, based on the identified baseline physiological value, a difference between a value in the physiological data and the identified baseline physiological value; predicting, by the monitoring device, based on the determined difference, a likelihood that the patient will experience a Chronic Obstructive Pulmonary Disease (COPD) exacerbation within a predetermined period of time from a current time.

Clause 74. The method of clause 73, further comprising: receiving, by the monitoring device, location data of the patient from the sensor device, wherein the location data is measured while the physiological data is collected during the same period of time; determining, by the monitoring device, based on the location data and the physical motion data, a path traveled by the patient; identifying, by the monitoring device, the baseline physiological value based on the path and the selected predetermined activity category.

Clause 75. The method of clause 74, further comprising: generating, by the monitoring device, a graphical user interface (GUI) indicating a plurality of paths traveled by the patient, wherein each path is indicated by a graphical path line and associated with the path; and providing, by the monitoring device, the GUI for display at a display device associated with the monitoring device.

Clause 76. The method of clause 75, further comprising: for each of the plurality of paths travelled by the patient: determining, by the monitoring device, a number of times the path is traveled by the patient in a recent period of time, wherein a size of the graphical path line is based on the number of times the patient traveled the path.

Clause 77. The method of clause 75, further comprising: generating, by the monitoring device, the plurality of baseline physiological values based on physiological data measured during different earlier periods of time; and associating, by the monitoring device, each of the plurality of baseline physiological values with a predetermined activity category selected from the plurality of predetermined activity categories, wherein the predetermined activity category is selected based on physical movement data measured during a corresponding earlier period of time.

Clause 78. The method of clause 77, wherein each path from the plurality of paths traveled by the patient is associated with a baseline physiological value from the plurality of baseline physiological values, and wherein each associated baseline physiological value is generated based on physiological data measured during a period of time the patient traveled the associated path.

Clause 79. The method of clause 73, further comprising: determining, by the monitoring device, based on the physical movement data, whether the patient travelled vertically, wherein the physical movement data comprises accelerometer data, positional data, and orientation data; and in response to determining that the patient travelled vertically, visually indicating, by the monitoring device, a vertical movement of the patient in three-dimensional space.

Clause 80. A respiration sensor comprising: a housing having a first nasal flow passage and a second nasal flow passage that extend therethrough, wherein the first and second nasal flow passages are disposed in parallel to one another; and an electronics board comprising a first sensor and a second sensor, the electronics board coupled to the housing such that the first sensor is positioned into the first nasal flow passage and the second sensor is positioned into the second nasal flow passage.

Clause 81. The respiration sensor of Clause 80, wherein the electronics board comprises a support structure, wherein the support structure comprises materials with a thermal conductivity less than 0.29 watt/(meter*kelvin) (W/(m*K).

Clause 82. The respiration sensor of Clause 81, wherein any of the first or second sensors are electrically coupled to a portion of the support structure by one or more electrical wires.

Clause 83. The respiration sensor of Clause 82, wherein the electrical wires are traced in an undulated pattern on the support structure.

Clause 84. The respiration sensor of Clause 81, wherein a width of the support structure is less than 0.71 mm.

Clause 85. The respiration sensor of Clause 81, wherein a thickness of the support structure is less than 0.81 mm.

Clause 86. The respiration sensor of Clause 82, wherein a width of the one or more electrical wires is less than 60 micrometers.

Clause 87. The respiration sensor of Clause 82, wherein a thickness of the one or more electrical wires is less than 20 micrometers.

Clause 88. The respiration sensor of Clause 82, wherein a rise time of any of the first and second sensors is 0.71° C./s.

Clause 89. The respiration sensor of Clause 82, wherein a rise time of any of the first and second sensors is 0.32° C./s.

Clause 90. A system comprising: a first monitoring device and a first sensor device, the first sensor device comprising a memory and one or more processors configured to execute instructions stored on the memory to cause the first sensor device to perform the steps in the method in clauses 44 to 52.

Clause 91. A system comprising: a sensor device and a monitoring device, the monitoring device comprising a memory and one or more processors configured to execute instructions stored on the memory to cause the monitoring device to perform the steps in the method in clauses 53 to 62

Clause 92. A system comprising: a sensor device and a monitoring device, the monitoring device comprising a memory and one or more processors configured to execute instructions stored on the memory to cause the monitoring device to perform the steps in the method in clauses 63 to 72.

Clause 93. A system comprising: a sensor device and a monitoring device, the monitoring device comprising a memory and one or more processors configured to execute instructions stored on the memory to cause the monitoring device to perform the steps in the method in clauses 73 to 79.

Further Consideration

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim. The word "exemplary" is used herein to mean "serving as an example, instance, or illustration." Any embodiments described herein as "exemplary" is not necessarily to be construed as preferred or advantageous over other embodiments.

In one or more aspects, the terms "about," "substantially," and "approximately" may provide an industry-accepted tolerance for their corresponding terms and/or relativity between items.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A non-transitory machine-readable memory medium comprising instructions stored thereon that, when executed by a sensor device, cause the sensor device to:
   measure, by a sensor device, a physiological parameter of a patient proximate to the sensor device;
   responsive to measuring the physiological parameter, automatically broadcasting, by the sensor device, a wireless advertisement signal configured to facilitate a pairing process between the sensor device and a monitoring device;
   receive, by the sensor device after broadcasting the wireless advertisement signal, a wireless request to perform the pairing process between the sensor device and the monitoring device; and
   automatically complete the pairing process responsive to receiving the wireless request.

2. The non-transitory machine-readable memory medium of claim 1, wherein the instructions further cause the sensor device to:
   receive, during the pairing process, a patient identifier of the patient, wherein the patient identifier is collected prior to the pairing process being initiated; and
   complete the pairing process based on receiving the patient identifier.

3. The non-transitory machine-readable memory medium of claim 2, wherein the instructions further cause the sensor device to:
   automatically associate, by the sensor device, responsive to receiving the patient identifier, the patient identifier with an identifier associated with the sensor device.

4. The non-transitory machine-readable memory medium of claim 2, wherein the instructions further cause the sensor device to:
   detect a loss of a wireless connection to the monitoring device;
   receive, based on broadcasting a second wireless advertisement signal, a second wireless request to perform a second pairing process between the sensor device and a second monitoring device;
   transmit, immediately after completing the second pairing process, the patient identifier to the second monitoring device; and
   cause association of the second monitoring device with the patient.

5. The non-transitory machine-readable memory medium of claim 1, wherein the instructions further cause the sensor device to:
   prior to broadcasting the wireless advertisement signal, determine whether a value of the measured physiological parameter satisfies a threshold physiological parameter value; and automatically transmit the wireless advertisement signal when the value of the measured physiological parameter satisfies the threshold physiological parameter value.

6. The non-transitory machine-readable memory medium of claim 5, wherein the value of the measured physiological parameter satisfying the threshold physiological parameter value requires a predetermined number of measurements of the physiological parameter being at or above a predetermined value.

7. The non-transitory machine-readable memory medium of claim 1, wherein the instructions further cause the sensor device to:
receive, at the sensor device, data related to a color associated with the sensor device
from the monitoring device, and displaying the color on an LED of the sensor device.

8. The non-transitory machine-readable memory medium of claim 7, wherein the instructions further cause the sensor device to:
provide, by the sensor device to the monitoring device, before receiving the data related to the color, an identifier associated with the sensor device, wherein the color is based on the identifier associated with sensor device.

9. The non-transitory machine-readable memory medium of claim 7, wherein the instructions further cause the sensor device to:
determine the color is based on colors associated with other sensor devices within a threshold distance of the sensor device.

10. The non-transitory machine-readable memory medium of claim 1, wherein the instructions further cause the sensor device to:
detect when a portion of the sensor device is in contact with a portion of the patient's body; and
measure the physiological parameter responsive to detecting that the portion of the sensor device is in contact with the portion of the patient's body.

11. A system, comprising:
a memory device; and
one or more processors configured to:
identify a patient;
automatically, based on identifying the patient, initiate a pairing process to communicatively couple a monitoring device with a sensor device;
determine, after the initiation of the pairing process, a wireless advertisement signal was received by the monitoring device from the sensor device, the wireless advertisement signal indicating that the sensor device has received a physiological parameter from the patient and is ready to be paired to the monitoring device;
cause the monitoring device to be paired with the sensor device based on the wireless advertisement signal being received by the monitoring device; and
cause the monitoring device to receive, responsive to the pairing, from the sensor device, the physiological parameter, the physiological parameter being detected by the sensor device prior to the monitoring device and the sensor device being paired.

12. The system of claim 11, wherein the one or more processors are further configured to:
receive an identifier associated with sensor device;
determine a color associated with the sensor device based on the identifier associated with the sensor device; and
automatically associate the color with the monitoring device and the sensor device; and cause the color to be displayed on an LED of the sensor device or the monitoring device.

13. The system of claim 12, wherein the one or more processors are further configured to:
determine, before the pairing process is initiated, the sensor device from among a plurality of sensor devices based on identifying the patient; and
determine the color associated with the sensor device based on colors associated with
other sensor devices of the plurality of sensor devices in a particular geographical location.

14. The system of claim 12, wherein the one or more processors are further configured to:
associate the color associated with the sensor device with a patient identifier associated with the patient.

15. The system of claim 12, wherein the one or more processors are further configured to:
transmit data indicating the color to the sensor device; and
cause the color to be displayed in a multicolor light emitting diode (LED) on the sensor device.

16. The system of claim 12, wherein the one or more processors are further configured to:
associate one or more display components on the monitoring device with the color associated with the sensor device; and
display at least a portion of the one or more display components in the color associated with the sensor device.

17. The system of claim 11, wherein the one or more processors are further configured to:
determine whether a value of the measured physiological parameter satisfies a threshold physiological parameter value; and
cause the wireless advertisement signal to be received by the monitoring device when the value of the measured physiological parameter satisfies the threshold physiological parameter value.

18. The system of claim 17, wherein the value of the measured physiological parameter satisfying the threshold physiological parameter value requires a predetermined number of measurements of the physiological parameter being at or above a predetermined value.

19. The system of claim 11, further comprising:
the sensor device, the one or more processors being further configured to:
determine when a portion of the sensor device is in contact with a portion of the patient's body; and
cause the sensor device to measure the physiological parameter when the sensor device detects that the portion of the sensor device is in contact with the portion of the patient's body.

20. The system of claim 11, wherein the one or more processors are further configured to:
provide, after the monitoring device and the sensor device being paired, a visualization of the physiological parameter for display in a graphical user interface on a display device.

* * * * *